United States Patent
Josyula et al.

(10) Patent No.: US 7,265,140 B2
(45) Date of Patent: Sep. 4, 2007

(54) ACYLOXYMETHYLCARBAMATE PRODRUGS OF OXAZOLIDINONES

(75) Inventors: Vara Prasad Venkata Nagendra Josyula, Ann Arbor, MI (US); Robert C. Gadwood, Portage, MI (US); Lisa Marie Thomasco, Mystic, CT (US); Ji-Young Kim, Ann Arbor, MI (US); Allison Laura Choy, Ann Arbor, MI (US); Frederick Earl Boyer, Canton Township, MI (US)

(73) Assignee: Pfizer Inc, New York, NY (US)

( * ) Notice: Subject to any disclaimer, the term of this patent is extended or adjusted under 35 U.S.C. 154(b) by 544 days.

(21) Appl. No.: 10/937,187

(22) Filed: Sep. 9, 2004

(65) Prior Publication Data

US 2005/0267104 A1 Dec. 1, 2005

Related U.S. Application Data

(60) Provisional application No. 60/505,329, filed on Sep. 23, 2003.

(51) Int. Cl.
*A61K 31/422* (2006.01)
*C07D 263/04* (2006.01)
(52) U.S. Cl. ...................... 514/376; 548/215; 548/225; 548/229; 514/374

(58) Field of Classification Search ................ 548/215, 548/225, 229; 514/374, 376
See application file for complete search history.

(56) References Cited

FOREIGN PATENT DOCUMENTS

WO WO97/09328 3/1997

OTHER PUBLICATIONS

Folkman, Michael and Frantz J. Lund; "Acyloxymethyl Carbonochloridates. New Intermediates in Prodrug Synthesis," Synthesis, 1990, pp. 1159-1166.
Mulvihilli, Mark J., et. al., "Synthesis and Application of Novel Glyoxylate-derived Chloroformates," Synthesis, 2002, pp. 365-370.
Rautio, Jarkko, et. al., "Synthesis and In Vitro Evaluation of Aminoacyloxyalkyl Esters of 2-(6-methoxy-2-naphthyl) propionic Acid as Novel Naproxen Prodrugs for Dermal Drug Delivery," Pharmaceutical Research, vol. 16, No. 8, 1999, pp. 1172-1178.
Wheeler, W.J., et. al., Journal of Medicinal Chemistry, vol. 22, No. 6, 1979, pp. 657-661.

*Primary Examiner*—Golam M. M. Shameem
(74) *Attorney, Agent, or Firm*—Steve Zelson; Jason G. Tebbutt

(57) ABSTRACT

The present invention relates to acyloxymethylcarbamate oxazolidinones. The compounds of the present invention have potent activity with excellent oral bioavailability against Gram-positive and Gram-negative bacteria.

34 Claims, No Drawings

ACYLOXYMETHYLCARBAMATE PRODRUGS OF OXAZOLIDINONES

CROSS-REFERENCE TO RELATED APPLICATIONS

This application claims the benefit of the following provisional application; Ser. No. 60/505,329, filed Sep. 23, 2003, under 35 U.S.C. 119(e)(1).

FIELD OF INVENTION

The present invention relates to acyloxymethylcarbamate oxazolidinones and their preparations. The compounds of the present invention have potent activity with excellent oral bioavailability against Gram-positive and Gram-negative bacteria.

BACKGROUND OF THE INVENTION

Due to ever-increasing antibiotic resistance, structurally novel antibacterials with a new mode of action have become increasingly important in the treatment of bacterial infections. Effective antibacterials should exhibit potent activity against a number of human and veterinary pathogens, including gram-positive aerobic bacteria such as multiply-resistant staphylococci and streptococci, anaerobic organisms such as *bacteroides* and *clostridia* species, and acid-fast organisms such as *Mycobacterium tuberculosis* and *Mycobacterium avium*.

Among newer antibacterial agents, oxazolidinone compounds are the most recent synthetic class of antimicrobials active against a number of pathogenic microorganisms. However, some of these oxazolidinones are not absorbed sufficiently to achieve the desired blood levels in a mammalian subject. This invention provides a new type of oxazolidinone prodrug which remarkably enhances oral bioavailability of the compounds described herein. Prodrugs of the present invention are prepared by modifying functional groups present in a compound described herein in such a way that the modifications may be cleaved in vivo to release the parent compound.

SUMMARY OF THE INVENTION

The present invention provides a compound of formula I

I or a pharmaceutically acceptable salt thereof wherein:

X is —SO—, —SO$_2$—, or —SONR$^6$—;

Z is —C—, —CH—, or —N—;

each " . . . " is independently absent, or a bond;

each W is independently —CHR$^6$—, —CHR$^6$CH$_2$—, or absent;

R$^1$ is
(a) —NH$_2$,
(b) —NHC$_{1-4}$alkyl,
(c) —C$_{1-6}$alkyl, optionally substituted with 1-3 halo,
(d) —C$_{2-6}$alkenyl,
(e) —(CH$_2$)$_n$C(=O)C$_{1-4}$alkyl,
(f) —OC$_{1-4}$alkyl,
(g) —SC$_{1-4}$alkyl, or
(h) —(CH$_2$)$_n$C$_{3-7}$cycloalkyl;

R$^2$ and R$^3$ are independently —H, or —F;

R$^4$ is —H, —C$_{1-4}$alkyl, or —CO$_2$R$^6$;

R$^5$ is
(a) —C$_{1-10}$alkyl,
(b) —C$_{3-7}$cycloalkyl,
(c) -aryl,
(d) -het,
(e) —OC$_{1-10}$alkyl,
(f) —O—C$_{3-7}$cycloalkyl,
(g) —O-aryl,
(h) —O-het,
(i) —C(R$^6$)(R$^7$)NH$_2$,
(j) —C(R$^6$)(R$^7$)NHCO$_2$C$_{1-4}$alkyl,
(k) —C(R$^6$)(R$^7$)NHCOC(R$^6$)(R$^7$)NH$_2$, or
(l) —C(R$^6$)(R$^7$)NHCOC(R$^6$)(R$^7$)NHCO$_2$C$_{1-4}$alkyl;

each R$^6$ is independently —H, or —C$_{1-4}$alkyl;

each R$^7$ is independently —H, —C$_{1-4}$alkyl wherein —C$_{1-4}$alkyl is optionally substituted with OR$^6$, SR$^6$$_3$, CO$_2$R$^6$, CONH$_2$, NH$_2$, NHC(=NH)NH$_2$, phenyl, het, or R$^6$ and R$^7$ taken together form het;

aryl is phenyl, biphenyl, or naphthyl;

het is an aromatic ring, or a saturated or unsaturated ring that is not aromatic, of 3 to 10 carbon atoms and 1 to 4 heteroatoms selected from the group consisting of O, NQ, and S within the ring, wherein Q is absent, H, C$_{1-4}$ alkyl or —CO$_2$C$_{1-4}$alkyl;

at each occurrence, C$_{1-10}$alkyl is optionally substituted with 1-3 halo, OH, CN, NO$_2$, OC$_{1-4}$ alkyl, NR$^6$R$^6$, C(=O)C$_{1-4}$alkyl, OC(=O)C$_{1-4}$alkyl, C(=O)OC$_{1-4}$alkyl, phenyl or S(O)$_n$C$_{1-4}$alkyl;

at each occurrence, C$_{3-7}$cycloalkyl is optionally substituted with 1-3 halo, OH, CN, NO$_2$, C$_{1-4}$ alkyl, OC$_{1-4}$ alkyl, NR$^6$R$^6$, C(=O)C$_{1-4}$alkyl, OC(=O)C$_{1-4}$alkyl, C(=O)OC$_{1-4}$ alkyl, or S(O)$_n$C$_{1-4}$alkyl;

at each occurrence, aryl is optionally substituted with 1-3 halo, OH, CN, NO$_2$, C$_{1-4}$alkyl, OC$_{1-4}$ alkyl, NR$^6$R$^6$, C(=O)C$_{1-4}$alkyl, OC(=O)C$_{1-4}$alkyl, C(=O)OC$_{1-4}$alkyl, or S(O)$_n$ C$_{1-4}$alkyl;

at each occurrence het is optionally substituted with 1-3 halo, OH, CN, NO$_2$, C$_{1-4}$alkyl, OC$_{1-4}$ alkyl, NR$^6$R$^6$, C(=O)C$_{1-4}$alkyl, OC(=O)C$_{1-4}$alkyl, C(=O)OC$_{1-4}$alkyl, S(O)$_n$ C$_{1-4}$ alkyl, or oxo;

and each n is independently 0-4.

In another aspect, the present invention also provides:

a pharmaceutical composition which comprises a pharmaceutically acceptable carrier and an effective amount of a compound of formula I, a method for treating gram-positive microbial infections in a mammal by administering to the subject in need a therapeutically effective amount of a compound of formula I or a pharmaceutically acceptable salt thereof, a method for treating gram-negative microbial infections in a mammal by administering to the subject in need a therapeutically effective amount of a compound of formula I or a pharmaceutically acceptable salt thereof, and a use of a compound of formula I or a pharmaceutically acceptable salt thereof to prepare a medicament for treating gram-positive or gram-negative microbial infections.

DETAILED DESCRIPTION OF THE INVENTION

The invention may also provide some novel intermediates and processes that are useful for preparing compounds of formula I.

Unless otherwise stated, the following terms used in the specification and claims have the meanings given below:

The carbon atom content of various hydrocarbon-containing moieties is indicated by a prefix designating the minimum and maximum number of carbon atoms in the moiety, i.e., the prefix $C_{i-j}$ indicates a moiety of the integer "i" to the integer "j" carbon atoms, inclusive. Thus, for example, $C_{1-7}$ alkyl refers to alkyl of one to seven carbon atoms, inclusive.

The term alkyl, alkenyl, etc. refer to both straight and branched groups, but reference to an individual radical such as "propyl" embraces only the straight chain radical, a branched chain isomer such as "isopropyl" being specifically referred to. Alkyl is optionally substituted with 1-3 halo, OH, CN, $NO_2$, $OC_{1-4}$ alkyl, $NR^6R^6$, $C(=O)C_{1-4}$alkyl, $OC(=O)C_{1-4}$alkyl, $C(=O)OC_{1-4}$alkyl, or $S(O)_nC_{1-4}$alkyl.

The term "cycloalkyl" refers to a cyclic saturated monovalent hydrocarbon group of three to seven carbon atoms, e.g., cyclopropyl, cyclohexyl, and the like. Cycloalkyl is optionally substituted with 1-3 halo, OH, CN, $NO_2$, $C_{1-4}$ alkyl, $OC_{1-4}$ alkyl, $NR^6R^6$, $C(=O)C_{1-4}$alkyl, $OC(=O)C_{1-4}$alkyl, $C(=O)OC_{1-4}$alkyl, or $S(O)_nC_{1-4}$alkyl.

The term "halo" refers to fluoro (F), chloro (Cl), bromo (Br), or iodo (I).

The term "aryl" refers to phenyl, biphenyl, or naphthyl, optionally substituted with 1-3 halo, OH, CN, $NO_2$, $C_{1-4}$alkyl, $OC_{1-4}$ alkyl, $NR^6R^6$, $C(=O)C_{1-4}$alkyl, $OC(=O)C_{1-4}$alkyl, $C(=O)OC_{1-4}$alkyl, or $S(O)_nC_{1-4}$alkyl.

The term "het" refers to an aromatic ring, or a saturated or unsaturated ring that is not aromatic, of 3 to 10 carbon atoms and 1 to 4 heteroatoms selected from the group consisting of oxygen, nitrogen, and sulfur within the ring. Het is optionally substituted with 1-3 halo, OH, CN, $NO_2$, $C_{1-4}$alkyl, $OC_{1-4}$ alkyl, $NR^6R^6$, $C(=O)C_{1-4}$alkyl, $OC(=O)C_{1-4}$alkyl, $C(=O)OC_{1-4}$alkyl, $S(O)_nC_{1-4}$alkyl, or oxo. An examples of het includes, but are not limited to, azetidine, pyrrole, imidazole, pyrazole, 1,2,3-triazole, 1,3,4-triazole, oxazole, thiazole, isoxazole, isothiazole, 1,3,4-oxadiazole, 1,3,4-thiadiazole, 1,2,3-thiadiazole, tetrazole, pyridine, pyrazine, pyrimidine, pyridazine, indolizine, isoindole, indole, dihydroindole, indazole, purine, quinolizine, isoquinoline, quinoline, phthalazine, quinoxaline, quinazoline, cinnoline, pteridine, carbazole, carboline, phenanthridine, acridine, phenanthroline, isothiazole, phenazine, isoxazole, isoxazolinone, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiadiazole tetrazole, thiazolidine, thiophene, benzo[b]thiophene, morpholine, thiomorpholine, (also referred to as thiamorpholine,), piperidine, pyrrolidine, tetrahydrofuran, or the like. Another example of het includes, but are not limited to, pyridine, thiophene, furan, pyrazole, pyrimidine, 2-pyridyl, 3-pyridyl, 4-pyridyl, 2-pyrimidinyl, 4-pyrimidinyl, 5-pyrimidinyl, 3-pyridazinyl, 4-pyridazinyl, 3-pyrazinyl, 4-oxo-2-imidazolyl, 2-imidazolyl, 4-imidazolyl, 3-isoxazolyl, 4-is-oxaz-olyl, 5-isoxazolyl, 3-pyrazolyl, 4-pyrazolyl, 5-pyrazolyl, 2-oxazolyl, 4-oxazolyl, 4-oxo-2-oxazolyl, 5-oxazolyl, 1,2,3-oxathiazole, 1,2,3-oxadiazole, 1,2,4-oxadiazole, 1,2,5-oxadiazole, 1,3,4-oxadiazole, 2-thiazolyl, 4-thiazolyl, 5-thiazolyl, 3-isothiazole, 4-isothiazole, 5-isothiazole, 2-furanyl, 3-furanyl, 2-thienyl, 3-thienyl, 2-pyrrolyl, 3-pyrrolyl, 3-isopyrrolyl, 4-isopyrrolyl, 5-isopyrrolyl, 1,2,3,-oxathiazole-1-oxide, 1,2,4-oxadiazol-3-yl, 1,2,4-oxadiazol-5-yl, 5-oxo-1,2,4-oxadiazol-3-yl, 1,2,4-thiadiazol-3-yl, 1,2,5-thiadiazol-3-yl, 1,2,4-thiadiazol-5-yl, 3-oxo-1,2,4-thiadiazol-5-yl, 1,3,4-thiadiazol-5-yl, 2-oxo-1,3,4-thiadiazol-5-yl, 1,2,4-triazol-3-yl, 1,2,4-triazol-5-yl, 1,2,3,4-tetrazol-5-yl, 5-oxazolyl, 3-isothiazolyl, 4-isothiazolyl and 5-isothiazolyl, 1,3,4,-oxadiazole, 4-oxo-2-thiazolinyl, or 5-methyl-1,3,4-thiadiazol-2-yl, thiazoledione, 1,2,3,4-thiatriazole, or 1,2,4-dithiazolone The dotted lines within the structure of formula I indicate an optional double bond at these positions.

The term "a pharmaceutically acceptable salt" of a compound means a salt that is pharmaceutically acceptable and that possesses the desired pharmacological activity of the parent compound. Such salts include:

(1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

The term "pharmaceutically acceptable carrier" means a carrier that is useful in preparing a pharmaceutical composition that is generally safe, non-toxic and neither biologically nor otherwise undesirable, and includes a carrier that is acceptable for veterinary use as well as human pharmaceutical use. "A pharmaceutically acceptable carrier" as used in the specification and claims includes both one and more than one such carrier.

The term "mammal" refers to human or warm-blooded animals including livestock and companion animals.

The term "optional" or "optionally" means that the subsequently described event or circumstance may, but need not, occur, and that the description includes instances where the event or circumstance occurs and instances in which it does not.

Compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 1992).

The term "treating" or "treatment" of a disease includes: (1) preventing the disease, i.e. causing the clinical symptoms of the disease not to develop in a mammal that may be exposed to or predisposed to the disease but does not yet experience or display symptoms of the disease; (2) inhibiting the disease, i.e., arresting or reducing the development of the disease or its clinical symptoms; or (3) relieving the disease, i.e., causing regression of the disease or its clinical symptoms.

The term "therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

The term "leaving group" has the meaning conventionally associated with it in synthetic organic chemistry i.e., an atom or group capable of being displaced by a nucleophile and includes halogen, alkylsulfonyloxy, ester, or amino such as chloro, bromo, iodo, mesyloxy, tosyloxy, trifluorosulfonyloxy, methoxy, N,O-dimethylhydroxyl-amino, and the like.

The compounds of the present invention are generally named according to the IUPAC or CAS nomenclature system.

Abbreviations which are well known to one of ordinary skill in the art may be used (e.g. "Ph" for phenyl, "Me" for methyl, "Et" for ethyl, "h" for an hour or hours and "rt" for room temperature).

Specific and preferred values listed below for radicals, substituents, and ranges, are for illustration only; they do not exclude other defined values or other values within defined ranges for the radicals and substituents.

Specifically, alkyl denotes both straight and branched groups; but reference to an individual radical such as "propyl" embraces only the straight chain radical, a branched chain isomer such as "isopropyl" being specifically referred to.

Specifically, alkyl is methyl, ethyl, propyl, isopropyl, butyl, iso-butyl, sec-butyl, and their isomeric forms thereof.

Specifically, alkenyl is vinyl, propenyl, allyl, butenyl, and their isomeric forms thereof.

Specifically, cycloalkyl is cyclopropyl, cyclobutyl, cyclopentyl, cyclohexyl, and their isomeric forms thereof.

Specifically, halo is fluoro (F), chloro (Cl).

Specifically, $R^1$ is $C_{1-4}$alkyl, optionally substituted with one, two or three fluoro (F), or chloro (Cl).

Specifically, $R^1$ is $CH_3$, or $CH_2CH_3.CHF_2$, $CF_3$, or $CHCl_2$.

Specifically, $R^1$ is $CHF_2$, $CF_3$, or $CHCl_2$.

Specifically, one of the $R^2$ and $R^3$ is fluoro (F).

Specifically, $R^4$ is H.

Specifically, $R^4$ is H, or $CH_3$.

Specifically, $R^5$ is $C_{1-5}$alkyl, optonally substituted with phenyl.

Specifically, $R^5$ is cyclopropane, cyclopentane, or cyclohexane.

Specifically, $R^5$ is phenyl.

Specifically, $R^5$ is an unsaturated het of 3 to 4 carbon atoms and 1 to 2 heteroatoms selected from the group consisting of O, NQ, and S within the ring, wherein Q is absent, H, $C_{1-4}$ alkyl or $—CO_2C_{1-4}$alkyl.

Specifically, $R^5$ is tetrahydro-pyran, piperidine, or pyrrolidine.

Specifically, $R^5$ is $C(R^6)(R^7)NH_2$ wherein $R^6$ is H or methyl; and $R^7$ is H, Me, Et, iso-propyl, sec-butyl, CH(Me)Et, benzyl, $CH_2OH$, $CH_2COOH$, $CH_2CH_2COOH$, $CONH_2$, or $CH_2CONH_2$.

Specifically, $R^5$ is $C(R^6)(R^7)NH_2$ wherein $R^6$ is H; and $R^7$ is $C_{1-5}$alkyl optionally substituted with phenyl.

Specifically, each W is independently $—CH_2—$.

Specifically, Z is $—CH—$.

Specifically, Z is $—N—$.

Specifically, X is $—SO_2—$.

Examples of the present invention are:

(1) ({[acetyl({(5R)-3-[4-(1,1-dioxidotetrahydro-2H-thiopyran4-yl)-3-fluorophenyl]-2-oxo-1,3oxazolidin-5-yl}1-methyl)amino] carbonyl}oxy)methylacetate, (2) (R)-propionic acid (acetyl-{3-[4-(1,1-dioxo-hexahydro-1λ⁶-thiopyran-4-yl)-3-fluoro-phenyl]-2-oxo-oxazolidin-5-ylmethyl}-carbamoyloxy)-methyl ester, (3) (R)-isobutyric acid (acetyl-{3-[4-(1,1-dioxo-hexahydro-1λ⁶-thiopyran-4-yl)-3-fluoro-phenyl]-2-oxo-oxazolidin-5-ylmethyl}-carbamoyloxy)-methyl ester, (4) (R)-3-methyl-butyric acid (acetyl-{3-[4-(1,1-dioxo-hexahydro-1λ⁶-thiopyran-4-yl)-3-fluoro-phenyl]-2-oxo-oxazolidin-5-ylmethyl}-carbamoyloxy)-methyl ester, (5) (R)-butyric acid (acetyl-{3-[4-(1,1-dioxo-hexahydro-1λ⁶-thiopyran-4-yl)-3-fluoro-phenyl]-2-oxo-oxazolidin-5-ylmethyl}-carbamoyloxy)-methyl ester, (6) (R)-2.2-dimethy-propionic acid (acetyl-{3-[4-(1,1-dioxo-hexahydro-1λ⁶-thiopyran-4-yl)-3-fluoro-phenyl]-2-oxo-oxazolidin-5-ylmethyl}-carbamoyloxy)-methyl ester, (7) (R)-3.3-dimethy-butyric acid (acetyl-{3-[4-(1,1-dioxo-hexahydro-1λ⁶-thiopyran-4-yl)-3-fluoro-phenyl]-2-oxo-oxazolidin-5-ylmethyl}-carbamoyloxy)-methyl ester, (8) (R)-cyclopropanecarboxylic acid (acetyl-{3-[4-(1,1-dioxo-hexahydro-1λ⁶-thiopyran-4-yl)-3-fluoro-phenyl]-oxazolidin-5-ylmethyl}-carbamoyloxy)-methyl ester, (9) (R)-cyclopentanecarboxylic acid (acetyl-{3-[4-(1,1-dioxo-hexahydro-1λ⁶-thiopyran-4-yl)-3-fluoro-phenyl]-2-oxo-oxazolidin-5-ylmethyl}-carbamoyloxy)-methyl ester,

(10) (R)-cyclohexanecarboxylic acid (acetyl-{3-[4-(1,1-dioxo-hexahydro-1λ⁶-thiopyran-4-yl)-3-fluoro-phenyl]-2-oxo-oxazolidin-5-ylmethyl}-carbamoyloxy)-methyl ester,

(11) (R)-benzoic acid (acetyl-{3-[4-(1,1-dioxo-hexahydro-1λ⁶-thiopyran-4-yl)-3-fluoro-phenyl]-2-oxo-oxazolidin-5-ylmethyl}-carbamoyloxy)-methyl ester,

(12) (R)-tetrahydro-pyran-4-carboxylic acid (acetyl-{3-[4-(1,1-dioxo-hexahydro-1$\lambda^6$-thiopyran-4-yl)-3-fluoro-phenyl]-2-oxo-oxazolidin-5-ylmethyl}-carbamoyloxy)-methyl ester,

(13) (R)-tert-butoxycarbonylamino-acetic acid (acetyl-{3-[4-(1,1-dioxo-hexahydro-1$\lambda^6$-thiopyran-4-yl)-3-fluoro-phenyl]-2-oxo-oxazolidin-5-ylmethyl}-carbamoyloxy)-methyl ester,

(14) 2(S)-tert-butoxycarbonylamino-propionic acid (acetyl-{3-[4-(1,1-dioxo-hexahydro-1$\lambda^6$-thiopyran-4-yl)-3-fluoro-phenyl]-2-oxo-oxazolidin-5(R)-ylmethyl}-carbamoyloxy)-methyl ester,

(15) 2(S)-tert-butoxycarbonylamino-3-methyl-butyric acid (acetyl-{3-[4-(1,1-dioxo-hexahydro-1$\lambda^6$-thiopyran-4-yl)-3-fluoro-phenyl]-2-oxo-oxazolidin-5(R)-ylmethyl}-carbamoyloxy)-methyl ester,

(16) 2(R)-tert-butoxycarbonylamino-3-methyl-butyric acid (acetyl-{3-[4-(1,1-dioxo-hexahydro-1$\lambda^6$-thiopyran-4-yl)-3-fluoro-phenyl]-2-oxo-oxazolidin-5(R)-ylmethyl}-carbamoyloxy)-methyl ester,

(17) 2(S)-tert-butoxycarbonylamino-4-methyl-pentanoic acid (acetyl-{3-[4-(1,1-dioxo-hexahydro-1$\lambda^6$-thiopyran-4-yl)-3-fluoro-phenyl]-2-oxo-oxazolidin-5(R)-ylmethyl}-carbamoyloxy)-methyl ester,

(18) 2(S)-tert-butoxycarbonylamino-3(S)-methyl-pentanoic acid (acetyl-{3-[4-(1,1-dioxo-hexahydro-1$\lambda^6$-thiopyran-4-yl)-3-fluoro-phenyl]-2-oxo-oxazolidin-5(R)-ylmethyl}-carbamoyloxy)-methyl ester,

(19) 2(S)-tert-butoxycarbonylamino-3-phenyl-propionic acid (acetyl-{3-[4-(1,1-dioxo-hexahydro-1$\lambda^6$-thiopyran-4-yl)-3-fluoro-phenyl]-2-oxo-oxazolidin-5(R)-ylmethyl}-carbamoyloxy)-methyl ester,

(20) Pyrrolidine-1,2-dicarboxylic acid 2(S)-[(acetyl-{3-[4-(1,1-dioxo-hexahydro-1$\lambda^6$-thiopyran-4-yl)-3-fluoro-phenyl]-2-oxo-oxazolidin-5(R)-ylmethyl}-carbamoyloxy)-methyl] ester 1-tert-butyl ester,

(21) (R)-(2-tert-butoxycarbonylamino-acetylamino)-acetic acid (acetyl-{3-[4-(1,1-dioxo-hexahydro-1$\lambda^6$-thiopyran-4-yl)-3-fluoro-phenyl]-2-oxo-oxazolidin-5-ylmethyl}-carbamoyloxy)-methyl ester,

(22) (R)-amino-acetic acid (acetyl-{3-[4-(1,1-dioxo-hexahydro-1$\lambda^6$-thiopyran-4-yl)-3-fluoro-phenyl]-2-oxo-oxazolidin-5-ylmethyl}-carbamoyloxy)-methyl ester hydrochloride,

(23) 2(S)-amino-propionic acid (acetyl-{3-[4-(1,1-dioxo-hexahydro-1$\lambda^6$-thiopyran-4-yl)-3-fluoro-phenyl]-2-oxo-oxazolidin-5(R)-ylmethyl}-carbamoyloxy)-methyl ester hydrochloride,

(24) 2(S)-tert-butoxycarbonylamino-3-methyl-butyric acid (acetyl-{3-[4-(1,1-dioxo-hexahydro-1$\lambda^6$-thiopyran-4-yl)-3-fluoro-phenyl]-2-oxo-oxazolidin-5(R)-ylmethyl}-carbamoyloxy)-methyl ester hydrochloride,

(25) 2(R)-amino-3-methyl-butyric acid (acetyl-{3-[4-(1,1-dioxo-hexahydro-1$\lambda^6$-thiopyran-4-yl)-3-fluoro-phenyl]-2-oxo-oxazolidin-5(R)-ylmethyl}-carbamoyloxy)-methyl ester hydrochloride,

(26) 2(S)-amino-4-methyl-pentanoic acid (acetyl-{3-[4-(1,1-dioxo-hexahydro-1$\lambda^6$-thiopyran-4-yl)-3-fluoro-phenyl]-2-oxo-oxazolidin-5(R)-ylmethyl}-carbamoyloxy)-methyl ester hydrochloride,

(27) 2(S)-amino-3(S)-methyl-pentanoic acid (acetyl-{3-[4-(1,1-dioxo-hexahydro-1$\lambda^6$-thiopyran-4-yl)-3-fluoro-phenyl]-2-oxo-oxazolidin-5(R)-ylmethyl}-carbamoyloxy)-methyl ester hydrochloride,

(28) 2(S)-amino-3-phenyl-propionic acid (acetyl-{3-[4-(1,1-dioxo-hexahydro-1$\lambda^6$-thiopyran-4-yl)-3-fluoro-phenyl]-2-oxo-oxazolidin-5(R)-ylmethyl}-carbamoyloxy)-methyl ester hydrochloride,

(29) Pyrrolidine-2(S)-carboxylic acid (acetyl-{3-[4-(1,1-dioxo-hexahydro-1$\lambda^6$-thiopyran-4-yl)-3-fluoro-phenyl]-2-oxo-oxazolidin-5(R)-ylmethyl}-carbamoyloxy)-methyl ester hydrochloride,

(30) (R)-(2-amino-acetylamino)-acetic acid (acetyl-{3-[4-(1,1-dioxo-hexahydro-1$\lambda^6$-thiopyran-4-yl)-3-fluoro-phenyl]-2-oxo-oxazolidin-5-ylmethyl}-carbamoyloxy)-methyl ester hydrochloride,

(31) Acetic acid 1-(acetyl-{3-[4-(1,1-dioxo-hexahydro-1$\lambda^6$-thiopyran-4-yl)-3-fluoro-phenyl]-2-oxo-oxazolidin-5(R)-ylmethyl}-carbamoyloxy)-ethyl ester,

(32) (R)-piperidine-1,4-dicarboxylic acid 4-[(acetyl-{3-[4-(1,1-dioxo-hexahydro-1$\lambda^6$-thiopyran-4-yl)-3-fluoro-phenyl]-2-oxo-oxazolidin-5-ylmethyl}-carbamoyloxy)-methyl] ester 1-tert-butyl ester,

(33) (R)-piperidine-4-carboxylic acid (acetyl-{3-[4-(1,1-dioxo-hexahydro-1$\lambda^6$ thiopyran-4-yl)-3-fluoro-phenyl]-2-oxo-oxazolidin-5-ylmethyl}-carbamoyloxy)-methyl ester hydrochloride,

(34) 2(R)-phenyl-propionic acid (acetyl-{3-[4-(1,1-dioxo-hexahydro-1$\lambda^6$-thiopyran-4-yl)-3-fluoro-phenyl]-2-oxo-oxazolidin-5(R)-ylmethyl}-carbamoyloxy)-methyl ester,

(35) 2(S)-phenyl-propionic acid (acetyl-{3-[4-(1,1-dioxo-hexahydro-1$\lambda^6$-thiopyran-4-yl)-3-fluoro-phenyl]-2-oxo-oxazolidin-5(R)-ylmethyl}-carbamoyloxy)-methyl ester,

(36) Isonicotinic acid (acetyl-{3-[4-(1,1-dioxo-hexahydro-1$\lambda^6$-thiopyran-4-yl)-3-fluoro-phenyl]-2-oxo-oxazolidin-5(R)-ylmethyl}-carbamoyloxy)-methyl ester,

(37) Propionic acid 1-(acetyl-{3-[4-(1,1-dioxo-hexahydro-1$\lambda^6$-thiopyran-4-yl)-3-fluoro-phenyl]-2-oxo-oxazolidin-5(R)-ylmethyl}-carbamoyloxy)-ethyl ester,

(38) Isonicotinic acid 1-(acetyl-{3-[4-(1,1-dioxo-hexahydro-1$\lambda^6$-thiopyran-4-yl)-3-fluoro-phenyl]-2-oxo-oxazolidin-5(R)-ylmethyl}-carbamoyloxy)-ethyl ester,

(39) 2(S)-tert-butoxycarbonylamino-3(S)-methyl-pentanoic acid 1-(acetyl-{3-[4-(1,1-dioxo-hexahydro-1$\lambda^6$-thiopyran-4-yl)-3-fluoro-phenyl]-2-oxo-oxazolidin-5(R)-ylmethyl}-carbamoyloxy)-ethyl ester,

(40) 2,2-dimethyl-propionic acid 1-(acetyl-{3-[4-(1,1-dioxo-hexahydro-1$\lambda^6$-thiopyran-4-yl)-3-fluoro-phenyl]-2-oxo-oxazolidin-5(R)-ylmethyl}-carbamoyloxy)-ethyl ester,

(41) Preparation of 2(S)-Amino-3(S)-methyl-pentanoic acid 1-(acetyl-{3-[4-(1,1-dioxo-hexahydro-1$\lambda^6$-thiopyran-4-yl)-3-fluoro-phenyl]-2-oxo-oxazolidin-5(R)-ylmethyl}-carbamoyloxy)-ethyl ester hydrochloride, or

(42) Cyclopentanecarboxylic acid 1-(acetyl-{3-[4-(1,1-dioxo-hexahydro-1$\lambda^6$-thiopyran-4-yl)-3-fluoro-phenyl]-2-oxo-oxazolidin-5(R)-ylmethyl}-carbamoyloxy)-ethyl ester.

Pharmaceutical Salts

The compound of formula I may be used in its native form or as a salt. In cases where forming a stable nontoxic acid or base salt is desired, administration of the compound as a pharmaceutically acceptable salt may be appropriate. Examples of pharmaceutically acceptable salts of the present invention include inorganic salts such as hydrochloride, hydrobromide, sulfate, nitrate, bicarbonate, carbonate salts, and organic salts such as tosylate, methanesulfonate, acetate, citrate, malonate, tartarate, succinate, benzoate, ascorbate, etoglutarate, and glycerophosphate.

Pharmaceutically acceptable salts may be obtained using standard procedures well known in the art, for example, reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Routes of Administration

The oxazolidinone antibacterial prodrugs of this invention have useful activity against a variety of organisms including, but not limiting to, *Staphylococcus aureus, Staphylococcus epidermidis, Enterococcus faecium, Streptococcus pneumoniae, Streptococcus pyogenes, Enterococcus faecalis, Moraxella catarrhalis* and *H. influenzae*. In therapeutic use for treating, or combating, bacterial infections in a mammal (i.e. human and animals) an oxazolidinone prodrug of the present invention or its pharmaceutical compositions can be administered orally, parenterally, topically, rectally, transmucosally, or intestinally.

Parenteral administrations include indirect injections to generate a systemic effect or direct injections to the afflicted area. Examples of parenteral administrations are subcutaneous, intravenous, intramuscular, intradermal, intrathecal, intraocular, intranasal, intravetricular injections or infusions techniques.

Topical administrations include the treatment of infectious areas or organs readily accessibly by local application, such as, for example, eyes, ears including external and middle ear infections, vaginal, open wound, skins including the surface skin and the underneath dermal structures, or other lower intestinal tract. It also includes transdermal delivery to generate a systemic effect.

The rectal administration includes the form of suppositories.

The transmucosal administration includes nasal aerosol or inhalation applications.

The preferred routes of administration are oral and parenteral.

Composition/Formulation

Pharmaceutical compositions of the present invention may be manufactured by processes well known in the art, e.g., by means of conventional mixing, dissolving, granulation, dragee-making, levigating, emulsifying, encapsulating, entrapping, lyophilizing processes or spray drying.

Pharmaceutical compositions for use in accordance with the present invention may be formulated in conventional manner using one or more physiologically acceptable carriers comprising excipients and auxiliaries which facilitate processing of the active compounds into preparations which can be used pharmaceutically. Proper formulation is dependent upon the route of administration chosen.

For oral administration, the compounds can be formulated by combining the active compounds with pharmaceutically acceptable carriers well known in the art. Such carriers enable the compounds of the invention to be formulated as tablets, pills, lozenges, dragees, capsules, liquids, solutions, emulsions, gels, syrups, slurries, suspensions and the like, for oral ingestion by a patient. A carrier can be at least one substance which may also function as a diluent, flavoring agent, solubilizer, lubricant, suspending agent, binder, tablet disintegrating agent, and encapsulating agent. Examples of such carriers or excipients include, but are not limited to, magnesium carbonate, magnesium stearate, talc, sugar, lactose, sucrose, pectin, dextrin, mannitol, sorbitol, starches, gelatin, cellulosic materials, low melting wax, cocoa butter or powder, polymers such as polyethylene glycols and other pharmaceutical acceptable materials.

Dragee cores are provided with suitable coatings. For this purpose, concentrated sugar solutions may be used which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical compositions which can be used orally include push-fit capsules made of gelatin, as well as soft, sealed capsules made of gelatin and a plasticizer, such as glycerol or sorbitol. The push-fit capsules can contain the active ingredients in admixture with a filler such as lactose, a binder such as starch, and/or a lubricant such as talc or magnesium stearate and, optionally, stabilizers. In soft capsules, the active compounds may be dissolved or suspended in suitable liquids, such as fatty oils, liquid paraffin, liquid polyethylene glycols, cremophor, capmul, medium or long chain mono-, di- or triglycerides. Stabilizers may be added in these formulations, also.

Liquid form compositions include solutions, suspensions and emulsions. For example, there may be provided solutions of the compounds of this invention dissolved in water and water-propylene glycol and water-polyethylene glycol systems, optionally containing suitable conventional coloring agents, flavoring agents, stabilizers and thickening agents.

The compounds may also be formulated for parenteral administration, e.g., by injections, bolus injection or continuous infusion. Formulations for parenteral administration may be presented in unit dosage form, e.g., in ampoules or in multi-dose containers, with an added preservative. The compositions may take such forms as suspensions, solutions or emulsions in oily or aqueous vehicles, and may contain formulating materials such as suspending, stabilizing and/or dispersing agents.

For injection, the compounds of the invention may be formulated in aqueous solution, preferably in physiologically compatible buffers or physiological saline buffer. Suitable buffering agents include trisodium orthophosphate, sodium bicarbonate, sodium citrate, N-methylglucamine, L(+)-lysine and L(+)-arginine.

Parenteral administrations also include aqueous solutions of a water soluble form, such as, without limitation, a salt, of the active compound. Additionally, suspensions of the active compounds may be prepared in a lipophilic vehicle. Suitable lipophilic vehicles include fatty oils such as sesame oil, synthetic fatty acid esters such as ethyl oleate and triglycerides, or materials such as liposomes. Aqueous injection suspensions may contain substances which increase the viscosity of the suspension, such as sodium carboxymethyl cellulose, sorbitol, or dextran. Optionally, the suspension may also contain suitable stabilizers and/or agents that increase the solubility of the compounds to allow for the preparation of highly concentrated solutions.

Alternatively, the active ingredient may be in powder form for constitution with a suitable vehicle, e.g., sterile, pyrogen-free water, before use. For suppository administration, the compounds may also be formulated by mixing the agent with a suitable non-irritating excipient which is solid at room temperature but liquid at rectal temperature and therefore will melt in the rectum to release the drug. Such materials include cocoa butter, beeswax and other glycerides.

For administration by inhalation, compounds of the present invention can be conveniently delivered through an aerosol spray in the form of solution, dry powder, or suspensions. The aerosol may use a pressurized pack or a nebulizer and a suitable propellant. In the case of a pressurized aerosol, the dosage unit may be controlled by providing a valve to deliver a metered amount. Capsules and cartridges of, for example, gelatin for use in an inhaler may be formulated containing a power base such as lactose or starch.

For topical applications, the pharmaceutical composition may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion such as suspensions, emulsion, or cream containing the active components suspended or dissolved in one or more pharmaceutically acceptable carriers. Suitable carriers include, but are not limited to, mineral oil, sorbitan monostearate, polysorbate 60, cetyl esters wax, ceteary alcohol, 2-octyldodecanol, benzyl alcohol and water.

For ophthalmic and otitis uses, the pharmaceutical compositions may be formulated as micronized suspensions in isotonic, pH adjusted sterile saline, or preferably, as solutions in isotonic, pH adjusted sterile saline, either with or without a preservative such as a benzylalkonium chloride. Alternatively, for ophthalmic uses, the pharmaceutical compositions may be formulated in an ointment such as petrolatum.

In addition to the formulations described previously, the compounds may also be formulated as depot preparations. Such long acting formulations may be in the form of implants. A compound of this invention may be formulated for this route of administration with suitable polymers, hydrophobic materials, or as a sparing soluble derivative such as, without limitation, a sparingly soluble salt.

Additionally, the compounds may be delivered using a sustained-release system. Various sustained-release materials have been established and are well known by those skilled in the art. Sustained-release capsules may, depending on their chemical nature, release the compounds for 24 hours or for up to several days.

Dosage

Pharmaceutical compositions suitable for use in the present invention include compositions wherein the active ingredients are contained in an amount sufficient to achieve the intended purpose, i.e., the treatment or prevent of infectious diseases. More specifically, a therapeutically effective amount means an amount of compound effective to prevent, alleviate or ameliorate symptoms of disease or prolong the survival of the subject being treated.

The quantity of active component, that is the compound of this invention, in the pharmaceutical composition and unit dosage form thereof may be varied or adjusted widely depending upon the manner of administration, the potency of the particular compound and the desired concentration. Determination of a therapeutically effective amount is well within the capability of those skilled in the art. Generally, the quantity of active component will range between 0.5% to 90% by weight of the composition.

Generally, a therapeutically effective amount of dosage of active component will be in the range of about 0.1 to about 400 mg/kg of body weight/day, more preferably about 1.0 to about 50 mg/kg of body weight/day. It is to be understood that the dosages may vary depending upon the requirements of each subject and the severity of the bacterial infection being treated. In average, the effective amount of active component is about 200 mg to 800 mg and preferable 600 mg per day.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

Also, it is to be understood that the initial dosage administered may be increased beyond the above upper level in order to rapidly achieve the desired plasma concentration. On the other hand, the initial dosage may be smaller than the optimum and the daily dosage may be progressively increased during the course of treatment depending on the particular situation. If desired, the daily dose may also be divided into multiple doses for administration, e.g., two to four times per day.

In cases of local administration or selective uptake, the effective local concentration of the drug may not be related to plasma concentration and other procedures know in the art may be used to determine the desired dosage amount.

Oral Efficacy

Bioavailability

The present invention discovers a new type of oxazolidinone prodrug which has much improved oral bioavailability. When administered to a mammalian subject, the compounds of the present are absorbed intact and then are rapidly converted to the parent oxazolidinones. Table 1 provides single dose pharmacokinetics of example 1 of the present invention and its parent compound.

TABLE 1

Single-Dose Pharmacokinetics

| Compounds | Dose mg/kg | $C_{max}$ µg/ml | F |
|---|---|---|---|
| 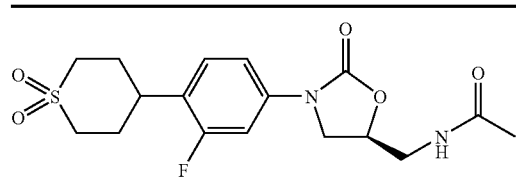 | 10 | 1.0 | 21 |

TABLE 1-continued

Single-Dose Pharmacokinetics

| Compounds | Dose mg/kg | $C_{max}$ μg/ml | F |
|---|---|---|---|
| [structure] | $10^c$ | 5.22 | 75 |

The tests were conducted in male beagle dogs, and were administered in the forms of aqueous suspension. The term "$10^c$" refers to an equivalent dose of the parent compound. The term "$C_{max}$" refers to maximum concentration achieved in the blood. It is well known that the oral efficacy is directly correlated with blood concentration. The term "F" refers to the fraction of the total dosage gets into the blood (known as bioavailability).

Methods of Preparation

The following Schemes describe the preparation of compounds of the present invention. All of the starting materials are prepared by procedures described in the scheme or by procedures that would be well known to one of ordinary skill in organic chemistry. The variables used in the Schemes are as defined below or as in the claims.

Scheme A illustrates a general synthesis of acyloxymethylcarbamate prodrugs of oxazolidinones. In scheme A, the starting amine compound a may be prepared according to PCT international publication WO 97/09328. The starting compound b is either commercial available or can be prepared according to the procedures found in the literature (*Synthesis*, 1990, 1159-1166. ibid, 2002, 365-370). Compound c can be prepared by reacting the starting compound a with structure b in the presence of a base such as diisopropylethylamine followed by a solution of acid chloride at a temperature about a 0° C. Reaction of compound c with the appropriate anhydride, such as acetic anhydride in the presence of an appropriate base such a triethylamine and

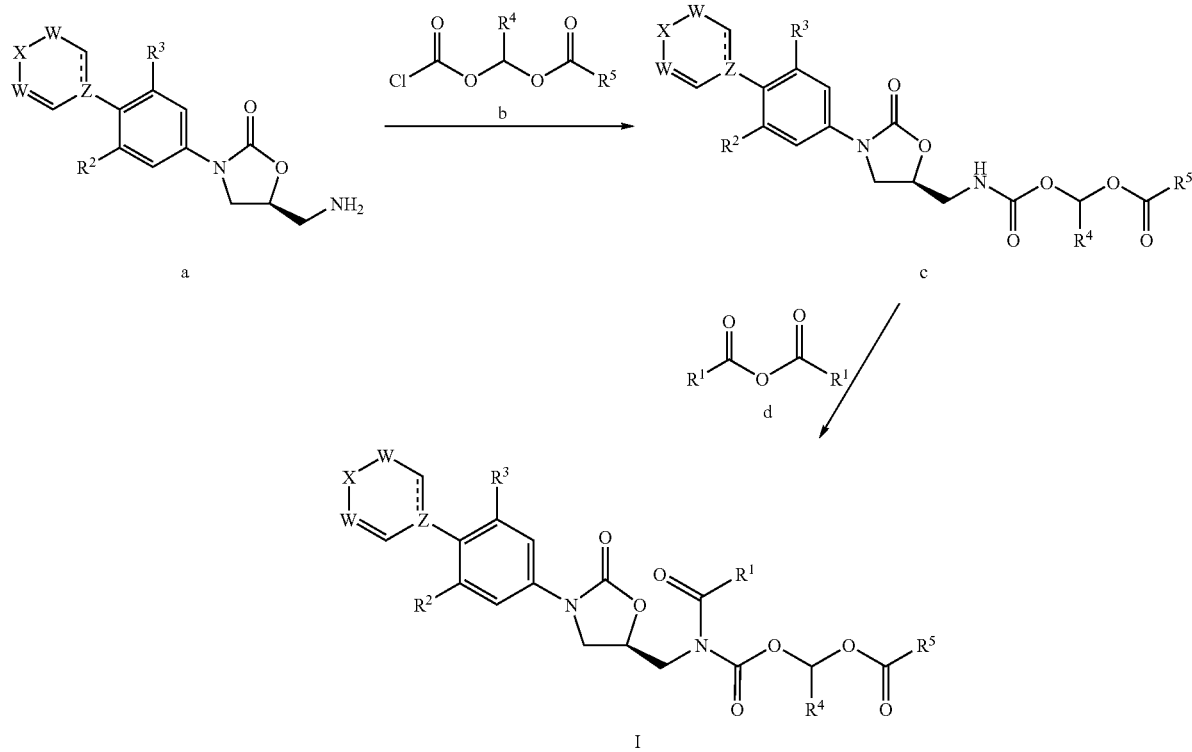

SCHEME A a catalytic amount of dimethylaminopyridine in a suitable solvent such as dichloromethane affords the desired compound of formula I.

Specific reaction conditions of Scheme B are illustrated in Rautio, J. et. Al. Pharmaceutical Research 1999, 16(8), 1172-1178; Wheeler, W. J. et. al. J. Med. Chem. 1979, 22,

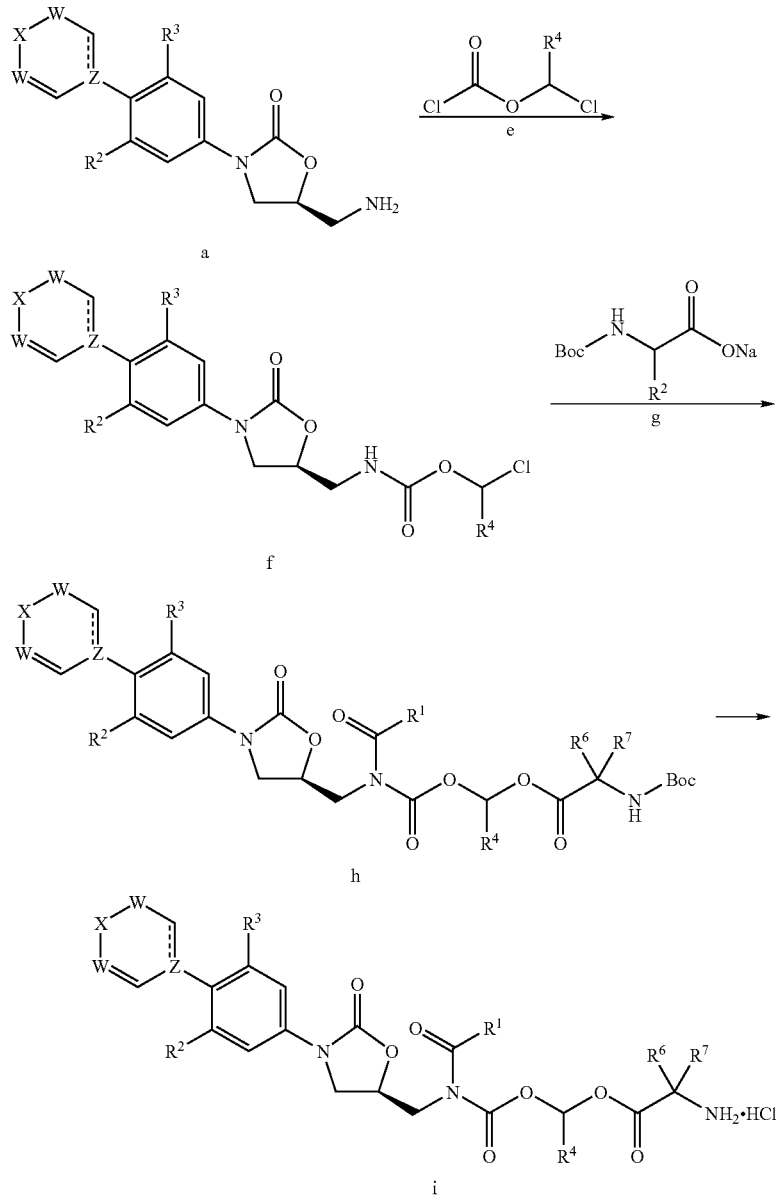

SCHEME B

Scheme B illustrates another general synthesis of acyloxymethylcarbamate prodrugs of oxazolidinones. In scheme b, the compound of structure e is either commercially available or can be readily prepared according the methods well known to one skilled in art. Compound f can be prepared by reacting the starting compound a with acid chloride e in the presence of a base such as diisopropylethylamine. Reacting a compound of structure f with a compound of structure g in the presence of a suitable salt such as potassium iodide or sodium iodide provides a protected compound of structure h. The compound of structure h reacts with acetyl chloride in the presence of a base such as triethyl amine, and then is treated with hydrogen chloride to provide compounds of the present invention.

657-661. Alternatively, acyloxymethylcarbamate prodrugs of oxazolidinones can be prepared as illustrated in Scheme C. In Scheme C, compound k can be prepared by reacting the starting compound j with acid chloride e in the presence of a base such as diisopropylethylamine or lithium t-butoide. Reacting a compound of structure k with a cesium salt of an appropriate N-BOC-amino acid l in the presence of a suitable salt such as potassium iodide or sodium iodide provides compound of structure m. Hydrolysis of compound of structure m in an acidic condition such as using hydrogen chloride provides a compound of structure p. In Schemes B and C, a person of ordinary skill in the art would know how to convert a compound of hydrogen chloride into its native form.

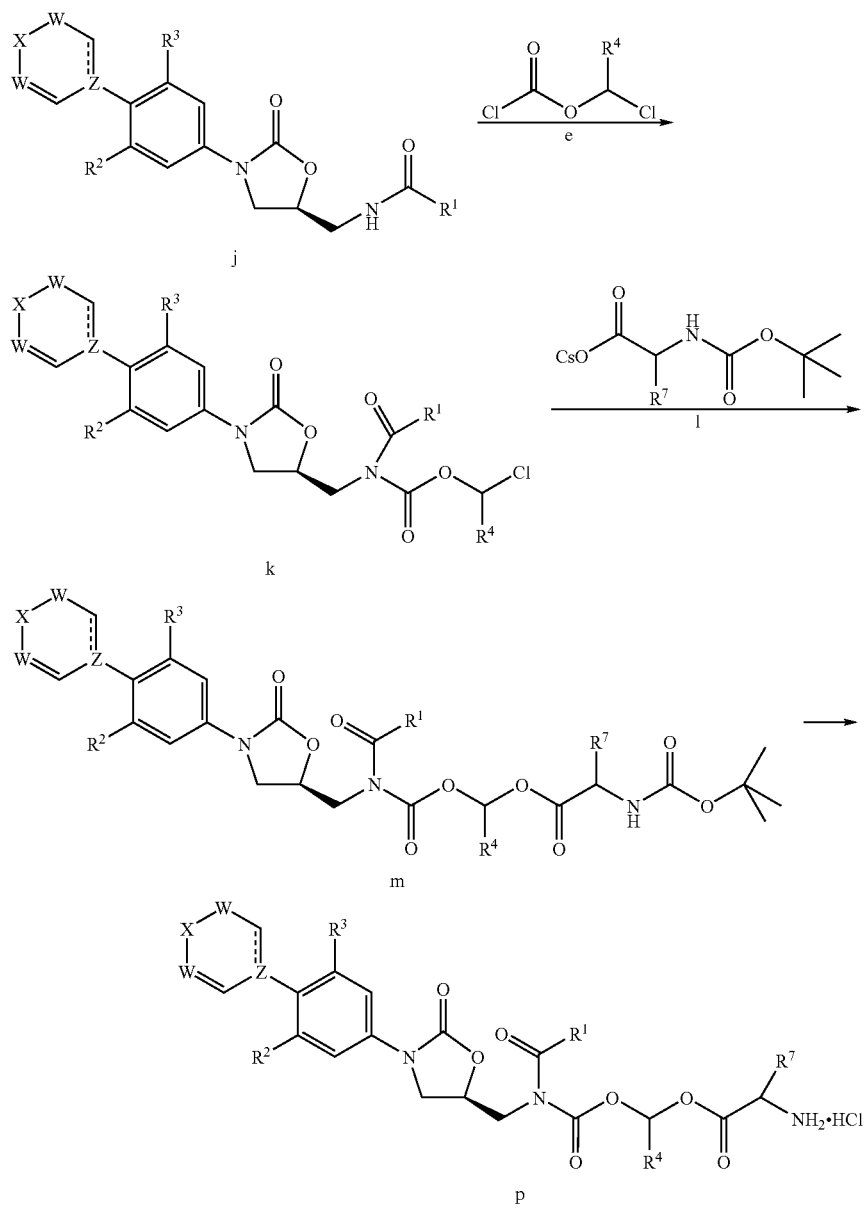

The following synthetic examples are offered to illustrate this invention and are not to be construed in any way as limiting the scope of this invention.

EXAMPLES

In the discussion above and in the examples below, the following abbreviations have the following meanings. If an abbreviation is not defined, it has its generally accepted meaning.

| | |
|---|---|
| bm = | broad multiplet |
| BOC = | tert-butoxycarbonyl |
| bd = | broad doublet |

-continued

| | |
|---|---|
| bs = | broad singlet |
| CDI = | 1,1 O-carbodiimidazole |
| d = | doublet |
| dd = | doublet of doublets |
| dq = | doublet of quartets |
| dt = | doublet of triplets |
| DMF = | dimethylformamide |
| DMAP = | dimethylaminopyridine |
| DMSO = | dimethyl sulfoxide |
| eq. = | equivalents |
| g = | grams |
| h = | hours |
| HPLC = | high pressure liquid chromatography |
| HATU = | N-[(dimethylamino)-1H-1,2,3-triazolo-[4,5-b]pyridin-1-yl-methylene]-N-methylmethanaminium |

| | |
|---|---|
| | hexafluorophosphate N-oxide |
| LG = | leaving group |
| m = | multiplet |
| M = | molar |
| M % = | mole percent |
| max = | maximum |
| meq = | milliequivalent |
| mg = | milligram |
| mL = | milliliter |
| mm = | millimeter |
| mmol = | millimol |
| q = | quartet |
| s = | singlet |
| t or tr = | triplet |
| TBS = | tributylsilyl |
| TFA = | trifluoroacetic acid |
| THF = | tetrahydrofuran |
| TLC = | thin layer chromatography |
| p-TLC = | preparative thin layer chromatography |
| μL = | microliter |
| N = | normality |
| MeOH = | methanol |
| DCM = | dichloromethane |
| HCl = | hydrochloric acid |
| ACN = | acetonitrile |
| MS = | mass spectrometry |
| rt = | room temperature |
| EtOAc = | ethyl acetate |
| EtO = | ethoxy |
| Ac = | acetate |
| NMP = | 1-methyl-2-pyrrolidinone |
| μL = | microliter |
| J = | coupling constant |
| NMR = | Nuclear magnetic resonance |
| MHz = | megahertz |
| Hz = | hertz |
| m/z = | mass to charge ratio |
| min = | minutes |
| Boc = | tert-butoxycarbonyl |
| CBZ = | benzyloxycarbonyl |
| DCC = | 1,3-dicyclohexylcarbodiimide |
| PyBop = | benzotriazole-1-yl-oxy-trispyrrolidinophosphonium hexafluorophosphate |

General Procedure 1

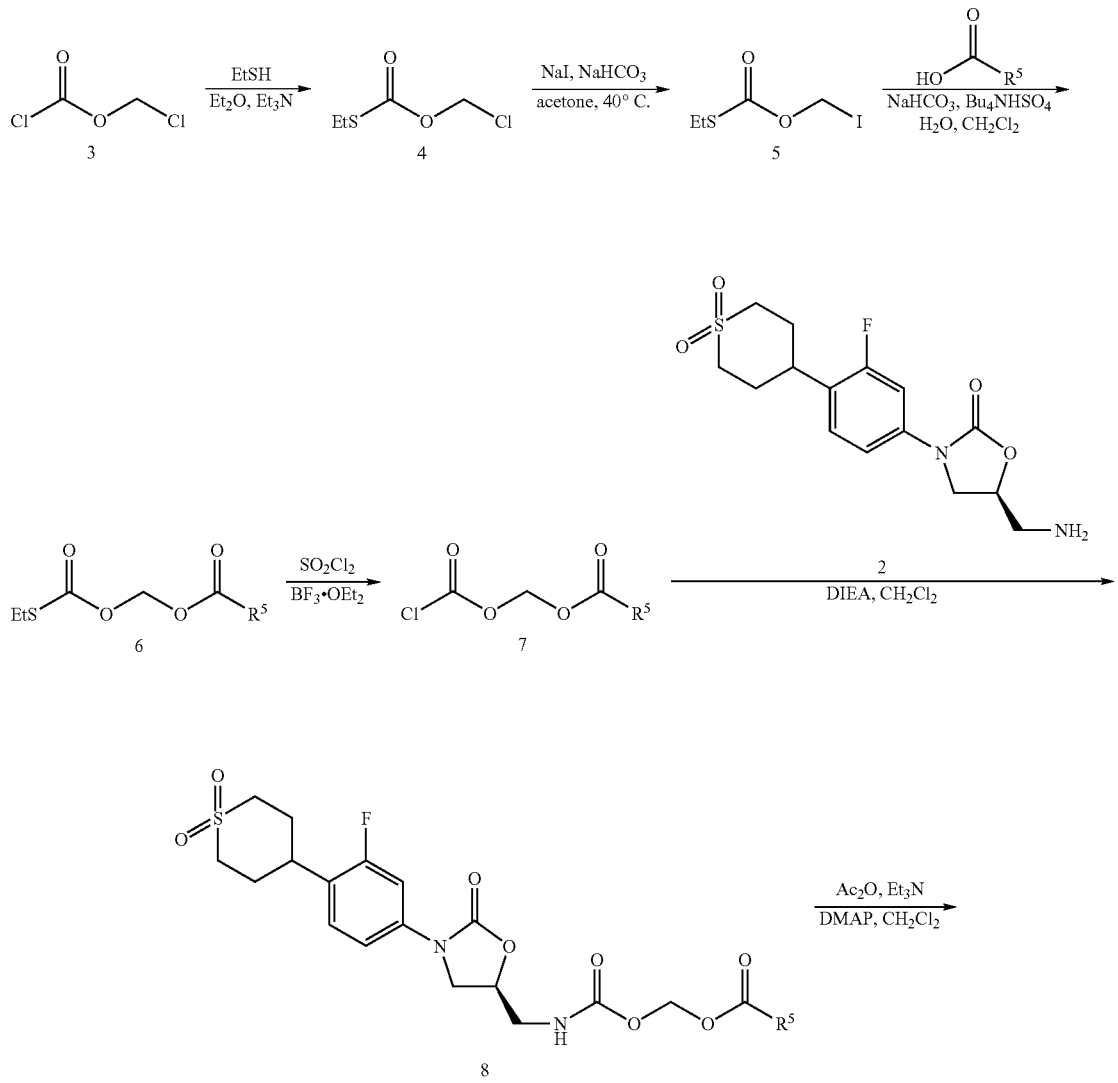

-continued

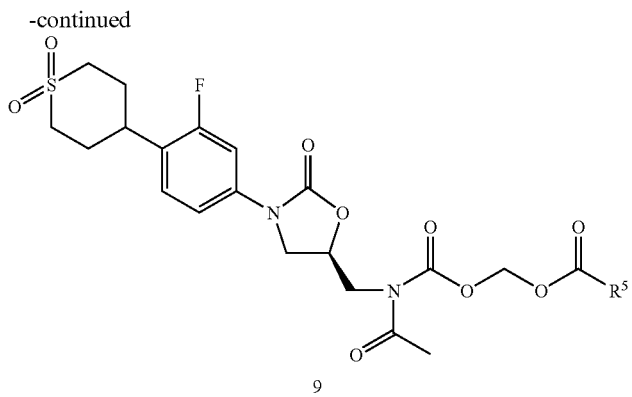

9

Preparation of (S)-5-Aminomethyl-3-[4-(1,1-dioxo-hexahydro-1λ⁶-thiopyran-4-yl)-3-fluoro-phenyl]-oxazolidin-2-one (2)

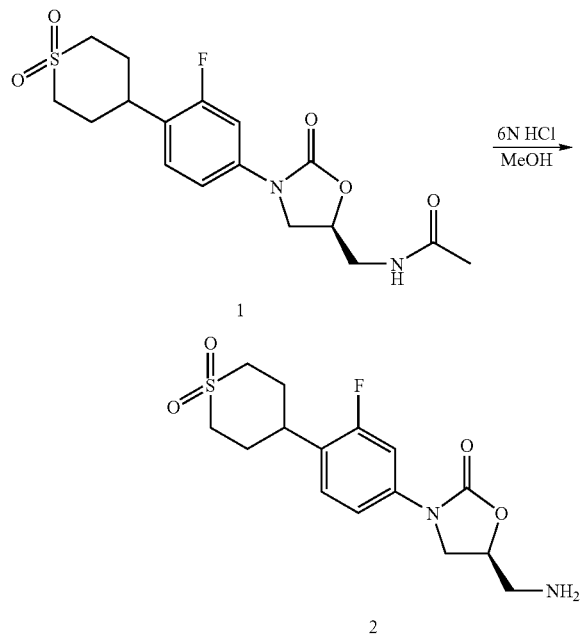

Compounds 1 and 2 may be prepared according to the PCT international publication WO 97/09328. Compound 2 may also be prepared as following:

To a slurry of (S)-N-{3-[4-(1,1-Dioxo-hexahydro-1☐⁶-thiopyran-4-yl)-3-fluoro-phenyl]-2-oxo-oxazolidin-5-ylmethyl}-acetamide (1) (1.4 g, 3.64 mmol) in methanol (72 mL) was added 6 N HCl (24 mL). The mixture was heated to reflux overnight. The mixture was then cooled to RT and conc in vacuo. Ethyl acetate and water were added to the residue and the layers were separated. The aq layer was made basic (pH 12-13) by the addition of 2 M NaOH, and then the aq layer was extracted with ethyl acetate several times. The combined organic layers were dried over $Na_2SO_4$ and conc in vacuo to give the title compound in 72% yield (0.89 g). $^1$H NMR (400 MHz, CDCl$_3$): δ 7.50 (dd, 1H), 7.19 (m, 2H), 4.67 (m, 1H), 4.00 (app t, 1H), 3.84 (dd, 1H), 3.15-3.05 (m, 6H), 2.95 (dd, 1H), 2.38 (m, 2H), 2.17 (m, 2H), 1.22 (br s, 2H). MS-APCI (m/z+): 343 (M+H), 385 (M+H+ CH$_3$CN).

Preparation of O-Chloromethyl S-ethyl carbonothioate (4), O-iodomethyl S-ethyl carbonothioate (5), the double esters (6), and the acyloxymethyl carbonochloridates (7) may be made according to the procedures described in Lund, F. J.; Folkmann, M. *Synthesis*, 1990, 1159-1166.

General Procedure A: Synthesis of Double Esters (6)

The double esters (6) are prepared according to Lund, F. J.; Folkmann, M. *Synthesis*, 1990, 1159-1166: A mixture of sodium bicarbonate (2.68 eq.), tetrabutylammonium hydrogen sulfate (1.34 eq), water, dichloromethane, and the corresponding carboxylic acid (1.34 eq) is stirred at RT for 1 h. O-Iodomethyl S-ethyl carbonothioate (5) (1 eq) is then added dropwise as a solution in dichloromethane. The reaction mixture is stirred at RT overnight. The phases are separated and the aq layer is extracted twice with dichloromethane. The combined organic layers are washed with water, dried over sodium sulfate and conc in vacuo. Ether is added to the residue and the mixture is stirred for at least 1 h. The mixture is filtered and the filtrate is conc in vacuo to give the desired product.

General Procedure B: Synthesis of Acyloxymethyl Carbonochloridates (7)

The acyloxymethyl carbonochloridates (7) are prepared according to Lund, F. J.; Folkmann, M. *Synthesis*, 1990, 1159-1166: The appropriate thioester (6) is cooled to 0° C. and sulfuryl chloride (1 eq) is added followed by the addition of BF$_3$.OEt$_2$ (0.034 eq). After stirring for 1 h at 0° C., the mixture is warmed to RT for 30 min and then conc in vacuo at 15 mmHg for 1 h. The resultant acyloxymethyl carbonochloridates are placed under 150 mmHg vacuum overnight and then are used without further purification.

General Procedure C: Synthesis of Carbamates (8)

A slurry of (S)-5-Aminomethyl-3-[4-(1,1-dioxo-hexahydro-1λ⁶-thiopyran-4-yl)-3-fluoro-phenyl]-oxazolidin-2-one (2) (1 eq) and CH$_2$Cl$_2$ is cooled to 0° C. Diisopropylethyl amine (2 eq) is added dropwise, followed by the addition of the appropriate acyloxymethyl carbonochloridate (7) (1.14 eq) in CH$_2$Cl$_2$. The mixture is stirred at 0° C. for 30-45 min and then warmed to RT. Upon completion of the reaction, water is added and the phases are separated. The organic layer is washed with water, 1 N HCl, brine, dried over Na$_2$SO$_4$, and conc in vacuo. Purification is achieved by silica gel chromatography.

General Procedure D: Synthesis of Prodrugs (9)

To a solution of the appropriate carbamate (8) (1 eq) in $CH_2Cl_2$ is added triethylamine (2 eq), 4-dimethylaminopyridine (0.1 eq), and acetic anhydride (20 eq). The mixture is stirred at RT overnight. Water is added and the phases are separated. The organic layer is washed with sat $NaHCO_3$, water, brine, dried over $Na_2SO_4$, and conc in vacuo. After purification by silica gel chromatography, the product is re-dissolved in $CH_2Cl_2$ and washed three times with sat $NaHCO_3$, brine, dried over $Na_2SO_4$ and conc in vacuo to afford the desired product.

Example 1

Preparation of ({[acetyl({(5R)-3-[4-(1,1-dioxidotetrahydro-2H-thiopyran4-yl)-3-fluorophenyl]-2-oxo-1, 3oxazolidin-5-yl}-methyl)amino] carbonyl}oxy) methylacetate Step 1: Preparation of Carbonothioic acid, O-(chloromethyl) S-ethyl ester To a stirred solution of chloromethyl chloroformate (3.5 mL, 38.7 mmol) in dry ether (70 mL) cooled to 0° C. is added dropwise a solution of ethane thiol (2.8 mL, 38.7 mmol) and triethylamine (5.4 mL, 38.7 mmol) in ether (15 mL) over 45 min. Stirred at 0° C. for 30 min and then at RT overnight. The reaction mixture filtered and the filtrate is concentrated. The resulting oil is distilled (30 torr, 85-90° C.) to afford 4.26 g (27.6 mmol, 72%) of the desired thioester. $^1$H NMR ($CDCl_3$) δ 5.79 (s, 2H), 2.95 (q, J=7 Hz, 2H), 1.38 (t, J=7 Hz, 2H).

Step 2: Preparation of carbonothioic acid, S-ethyl O-(iodomethyl) ester

To a stirred solution of the thioester from Step 1 (2.6 g, 16.9 mmol) in acetone (22 mL) is added sodium iodide (5.08 g 33.9 mmol) and sodium hydrogen carbonate (142.4 mg, 1.69 mmol). The reaction mixture is heated at 40° C. for 4 h. The cooled reaction mixture is filtered and the filter cake is washed with acetone and ether. The filtrate is concentrated. The resulting residue is partitioned between cold pentane (50 mL) and cold water (20 mL). The phases are separated. The organic phase is washed successively with a cold solution of 5% aqueous $NaHCO_3$ (20 mL), 10% aqueous $Na_2SO_3$ (10 mL), water (10 mL), dried ($MgSO_4$), filtered and concentrated to afford 3.86 g (15.6 mmol, 93%) of the desired iodide as a pale yellow oil. $^1$H NMR ($CDCl_3$) δ 6.01 (s, 2H), 2.93 (q, J=7 Hz, 2H), 1.34 (t, J=7 Hz, 3H).

Step 3: Preparation of carbonothioic acid, O-[(acetyloxy) methyl] S-ethyl ester

To a stirred suspension of anhydrous sodium acetate (1.27 g, 15.60 mmol) in dry DMF (21 mL) cooled to 0° C. is added dropwise a solution of the iodide from Step 2 (3.84 g, 15.60 mmol) in DMF (3 ml) with 1 mL rinse. The reaction mixture is stirred at RT overnight and then filtered. The filter cake is washed with a small amount of DMF and ether. The filtrate is partitioned between ether (100 mL) and ice cold $H_2O$ (100 mL). The phases are separated. The aqueous phase is extracted with ether (2×40 mL). The combined organics are washed successively with 5% aqueous $NaHCO_3$ (50 mL), $H_2O$ (50 mL), 0.1 N HCl (50 mL), $H_2O$ (2×50 mL), dried ($MgSO_4$), filtered and concentrated. The resulting liquid is purified on a Biotage 40 S column using 100% hexane to 2% ethyl acetate in hexane as the eluent to afford 1.52 g (8.54 mmol, 55%) of the desired product. $^1$H NMR ($CDCl_3$) δ 5.81 (s, 2H), 2.92 (q, J=10 Hz, 2H), 2.14 (s, 3H), 1.35 (t, J=10 Hz, 3H).

Step 4: Preparation of carbonochloridic acid, (acetyloxy) methyl ester

To the thioester from Step 3 (2.50 g, 14.0 mmol) cooled to 0° C. is added sulfuryl chloride (1.5 mL, 18.25 mmol) over 2 min. The reaction mixture is stirred at 0° C. for 30 min then at RT for 2.5 h. The reaction mixture is concentrated and then dried on house vacuum overnight to afford 2.4 g of the desired crude product, which is used without further purification. $^1$H NMR ($CDCl_3$) δ 5.83 (s, 2H), 2.19 (s, 3H);

Step 5: Preparation of ({[({(5S)-3-[4-(1,1-dioxidotetrahydro-2H-thiopyran-4-yl)-3-fluorophenyl]-2-oxo-1,3-oxazolidin-5-yl} methyl)amino]carbonyl}oxy)methyl acetate

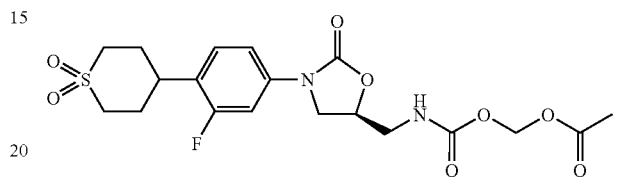

To a stirred suspension of the 4-{4-[(5S)-5-(aminomethyl)-2-oxo-1,3-oxazolidin-3-yl]-2-fluorophenyl}tetrahydro-1λ$^6$-thiopyran-1,1(2H)-dione (4.68 g, 13.74 mmol) prepared according to the PCT international publication WO 97/09328 in $CH_2Cl_2$ (100 mL) cooled to 0° C. is added diisopropylethylamine (4.8 ml, 27.48 mmol) followed by a solution of 2.4 g (1.5 7 mmol) of the acid chloride (from Step 4) in $CH_2Cl_2$ (10 mL) with a 2 mL rinse. The reaction mixture is stirred at 0° C. fro 30 min then at RT for 3 h. The reaction mixture is partitioned between $CH_2Cl_2$ (300 mL) and $H_2O$ (200 mL). The phases are separated. The organics are washed with 1N HCl (100 mL), brine (100 mL), dried ($MgSO_4$), filtered and concentrated. The residue is dissolved in $CH_2Cl_2$, absorbed onto silca gel and purified on a Biotage 40M with a SIM using 2% $CH_3OH$ in $CH_2Cl_2$ as the eluent to afford 5.32 g (11.6 mmol, 85%) of the desired carbamate as a white foam. $^1$H NMR (DMSO) δ 7.96 (t, J=6 Hz, 1H), 7.48 (dd, J=14, 2 Hz, 1H), 7.38 (t, J=9 Hz, 1H), 7.24 (dd, J=9, 2 Hz, 1H), 5.61(s, 2H), 4.74 (m, 1H), 4.12 (t, J=9 Hz, 1H), 3.76 (dd, J=9, 7 Hz, 1H), 3.38 (m, 4 H), 3.16 (m, 1H), 3.11 (m, 2H), 2.13 (m, 2H), 2.06 (m, 1H), 2.01 (s, 3H); $^{13}$C NMR (DMSO-d$_6$) δ 169.3, 160.6, 158 (d, J=246 Hz), 154.8, 153.8, 138.3 (d, J=8 Hz), 128.1, 125.2 (d, J=11 Hz), 113.7, 105.2 (d, J=26 Hz), 79.3, 71.7, 54.8, 50.3, 46.8, 43.1, 33.3, 29.8, 20.4; IR (diffuse reflectance) 2415, 2351, 2328, 1921, 1916, 1753, 1744, 1515, 1411, 1292, 1247, 1223, 1121, 1010, 983 cm$^{-1}$. % Water (KF titration): 1.08. $[α]^{25}{}_D$=–36° (c 0.91, DMSO). Anal. Calcd for $C_{19}H_{23}FN_2O_8S$ plus 1.08% $H_2O$: C, 49.24; H, 5.12; N, 6.04; S, 6.85. Found: C, 49.05; H, 5.21; N, 5.81; S, 6.85.

Step 6: Preparation of ({[acetyl({(5R)-3-[4-(1,1-dioxidotetrahydro-2H-thiopyran4-yl)-3-fluorophenyl]-2-oxo-1,3oxazolidin-5-yl}-methyl)amino] carbonyl}oxy)methyl-acetate

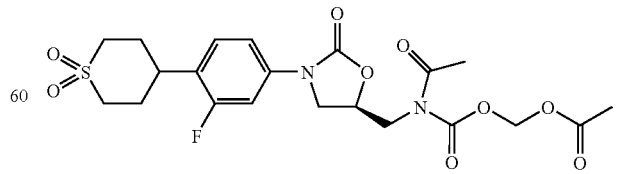

To a stirred solution of the carbamate (from Step 5) (2.64 g, 5.76 mmol) in $CH_2Cl_2$ (60 mL) is added triethylamine (1.6 mL, 11.52 mmol) followed by DMAP (17.5 mg) and acetic anhydride (6.5 mL, 69.15 mmol). The reaction mixture is stirred at RT for 18 h and then additional acetic anhydride (4 mL, 42.4 mmol) is added. The reaction mixture is stirred for an additional 24 h then partitioned between CH$_2$Cl$_2$ (200 mL) and H$_2$O (100 mL). The phases are separated. The organic phase is washed successively with saturated aqueous NaHCO$_3$ (75 mL), H$_2$O (75 mL), brine (75 mL), dried (MgSO$_4$), filtered and concentrated. The resulting residue is dissolved in CH$_2$Cl$_2$, absorbed onto silica gel and purified on a Biotage 40 M with a SIM using 1% CH$_3$OH in CH$_2$Cl$_2$ as the eluent to afford 2.24 g (4.48 mmol, 78%) of the desired product. $^1$H NMR (DMSO) δ 7.43 (dd, J=14, 2 Hz, 1H), 7.38 (t, J=9 Hz, 1H), 7.28 (dd, J=9, 2 Hz, 1H), 5.72 (s, 2H), 4.77 (m, 1H), 4.13 (dd, J=18, 9 Hz, 1H), 4.07 (d, J=9 Hz, 1H), 3.89 (dd, J=15, 4 Hz, 1H), 3.80 (dd, J=15, 6 Hz, 1H), 3.37 (m, 3H), 3.12 (m, 1H), 3.09 (m, 2H), 2.45 (s, 3H), 2.14 (m, 2H), 2.10 (s, 3H), 2.06 (m, 2H); IR (diffuse reflectance) 1763 (s), 1710, 1694, 1515, 1411, 1372, 1367, 1335, 1293, 1244, 1224, 1203, 1163, 1122, 1020 cm$^{-1}$ Anal. Calcd for C$_2$, H$_{25}$FN$_2$O$_9$S: C, 50.40; H, 5.03; N, 5.60; S, 6.41. Found: C, 50.22; H, 5.15; N, 5.49; S, 6.26.

Example 2

Preparation of (R)-propionic acid (acetyl-{3-[4-(1,1-dioxo-hexahydro-1λ$^6$-thiopyran-4-yl)-3-fluoro-phenyl]-2-oxo-oxazolidin-5-yl methyl}-carbamoyloxy)-methyl ester (9b)

Step 1: Preparation of propionic acid ethylsulfanylcarbonyloxymethyl ester (6b)

Following general procedure A, propionic acid, water (8 mL) and O-iodomethyl S-ethyl carbonothioate (5) (720 mg, 2.93 mmol) in dichloromethane (8 mL) gave the titled product in quantitative yield (562.5 mg, 2.93 mmol). $^1$H NMR (400 MHz, CDCl$_3$): δ 5.81 (s, 2H), 2.89 (q, 2H), 2.40 (q, 2H), 1.33 (t, 3H), 1.16 (t, 3H).

Step 2: Preparation of propanoyloxymethyl carbonochloridate (7b). Following general procedure B, propionic acid ethylsulfanylcarbonyloxymethyl ester (6b) (676.9 mg, 3.52 mmol) gave the titled product in quantitative yield (586.5 mg, 3.52 mmol). $^1$H NMR (400 MHz, CDCl$_3$): δ 5.83 (s, 2H), 2.45 (q, 2H), 1.90 (t, 3H).

Step 3: Preparation of (S)-propionic acid 3-[4-(1,1-dioxo-hexahydro-1λ$^6$-thiopyran-4-yl)-3-fluoro-phenyl]-2-oxo-oxazolidin-5-ylmethylcarbamoyloxymethyl ester (8b)

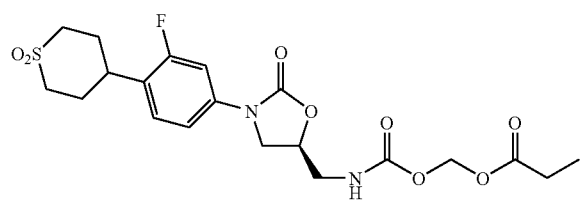

Following general procedure C, (S)-5-aminomethyl-3-[4-(1,1-dioxo-hexahydro-1λ6-thiopyran-4-yl)-3-fluoro-phenyl]-oxazolidin-2-one (2) (500 mg, 1.5 mmol), dichloromethane (14 mL) and propanoyloxymethyl carbonochloridate (7b) gave the titled product in 75% yield (520.9 mg, 1.10 mmol). $^1$H NMR (400 MHz, CDCl$_3$): δ 7.48 (dd, 1H), 7.24 (t, 1H), 7.16 (dd, 1H), 5.74 (q, 2H), 5.28 (t, 1H), 3.12-3.18 (m, 4.83 (m, 1H), 4.05 (t, 1H), 3.79 (dd, 1H), 3.67 (ddd, 1H), 3.56 (dt, 1H), 3.12-3.18(m, 4H), 3.10 (dt, 1H), 2.32-2.46 (m, 4H), 2.17-2.20 (m, 2H), 1.12 (t, 3H). MS-APCI (m/z+): 473 (M+H).

Step 4: Preparation of (R)-propionic acid (acetyl-{3-[4-(1,1-dioxo-hexahydro-1λ$^6$-thiopyran-4-yl)-3-fluoro-phenyl]-2-oxo-oxazolidin-5-ylmethyl}-carbamoyloxy)-methyl ester (9b)

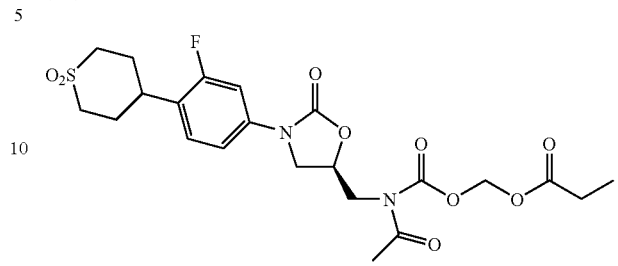

Following general procedure D, (S)-propionic acid 3-[4-(1,1-dioxo-hexahydro-1λ$^6$-thiopyran-4-yl)-3-fluoro-phenyl]-2-oxo-oxazolidin-5-ylmethyl-carbamoyloxymethyl ester (8b) (467.1 mg, 0.99 mmol) in dichloromethane (9.8 mL) gave the titled product in 88% yield (446.1 mg, 0.87 mmol). $^1$H NMR (400 MHz, CDCl$_3$): δ 7.48 (dd, 1H), 7.23 (t, 1H), 7.15 (dd, 1H), 5.88 (s, 2H), 4.79-4.86 (m, 1H), 4.20 (dd, 1H), 4.08 (t, 1H), 4.03 (dd, 1H),3.68 (dd, 1H), 3.13-3.19 (m, 4H), 3.10 (dt, 1H), 2.58 (s, 3H), 2.35-2.49 (m, 4H), 2.17-2.22 (m, 2H), 1.17 (t, 3H). MS-APCI (m/z+): 515 (M+H).

Example 3

Preparation of (R)-isobutyric acid (acetyl-{3-[4-(1,1-dioxo-hexahydro-1λ$^6$-thiopyran-4-yl)-3-fluoro-phenyl]-2-oxo-oxazolidin-5-ylmethyl}-carbamoyloxy)-methyl ester (9c)

Step 1: Preparation of isobutyric acid ethylsulfanylcarbonyloxymethyl ester (6c)

Following general procedure A, isobutyric acid, water (8 mL) and thiocarbonic acid O-iodomethyl S-ethyl carbonothioate (5) (720.0 mg, 2.93 mmol) in dichloromethane (8 mL) gave the titled product in quantitative yield (603.5 mg, 2.93 mmol). $^1$H NMR (400 MHz, CDCl$_3$): δ 5.81 (s, 2H), 2.90 (q, 2H), 2.60 (sept, 1H), 2.33 (t, 3H), 1.19 (d, 6H).

Step 2; Preparation of isobutyroyloxymethyl carbonochloridate (7c)

Following general procedure B, isobutyric acid ethylsulfanylcarbonyloxymethyl ester (6c) (603.5 mg, 2.93 mmol) gave the titled product in 39% yield (207.0 mg, 1.15 mmol). $^1$H NMR (400 MHz, CDCl$_3$): δ 5.83 (s, 2H), 2.65 (sept, 1H), 1.22 (d, 6H).

Step 3: Preparation of (S)-isobutyric acid 3-[4-(1,1-dioxo-hexahydro-1λ$^6$-thiopyran-4-yl)-3-fluoro-phenyl]-2-oxo-oxazolidin-5-ylmethylcarbamoyloxymethyl ester (8c)

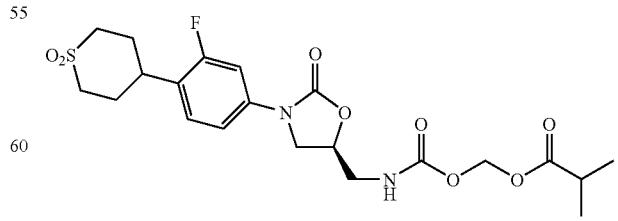

Following general procedure C, (S)-5-aminomethyl-3-[4-(1,1-dioxo-hexahydro-1λ$^6$-thiopyran-4-yl)-3-fluoro-phenyl]-oxazolidin-2-one (2) (344.1 mg, 1.00 mmol), dichloromethane (9 mL) and isobutyroyloxymethyl carbonochloridate (7c) gave the titled product in 91% yield (446.3 mg, 0.92 mmol). $^1$H NMR (400 MHz, CDCl$_3$): δ 7.48 (dd, 1H), 7.23 (t, 1H), 7.16 (dd, 1H), 5.73 (q, 2H), 5.28 (t, 1H), 4.80 (sept, 1H), 4.05 (t, 1H), 3.79 (dd, 1H), 3.67 (ddd, 1H), 3.57 (dt, 1H), 3.12-3.19 (m, 4H), 3.09 (dt, 1H), 2.55 (sept, 1H), 2.34-2.46 (m, 2H), 2.15-2.22 (m, 2H), 1.14 (dd, 6H). MS-APCI (m/z+): 487 (M+H).

Step 4: Preparation of (R)-Isobutyric acid (acetyl-{3-[4-(1, 1-dioxo-hexahydro-1λ$^6$-thiopyran-4-yl)-3-fluoro-phenyl]-2-oxo-oxazolidin-5-ylmethyl}-carbamoyloxy)-methyl ester (9c)

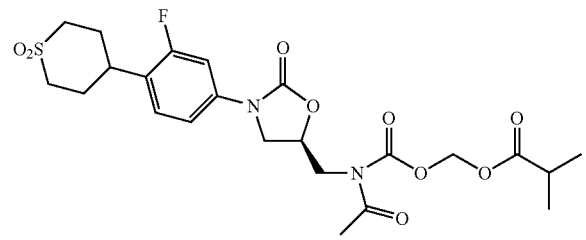

Following general procedure D, (S)-isobutyric acid 3-[4-(1,1-dioxo-hexahydro-1λ$^6$-thiopyran-4-yl)-3-fluoro-phenyl]-2-oxo-oxazolidin-5-ylmethylcarbamoyloxymethyl ester (8c) (384.2 mg, 0.79 mmol) in dichloromethane (8 mL) gave the titled product in 75% yield (311.5 mg, 0.59 mmol). $^1$H NMR (400 MHz, CDCl$_3$): δ 7.48 (dd, 1H), 7.23 (t, 1H), 7.15 (dd, 1H), 5.88 (s, 2H), 4.79-4.85 (m, 1H), 4.20 (dd, 1H), 4.07 (t, 1H), 4.02 (dd, 1H), 3.69 (dd, 1H), 3.13-3.19 (m, 4H), 3.10 (dt, 1H), 2.66 (sept, 1H), 2.57 (s, 3H), 2.35-2.46 (m, 2H), 2.18-2.22 (m, 2H),1.20 (d, 6H). MS-APCI (m/z+): 529 (M+H).

Example 4

Preparation of (R)-3-methyl-butyric acid (acetyl-{3-[4-(1,1-dioxo-hexahydro-1λ$^6$-thiopyran-4-yl)-3-fluoro-phenyl]-2-oxo-oxazolidin-5-ylmethyl}-carbamoyloxy)-methyl ester (9d)

Step 1: Preparation of 3-methyl-butyric acid ethylsulfanylcarbonyloxymethyl ester (6d). Following general procedure A, 3-methyl butyric acid in water (8 mL) and O-iodomethyl S-ethyl carbonothioate (5) (720.0 mg, 2.93 mmol) in dichloromethane (8 mL) gave the titled product in quantitative yield (644.6 mg, 2.93 mmol). $^1$H NMR (400 MHz, CDCl$_3$): δ 5.81 (s, 2H), 2.89 (q, 2H), 2.25 (d, 2H), 2.12 (sept, 1H),133 (t, 3H), 0.96 (d, 6H).

Step 2: Preparation of 3-methyl-butyroxymethyl carbonochloridate (7d)

Following general procedure B, 3-methyl-butyric acid ethylsulfanylcarbonyloxymethyl ester (6d) (644.6 mg, 2.93 mmol) gave the titled product in 87% yield (492.7 mg, 2.53 mmol). $^1$H NMR (400 MHz, CDCl$_3$): δ 5.86 (s, 2H), 2.29 (d, 2H), 2.13 (sept, 1H), 0.98 (d, 6H).

Step 3: Preparation of (S)-3-methyl-butyric acid 3-[4-(1,1-dioxo-hexahydro-1λ$^6$-thiopyran-4-yl)-3-fluoro-phenyl]-2-oxo-oxazolidin-5-ylmethylcarbamoyloxymethyl ester (8d)

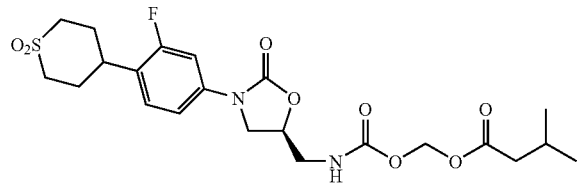

Following general procedure C, (S)-5-aminomethyl-3-[4-(1,1-dioxo-hexahydro-1λ$^6$-thiopyran-4-yl)-3-fluoro-phenyl]-oxazolidin-2-one (2) (760.0 mg, 2.2 mmol) in dichloromethane (21 mL) and 3-methyl-butyroxymethyl carbonochloridate (7d) gave the titled product in 93% yield (1030.0 mg, 2.06 mmol). $^1$H NMR (400 MHz, CDCl$_3$): δ 7.47 (dd, 1H), 7.23 (t, 1H), 7.16 (dd, 1H), 5.73 (q, 2H), 5.37 (t, 1H) 4.76-4.82 (m, 1H), 4.05 (t, 1H), 3.78 (dd, 1H), 3.67 (ddd, 1H), 3.55 (dt, 1H), 3.12-3.19 (m, 4H), 3.09 (dt, 1H), 2.34-2.45 (m, 2H), 2.14-2.21 (m, 2H), 2.07 (sept, 1H), 0.92 (dd, 6H). MS-APCI (m/z+): 501 (M+H).

Step 4: Preparation of (R)-3-methyl-butyric acid (acetyl-{3-[4-(1,1-dioxo-hexahydro-1λ$^6$-thiopyran-4-yl)-3-fluoro-phenyl]-2-oxo-oxazolidin-5-ylmethyl}-carbamoyloxy)-methyl ester (9d)

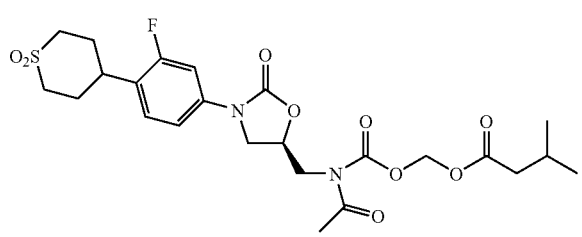

Following General Procedure D with (S)-3-methyl-butyric acid 3-[4-(1,1-dioxo-hexahydro-1λ$^6$-thiopyran-4-yl)-3-fluoro-phenyl]-2-oxo-oxazolidin-5-ylmethylcarbamoyloxymethyl ester (8d) (859.5 mg, 1.72 mmol) in dichloromethane (17 mL), the titled product is afforded in 86% yield (798.9 mg, 1.47 mmol). $^1$H NMR (400 MHz, CDCl$_3$): δ 7.48 (dd, 1H), 7.23 (t, 1H), 7.15 (dd, 1H), 5.87 (s, 2H), 4.79-4.86 (m, 1H), 4.20 (dd, 1H), 4.07 (t, 1H), 4.03 (dd, 1H), 3.69 (dd, 1H), 3.15-3.19 (m, 4H), 3.10 (dt, 1H), 2.57 (s, 3H), 2.35-2.44 (m, 2H), 2.31 (d, 2H),), 2.16-2.23 (m, 2H), 2.12 (sept, 1H), 0.96 (t, 6H). MS-APCI (m/z+): 543 (M+H).

Example 5

Preparation of (R)-butyric acid (acetyl-{3-[4-(1,1-dioxo-hexahydro-1λ$^6$-thiopyran-4-yl)-3-fluoro-phenyl]-2-oxo-oxazolidin-5-ylmethyl}-carbamoyloxy)-methyl ester (9e)

Step 1: Preparation of Thiocarbonic acid O-butoxymethyl ester S-ethyl ester (6e)

Following General Procedure A, butyric acid, water (8 mL) and O-iodomethyl S-ethyl carbonothioate (5) (720.0 mg, 2.93 mmol) in dichloromethane (8 mL) gave the titled product in quantitative yield (603.5 mg, 2.93 mmol). $^1$H NMR (400 MHz, CDCl$_3$): δ 5.81 (s, 2H), 2.89 (q, 2H), 2.35 (t, 2H), 1.67 (q, 2H), 1.33 (t, 2H), 0.96 (t, 2H).

Step 2: Preparation of butyroyloxymethyl carbonochloridate (7e).

Following General Procedure B with thiocarbonic acid O-butoxymethyl ester S-ethyl ester (6e) (605.8 mg, 2.94 mmol), the titled product is afforded in 56% yield (296.3 mg, 1.64 mmol). ¹H NMR (400 MHz, CDCl₃): δ 5.83 (s, 2H), 2.40 (t, 2H), 1.70 (sept, 2H), 0.98 (t, 3H).

Step 3: Preparation of (S)-butyric acid 3-[4-(1,1-dioxo-hexahydro-1λ⁶-thiopyran-4-yl)-3-fluoro-phenyl]-2-oxo-oxazolidin-5-ylmethylcarbamoyloxymethyl ester (8e)

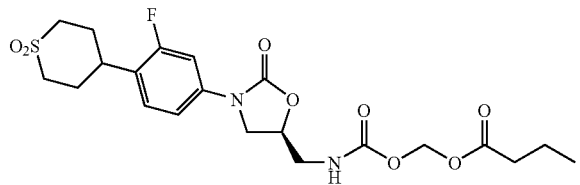

Following general procedure C, (S)-5-aminomethyl-3-[4-(1,1-dioxo-hexahydro-1λ⁶-thiopyran-4-yl)-3-fluoro-phenyl]-oxazolidin-2-one (2) (492.7 mg, 1.44 mmol) in dichloromethane (13 mL) and butyroyloxymethyl carbonochloridate (7e) gave the titled product in 73% yield (512.1 mg, 1.05 mmol). ¹H NMR (400 MHz, CDCl₃): δ 7.48 (dd, 1H), 7.23 (t, 1H), 7.16 (dd, 1H), 5.73 (q, 2H), 5.29 (t, 1H), 4.80 (sept, 1H), 4.05 (t, 1H), 3.79 (dd, 1H), 3.67 (ddd, 1H), 3.56 (dt, 1H), 3.13-3.19 (m, 4H), 3.09 (dt, 1H), 2.35-2.47 (m, 2H), 2.31 (t, 2H), 2.14-2.22 (m, 2H), 1.63 (q, 2H), 0.93 (t, 3H). MS-APCI (m/z+): 487 (M+H).

Step 4: Preparation of (R)-butyric acid (acetyl-{3-[4-(1,1-dioxo-hexahydro-1λ⁶-thiopyran-4-yl)-3-fluoro-phenyl]-2-oxo-oxazolidin-5-ylmethyl}-carbamoyloxy)-methyl ester (9e)

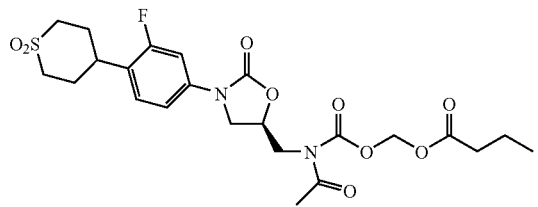

Following General Procedure D with (S)-butyric acid 3-[4-(1,1-dioxo-hexahydro-1λ⁶-thiopyran-4-yl)-3-fluoro-phenyl]-2-oxo-oxazolidin-5-ylmethylcarbamoyloxymethyl ester (8e) (406.1 mg, 0.84 mmol) in dichloromethane (8.3 mL), the titled product is afforded in 91% yield (402.9 mg, 0.76 mmol). ¹H NMR (400 MHz, CDCl₃): δ 7.48 (dd, 1H), 7.23 (t, 1H), 7.15 (dd, 1H), 5.87 (s, 2H), 4.79-4.84 (m, 1H), 4.20 (dd, 1H), 4.07 (t, 1H), 4.03 (ddd, 1H), 3.68 (dd, 1H), 3.13-319 (m, 4H), 3.10 (dt, 1H), 2.57 (s, 3H), 2.35-2.46 (m, 2H), 2.41 (t, 2H), 2.14-2.22 (m, 2H), 1.68 (sext, 2H), 0.96 (t, 3H). MS-APCI (m/z+): 529 (M+H).

Example 6

Preparation of (R)-2,2-dimethyl-propionic acid (acetyl-{3-[4-(1,1-dioxo-hexahydro-1λ⁶-thiopyran-4-yl)-3-fluoro-phenyl]-2-oxo-oxazolidin-5-ylmethyl}-carbamoyloxy)-methyl ester (9f)

Step 1: Preparation of 2,2-dimethyl-propionic acid ethylsulfanylcarbonyloxymethyl ester (6f)

Following General Procedure A, 2,2-dimethyl-propionic acid, water (8 mL) and O-iodomethyl S-ethyl carbonothioate (5) (720.0 mg, 2.93 mmol) in dichloromethane (8 mL) gave the titled product in quantitative yield (644.6 mg, 2.93 mmol). ¹H NMR (400 MHz, CDCl₃): δ 5.81 (s, 2H), 2.89 (q, 2H), 1.32 (t, 3H), 1.22 (s, 9H).

Step 2: Preparation of 2,2-dimethyl-propanoyloxymethyl carbonochloridate (7f)

Following General Procedure B with 2,2-dimethyl-propionic acid ethylsulfanylcarbonyloxymethyl ester (6f) (644.6 mg, 2.93 mmol), the titled product is afforded in 54% yield (305.4 mg, 1.57 mmol). ¹H NMR (400 MHz, CDCl₃): δ 5.83 (s, 2H), 1.25 (s, 9H).

Step 3: Preparation of (S)-2,2-dimethyl-propionic acid 3-[4-(1,1-dioxo-hexahydro-1λ⁶-thiopyran-4-yl)-3-fluoro-phenyl]-2-oxo-oxazolidin-5-ylmethylcarbamoyloxymethyl ester (8f)

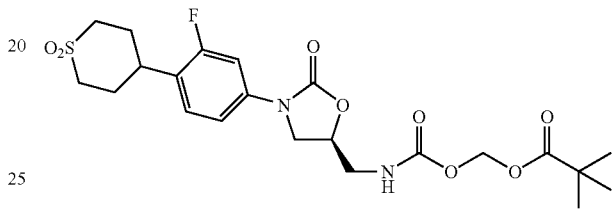

Following general procedure C, (S)-5-aminomethyl-3-[4-(1,1-dioxo-hexahydro-1λ⁶-thiopyran-4-yl)-3-fluoro-phenyl]-oxazolidin-2-one (2) (472.0 mg, 1.38 mmol) in dichloromethane (13 mL) and 2,2-dimethyl-propanoyloxymethyl carbonochloridate (7f) gave the titled product in 85% yield (585.6 mg, 1.17 mmol).

¹H NMR (400 MHz, CDCl₃): δ 7.47 (dd, 1H), 7.22 (t, 1H), 7.15 (dd, 1H), 5.72 (q, 2H), 5.39 (t, 1H), 4.75-4.82 (m, 1H), 4.05 (t, 1H), 3.79 (dd, 1H), 3.66 (ddd, 1H), 3.57 (dt, 1H), 3.12-3.19 (m, 4H), 3.09 (dt, 1H), 2.34-2.45 (m, 2H), 2.16-2.20 (m, 2H), 1.16 (s, 9H). MS-APCI (m/z+): 501 (M+H).

Step 4: Preparation of (R)-2,2-dmethyl-propionic acid (acetyl-{3-[4-(1,1-dioxo-hexahydro-1λ⁶-thiopyran-4-yl)-3-fluoro-phenyl]-2-oxo-oxazolidin-5-ylmethyl}-carbamoyloxy)-methyl ester (9f)

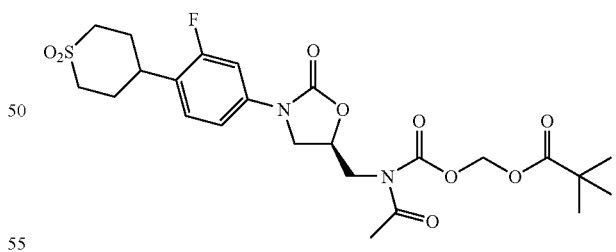

Following General Procedure D with (S)-2,2-dimethyl-propionic acid 3-[4-(1,1-dioxo-hexahydro-1λ⁶-thiopyran-4-yl)-3-fluoro-phenyl]-2-oxo-oxazolidin-5-ylmethylcarbamoyloxymethyl ester (8f) (450.5 mg, 0.900 mmol) in dichloromethane (9 mL), the titled product is afforded in 86% yield (422.3 mg, 0.78 mmol). ¹H NMR (400 MHz, CDCl₃): δ 7.50 (dd, 1H), 7.23 (t, 1H), 7.15 (dd, 1H), 5.87 (s, 2H), 4.78-4.85 (m, 1H), 4.20 (dd, 1H), 4.07 (t, 1H), 4.01 (dd, 1H), 3.70 (dd, 1H), 3.13-3.19 (m, 4H), 3.09 (dt, 1H), 2.56 (s, 3H), 2.35-2.46 (m, 2H), 2.15-2.21 (m, 2H), 1.23 (s, 9H). MS-APCI (m/z+): 529 (M+H).

Example 7

Preparation of (R)-3,3-dimethyl-butyric acid (acetyl-{3-[4-(1,1-dioxo-hexahydro-1λ⁶-thiopyran-4-yl)-3-fluoro-phenyl]-2-oxo-oxazolidin-5-ylmethyl}-carbamoyloxy)-methyl ester (9 g)

Step 1: Preparation of 3,3-dimethyl-butyric acid ethylsulfanylcarbonyloxymethyl ester (6 g). Following General Procedure A, 3,3-dimethyl-butyric acid, water (5 mL) and O-iodomethyl S-ethyl carbonothioate (5) (488.2 mg, 1.98 mmol) in dichloromethane (5 mL) gave the titled product in quantitative yield (464.9 mg, 1.98 mmol). $^1$H NMR (400 MHz, CDCl$_3$): δ 5.80 (s, 2H), 2.89 (q, 2H), 2.25 (s, 2H), 1.32 (t, 2H), 1.03 (s, 9H).

Step 2: Preparation of 3,3-dimethyl-butyroxymethyl carbonochloridate (7 g)

Following General Procedure B with 3,3-dimethyl-butyric acid ethylsulfanylcarbonyloxymethyl ester (6 g) (488.2 mg, 1.98 mmol), the titled product is afforded in quantitative yield (464.9 mg, 1.98 mmol). $^1$H NMR (400 MHz, CDCl$_3$): δ 5.82 (s, 2H), 2.27 (s, 2H), 1.05 (s, 9H).

Step 3: Preparation of (S)-3,3-dimethyl-butyric acid 3-[4-(1,1-dioxo-hexahydro-1λ⁶-thiopyran-4-yl)-3-fluoro-phenyl]-2-oxo-oxazolidin-5-ylmethylcarbamoyloxymethyl ester (8 g)

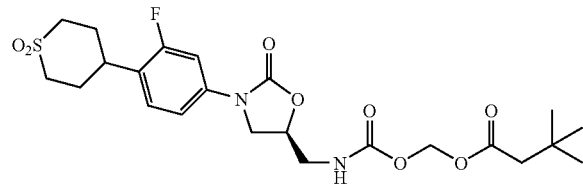

Following general procedure C, (S)-5-aminomethyl-3-[4-(1,1-dioxo-hexahydro-1λ⁶-thiopyran-4-yl)-3-fluoro-phenyl]-oxazolidin-2-one (2) (589.0 mg, 1.72 mmol) in dichloromethane (14 mL) and 3,3-dimethyl-butyroxymethyl carbonochloridate (7 g) gave the titled product in 46% yield (407.2 mg, 0.79 mmol). $^1$H NMR (400 MHz, CDCl$_3$): δ 7.48 (dd, 1H), 7.24 (t, 1H), 7.16 (dd, 1H), 5.73 (q, 2H), 5.26 (t, 1H), 4.75-4.82 (m, 1H), 4.05 (t, 1H), 3.78 (dd, 1H), 3.68 (ddd, 1H), 3.56 (dt, 1H), 3.13-3.19 (m, 4H), 3.10 (dt, 1H), 2.35-2.46 (m, 2H), 2.16-2.25 (m, 4H), 1.00 (s, 9H).

Step 4: Preparation of (R)-3,3-dimethyl-butyric acid (acetyl-{3-[4-(1,1-dioxo-hexahydro-1λ⁶-thiopyran-4-yl)-3-fluoro-phenyl]-2-oxo-oxazolidin-5-ylmethyl}-carbamoyloxy)-methyl ester (9 g)

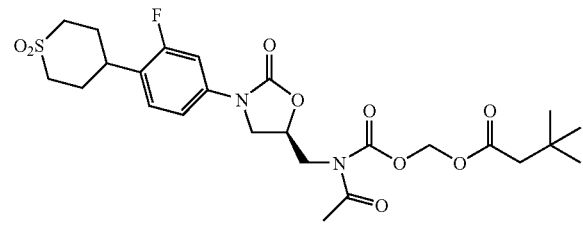

Following General Procedure D, (S)-3,3-dimethyl-butyric acid 3-[4-(1,1-dioxo-hexahydro-1λ⁶-thiopyran-4-yl)-3-fluoro-phenyl]-2-oxo-oxazolidin-5-ylmethylcarbamoyloxymethyl ester (8 g) (330.8 mg, 0.64 mmol) in dichloromethane (6.5 mL) gave the titled product in 90% yield (329.1 mg, 0.59 mmol). $^1$H NMR (400 MHz, CDCl$_3$): δ 7.48 (dd, 1H), 7.23 (t, 1H), 7.15 (dd, 1H), 5.86 (s, 2H), 4.78-4.85 (m, 1H), 4.20 (dd, 1H), 4.07 (t, 1H), 4.01 (dd, 1H), 3.69 (dd, 1H), 3.13-3.19 (m, 4H), 3.09 (dt, 1H), 2.57 (s, 3H), 2.34-2.48 (m, 2H), 2.30 (s, 2H), 2.14-2.22 (m, 2H), 1.03 (s, 9H). MS-APCI (m/z+): 577 (M+H).

Example 8

Preparation of (R)-cyclopropanecarboxylic acid (acetyl-{3-[4-(1,1-dioxo-hexahydro-1λ⁶-thiopyran-4-yl)-3-fluoro-phenyl]-oxazolidin-5-ylmethyl}-carbamoyloxy)-methyl ester (9 h)

Step 1: Preparation of cyclopropanecarboxylic acid ethylsulfanylcarbonyloxymethyl ester (6 h)

Following General Procedure A, cyclopropanecarboxylic acid, water (8 mL) and O-iodomethyl S-ethyl carbonothioate (5) (866.5 mg, 3.52 mmol) in dichloromethane (8 mL) gave the titled product in quantitative yield (719.2 mg, 3.52 mmol). $^1$H NMR (400 MHz, CDCl$_3$): δ 5.80 (s, 2H), 2.90 (q, 2H), 1.66 (tt, 1H), 1.33 (t, 3H), 1.07 (dt, 2H), 0.94 (dt, 2H).

Step 2: Preparation of cyclopropanecarbonoylmethyl carbonochloridate (7 h)

Following General Procedure B with cyclopropanecarboxylic acid ethylsulfanylcarbonyloxymethyl ester (6 h) (719.2 mg, 3.52 mmol), the titled product is afforded in quantitative yield (628.8 mg, 3.52 mmol). $^1$H NMR (400 MHz, CDCl$_3$): δ 5.82 (s, 2H), 1.66-1.71 (m, 1H), 1.10-1.14 (m, 2H), 0.98-1.03 (m, 2H).

Step 3: Preparation of (S)-cyclopropanecarboxylic acid 3-[4-(1,1-dioxo-hexahydro-1λ⁶-thiopyran-4-yl)-3-fluoro-phenyl]-2-oxo-oxazolidin-5-ylmethylcarbamoyloxymethyl ester (8 h)

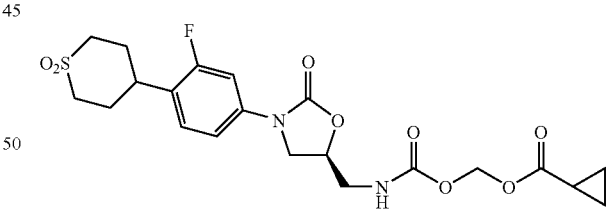

Following general procedure C, (S)-5-aminomethyl-3-[4-(1,1-dioxo-hexahydro-1λ⁶-thiopyran-4-yl)-3-fluoro-phenyl]-oxazolidin-2-one (500.0 mg, 1.46 mmol) (2) in dichloromethane (14 mL) and cyclopropanecarbonoylmethyl carbonochloridate (7 h) gave the titled product in 90% yield (637.4 mg, 1.32 mmol).

$^1$H NMR (400 MHz, CDCl$_3$): δ 7.48 (dd, 1H), 7.23 (t, 1H), 7.16 (dd, 1H), 5.72 (q, 2H), 5.33 (t, 1H), 4.77-4.83 (m, 1H), 4.05 (t, 1H), 3.79 (dd, 1H), 3.67 (ddd, 1H), 3.56 (dt, 1H), 3.12-3.18 (m, 4H), 3.09 (dt, 1H), 2.34-2.46 (m, 2H), 2.16-2.22 (m, 2H), 1.58-1.65 (m, 1H), 1.00-1.04 (m, 2H), 0.88-0.92 (m, 2H). MS-APCI (m/z+): 485 (M+H).

Step 4: Preparation of (R)-cyclopropanecarboxylic acid (acetyl-{3-[4-(1,1-dioxo-hexahydro-1λ⁶-thiopyran-4-yl)-3-fluoro-phenyl]-oxazolidin-5-ylmethyl}-carbamoyloxy)-methyl ester (9 h)

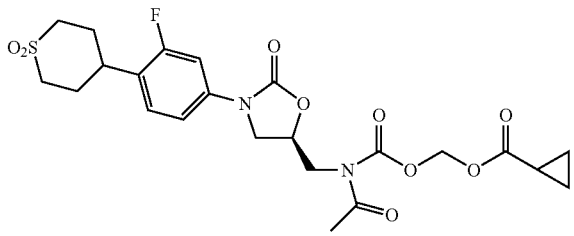

Following General Procedure D, (S)-cyclopropanecarboxylic acid 3-[4-(1,1-dioxo-hexahydro-1λ⁶-thiopyran-4-yl)-3-fluoro-phenyl]-2-oxo-oxazolidin-5-ylmethylcarbamoyloxymethyl ester (8 h) (535.8 mg, 1.11 mmol) in dichloromethane (11 mL) gave the titled product in 77% yield (445.6 mg, 0.85). $^1$H NMR (400 MHz, CDCl$_3$): δ 7.48 (dd, 1H), 7.23 (t, 1H), 7.16 (dd, 1H), 5.87 (q, 2H), 4.79-4.86 (m, 1H), 4.20 (dd, 1H), 4.07 (t, 1H), 4.02 (dd, 1H), 3.69 (dd, 1H), 3.12-3.18 (m, 4H), 3.09 (dt, 1H), 2.58 (s, 3H), 2.35-2.46 (m, 2H), 2.16-2.23 (m, 2H), 1.70 (ttt, 1H), 1.07-1.11 (m, 2H), 0.95-1.00 (m, 2H). MS-APCI (m/z+): 527 (M+H).

Example 9

Preparation of (R)-cyclopentanecarboxylic acid (acetyl-{3-[4-(1,1-dioxo-hexahydro-1λ⁶-thiopyran-4-yl)-3-fluoro-phenyl]-2-oxo-oxazolidin-5-ylmethyl}-carbamoyloxy)-methyl ester (9i)

Step 1: Preparation of cyclopentanecarboxylic acid ethylsulfanylcarbonyloxymethyl ester (6i)

Following General Procedure A, cyclopentanecarboxylic acid, water (8 mL) and O-iodomethyl S-ethyl carbonothioate (5) (866.5 mg, 3.52 mmol) in dichloromethane (8 mL) gave the titled product in quantitative yield (818.0 mg, 3.52 mmol). $^1$H NMR (400 MHz, CDCl$_3$): δ 5.81 (s, 2H), 2.80 (q, 2H), 2.79 (quint, 1H), 1.55-1.95 (m, 8H), 1.33 (t, 3H).

Step 2: Preparation of cyclopentanecarbonoylmethyl carbonochloridate (7i)

Following General Procedure B with cyclopentanecarboxylic acid ethylsulfanylcarbonyloxymethyl ester (6i) (818.0 mg, 3.52 mmol), the titled product is afforded in quantitative yield (727.6 mg, 3.52 mmol). $^1$H NMR (400 MHz, CDCl$_3$): δ 5.83 (s, 2H), 2.83 (quint, 1H), 1.56-1.98 (m, 8H).

Step 3: Preparation of (S)-cyclopentanecarboxylic acid 3-[4-(1,1-dioxo-hexahydro-1λ⁶-thiopyran-4-yl)-3-fluoro-phenyl]-2-oxo-oxazolidin-5-ylmethylcarbamoyloxymethyl ester (8i)

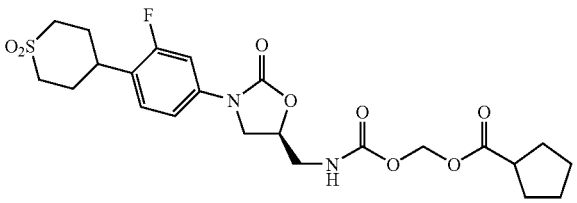

Following general procedure C, (S)-5-aminomethyl-3-[4-(1,1-dioxo-hexahydro-1λ⁶-thiopyran-4-yl)-3-fluoro-phenyl]-oxazolidin-2-one (2) (500.0 mg, 1.5 mmol) in dichloromethane (14 mL) and cyclopentanecarbonoylmethyl carbonochloridate (7i) gave the titled product in 86% yield (642.2 mg, 1.25 mmol). $^1$H NMR (400 MHz, CDCl$_3$): δ 7.48 (dd, 1H), 7.23 (t, 1H), 7.16 (dd, 1H), 5.73 (q, 2H), 5.31 (t, 1H), 4.76-4.82 (m, 1H), 4.05 (t, 1H), 3.79 (dd, 1H), 3.67 (ddd, 1H), 3.57 (dt, 1H), 3.12-3.18 (m, 4H), 3.09 (dt, 1H), 2.73 (quint, 1H), 2.34-2.45 (m, 2H), 2.16-2.21 (m, 2H), 1.52-1.88 (m, 8H).

Step 4: Preparation of (R)-cyclopentanecarboxylic acid (acetyl-{3-[4-(1,1-dioxo-hexahydro-1λ⁶-thiopyran-4-yl)-3-fluoro-phenyl]-2-oxo-oxazolidin-5-ylmethyl}-carbamoyloxy)-methyl ester (9i)

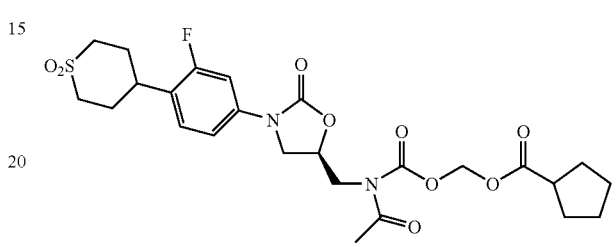

Following General Procedure D with (S)-cyclopentanecarboxylic acid 3-[4-(1,1-dioxo-hexahydro-1λ⁶-thiopyran-4-yl)-3-fluoro-phenyl]-2-oxo-oxazolidin-5-ylmethylcarbamoyloxymethyl ester (8i) (558.8 mg, 1.09 mmol) in dichloromethane (11 mL), the titled product is afforded in 88% yield (483.1 mg, 0.87 mmol). $^1$H NMR (400 MHz, CDCl$_3$): δ 7.48 (dd, 1H), 7.23 (t, 1H), 7.15 (dd, 1H), 5.87 (q, 2H), 4.79-4.86 (m, 1H), 4.20 (dd, 1H), 4.07 (t, 1H), 4.02 (dd, 1H), 3.69 (dd, 1H), 3.13-3.19 (m, 4H), 3.10 (dt, 1H), 2.83 (ttt, 1H), 2.57 (s, 3H), 2.35-2.47 (m, 2H), 2.15-2.23 (m, 2H), 1.88-1.98 (m, 2H), 1.75-1.86 (m, 2H), 1.65-1.74 (m, 2H), 1.56-1.64 (m, 2H). MS-APCI (m/z+): 555 (M+H).

Example 10

Preparation of (R)-cyclohexanecarboxylic acid (acetyl-{3-[4-(1,1-dioxo-hexahydro-1λ⁶-thiopyran-4-yl)-3-fluoro-phenyl]-2-oxo-oxazolidin-5-ylmethyl}-carbamoyloxy)-methyl ester (9j)

Step 1: Preparation of cyclohexanecarboxylic acid ethylsulfanylcarbonyloxymethyl ester (6j)

Following General Procedure A, cyclohexanecarboxylic acid, water (5 mL) and O-iodomethyl S-ethyl carbonothioate (5) (488.2 mg, 1.98 mmol) in dichloromethane (5 mL) gave the titled product in quantitative yield (488.7 mg, 1.98 mmol). $^1$H NMR (400 MHz, CDCl$_3$): δ 5.80 (s, 2H), 2.89 (q, 2H), 2.23-2.38 (m, 1H), 1.88-1.96 (m, 2H), 1.72-1.80 (m, 2H), 1.60-1.70 (m, 2H), 1.40 (m, 2H), 1.32 (t, 3H), 1.21-1.30 (m, 2H).

Step 2: Preparation of cyclohexanecarbonoylmethyl carbonochloridate (7j)

Following General Procedure B with cyclohexanecarboxylic acid ethylsulfanylcarbonyloxymethyl ester (6j) (488.2 mg, 1.98 mmol), the titled product is afforded in quantitative yield (488.7 mg, 1.98 mmol). $^1$H NMR (400 MHz, CDCl$_3$): δ 5.82 (s, 2H), 2.37 (qt, 1H), 1.90-1.98 (m, 2H), 1.72-1.81 (m2H), 1.60-1.78 (m, 2H), 1.41-1.53 (m, 2H), 1.22-1.36 (m, 2H).

Step 3: Preparation of (S)-cyclohexanecarboxylic acid 3-[4-(1,1-dioxo-hexahydro-1λ⁶-thiopyran-4-yl)-3-fluoro-phenyl]-2-oxo-oxazolidin-5-ylmethylcarbamoyloxymethyl ester (8j)

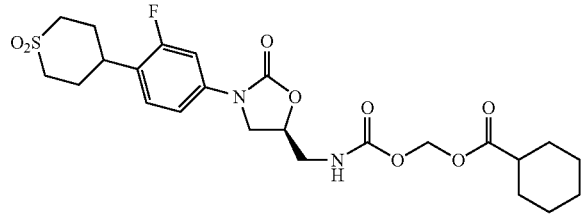

Following general procedure C, (S)-5-aminomethyl-3-[4-(1,1-dioxo-hexahydro-1λ⁶-thiopyran-4-yl)-3-fluoro-phenyl]-oxazolidin-2-one (2) (589.0 mg, 1.72 mmol) in dichloromethane (14 mL) and cyclohexanecarbonoylmethyl carbonochloridate (7j) gave the titled product in 80% yield (722.9 mg, 1.37 mmol). ¹H NMR (400 MHz, CDCl₃): δ 7.48 (dd, 1H), 7.23 (t, 1H), 7.16 (dd, 1H), 5.72 (q, 2H), 5.29 (t, 1H), 4.76-4.82 (m, 1H), 4.05 (t, 1H), 3.78 (dd, 1H), 3.64-3.70 (m, 1H 3.57 (dt, 1H), 3.13-3.19 (m, 4H), 3.09 (dt, 1H), 2.29-2.46 (m, 4H), 2.16-2.22 (m, 2H), 1.58-1.98 (m, 5H).

Step 4: Preparation of (R)-cyclohexanecarboxylic acid (acetyl-{3-[4-(1,1-dioxo-hexahydro-1λ⁶-thiopyran-4-yl)-3-fluoro-phenyl]-2-oxo-oxazolidin-5-ylmethyl}-carbamoyloxy)-methyl ester (9j)

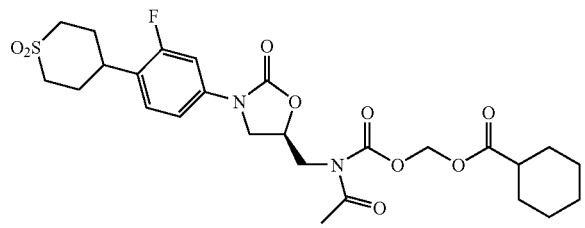

Following General Procedure D with (S)-cyclohexanecarboxylic acid 3-[4-(1,1-dioxo-hexahydro-1λ⁶-thiopyran4-yl)-3-fluoro-phenyl]-2-oxo-oxazolidin-5-ylmethylcarbamoyloxymethyl ester (8j) (507.4 mg, 0.96 mmol) in dichloromethane (9.8 mL), the titled product is afforded in 54% yield (298.5 mg, 0.52 mmol). ¹H NMR (400 MHz, CDCl₃): δ 7.48 (dd, 1H), 7.23 (t, 1H), 7.15 (dd, 1H), 5.87 (s, 2H), 4.78-4.85 (m, 1H), 4.20 (dd, 1H), 4.07 (t, 1H), 4.01 (dd, 1H), 3.67 (dd, 1H), 3.13-3.19 (m, 4H), 3.10 (dt, 1H), 2.57 (s, 3H), 2.35-2.46 (m, 3H), 2.15-2.23 (m, 2H), 1.90-1.96 (m, 2H), 1.72-1.78 (m, 2H), 1.63-1.66 (m, 1H), 1.40-1.50 (m, 2H), 1.19-1.34 (m, 3H). MS-APCI (m/z+): 569 (M+H).

Example 11

Preparation of (R)-benzoic acid (acetyl-{3-[4-(1,1-dioxo-hexahydro-1λ⁶-thiopyran-4-yl)-3-fluoro-phenyl]-2-oxo-oxazolidin-5-ylmethyl}-carbamoyloxy)-methyl ester (9k)

Step 1: Preparation of benzoic acid ethylsulfanylcarbonyloxymethyl ester (6k)

Following General Procedure A with benzoic acid, water (8 mL) and O-iodomethyl S-ethyl carbonothioate (5) (866.5 mg, 3.52 mmol) in dichloromethane (8 mL), the titled product is afforded in quantitative yield (846.1 mg, 3.52 mmol). ¹H NMR (400 MHz, CDCl₃): δ 8.08 (d, 2H), 7.90 (t, 1H), 7.46 (t, 2), 6.06 (s, 2H), 2.91 (q, 2H), 1.33 (t, 3H).

Step 2: Preparation of benzoyloxymethyl carbonochloridate (7k)

Following General Procedure B with benzoic acid ethylsulfanyloxymethyl ester (6k) (846.1 mg, 3.52 mmol), the titled product is afforded in quantitative yield (755.7 mg, 3.52 mmol). ¹H NMR (400 MHz, CDCl₃): δ 8.10 (d, 2H), 7.64 (t, 1H), 7.49 (t, 2H), 6.80 (s, 2H).

Step 3: Preparation of (S)-benzoic acid 3-[4-(1,1-dioxo-hexahydro-1λ⁶-thiopyran-4-yl)-3-fluoro-phenyl]-2-oxo-oxazolidin-5-ylmethylcarbamoyloxymethyl ester (8k)

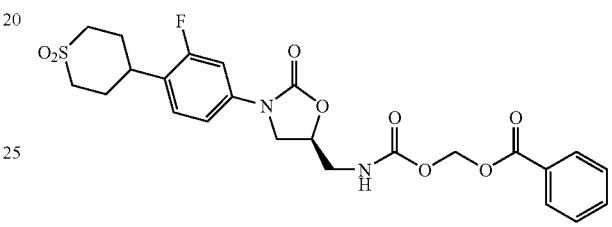

Following general procedure C, (S)-5-aminomethyl-3-[4-(1,1-dioxo-hexahydro-1λ⁶-thiopyran-4-yl)-3-fluoro-phenyl]-oxazolidin-2-one (2) (500.0 mg, 1.5 mmol) in dichloromethane (14 mL) and benzoyloxymethyl carbonochloridate (7k) gave the titled product in 98% yield (744.5 mg, 1.43 mmol). ¹H NMR (400 MHz, CDCl₃): δ 8.05 (d, 2H), 7.60 (t, 1H), 7.46 (q, 3H), 7.20 (t, 1H), 7.13 (dd, 1H), 5.98 (q, 2H), 5.36 (t, 1H), 4.77-4.83 (m, 1H), 4.05 (t, 1H), 3.80 (dd, 1H), 3.68 (ddd, 1H), 3.57 (dt, 1H), 3.12-3.19 (m, 4H), 3.08 (dt, 1H), 2.31-2.45 (m, 2H), 2.13-2.21 (m, 2H).

Step 4: Preparation of (R)-benzoic acid (acetyl-{3-[4-(1,1-dioxo-hexahydro-1λ⁶-thiopyran-4-yl)-3-fluoro-phenyl]-2-oxo-oxazolidin-5-yl methyl}-carbamoyloxy)-methyl ester (9k)

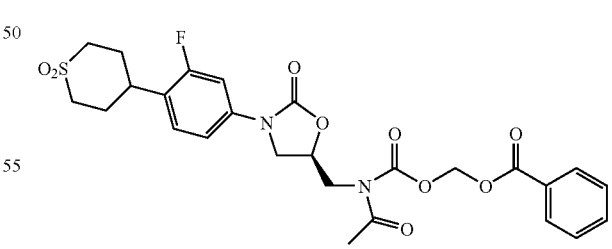

Following General Procedure D with (S)-propionic acid 3-[4-(1,1-dioxo-hexahydro-1λ⁶-thiopyran-4-yl)-3-fluoro-phenyl]-2-oxo-oxazolidin-5-ylmethylcarbamoyloxymethyl ester (8k) (604.6 mg, 1.18 mmol) in dichloromethane (12 mL), the titled product is afforded in 86% yield (564.7 mg, 1.12 mmol). ¹H NMR (400 MHz, CDCl₃): δ 8.09 (dd, 2H), 7.63 (tt, 1H), 7.44-7.50 (m, 3H), 7.20 (t, 1H), 7.12 (dd, 1H), 6.12 (q, 2H), 4.80-4.87 (m, 1H), 4.23 (dd, 1H), 4.07 (t, 1H), 4.03 (dd, 1H), 3.69 (dd, 1H), 3.12-3.18 (m, 4H), 3.09 (dt, 1H), 2.58 (s, 3H), 2.34-2.45 (m, 2H), 2.15-2.23 (m, 2H).

Example 12

Preparation of (R)-tetrahydro-pyran-4-carboxylic acid (acetyl-{3-[4-(1,1-dioxo-hexahydro-1$\lambda^6$-thiopyran-4-yl)-3-fluoro-phenyl]-2-oxo-oxazolidin-5-ylmethyl}-carbamoyloxy)-methyl ester (91)

Step 1: Preparation of tetrahydro-pyran-4-carboxylic acid ethylsulfanylcarbonyl-oxymethyl ester (61)

Following General Procedure A with tetrahydro-pyran-4-carboxylic acid, water (5 mL), O-iodomethyl S-ethyl carbonothioate (5) (488.2 mg, 1.98 mmol) in dichloromethane (5 mL), the titled product is afforded in quantitative yield (481.8 mg, 1.98 mmol). $^1$H NMR (400 MHz, CDCl$_3$): δ 5.82 (s, 2H), 3.96 (dt, 2H), 3.43 (td, 2H), 2.90 (q, 2H), 2.57-2.65 (m, 1H), 1.76-1.90 (m, 4H), 1.33 (t, 3H).

Step 2: Preparation of tetrahydro-pyran4-carbonoylmethy carbonochloridate (71)

Following General Procedure B with tetrahydro-pyran-4-carboxylic acid ethylsulfanylcarbonyloxymethyl ester (61) (488.2 mg, 1.98 mmol), the titled product is afforded in 98% yield (481.8 mg, 1.98 mmol). $^1$H NMR (400 MHz, CDCl$_3$): δ 5.85 (s, 2H), 3.98 (dt, 2H), 3.45 (td, 2H), 2.66 (tt, 1H), 1.76-1.91 (m, 4H).

Step 3: Preparation of (S)-tetrahydro-pyran-4-carboxylic acid 3-[4-(1,1-dioxo-hexahydro-1$\lambda^6$-thiopyran-4-yl)-3-fluoro-phenyl]-2-oxo-oxazolidin-5-ylmethylcarbamoyloxymethyl ester (81)

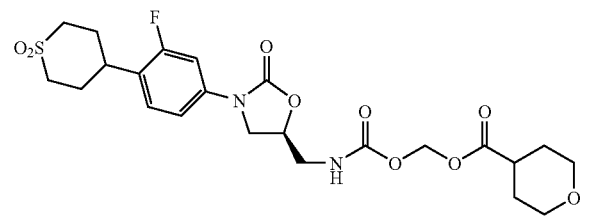

Following general procedure C, (S)-5-aminomethyl-3-[4-(1,1-dioxo-hexahydro-1$\lambda^6$-thiopyran-4-yl)-3-fluoro-phenyl]-oxazolidin-2-one (2) (579.0 mg, 1.69 mmol) in dichloromethane (14 mL) and tetrahydro-pyran4-carbonoylmethy carbonochloridate (71) gave the titled product in 80% yield (716.5 mg, 1.36 mmol). $^1$H NMR (400 MHz, CDCl$_3$): δ 7.48 (dd, 1H), 7.24 (t, 1H), 7.16 (dd, 1H), 5.72 (q, 2H), 5.38 (t, 1H), 4.76-4.84 (m, 1H), 4.06 (t, 1H), 3.93 (dq, 2H), 3.78 (dd, 1H), 3.68 (ddd, 1H), 3.55 (dt, 1H), 3.55 (dt, 2H), 3.14-3.19 (m, 4H), 3.10 (dt, 1H), 2.57 (tt, 1H), 2.34-2.47 (m, 2H), 2.17-2.22 (m, 2H), 1.69-1.86 (m, 4H). MS-APCI (m/z+): 529 (M+H).

Step 4: Preparation of (R)-tetrahydro-pyran-4-carboxylic acid (acetyl-{3-[4-(1,1-dioxo-hexahydro-1$\lambda^6$-thiopyran-4-yl)-3-fluoro-phenyl]-2-oxo-oxazolidin-5-ylmethyl}-carbamoyloxy)-methyl ester (91)

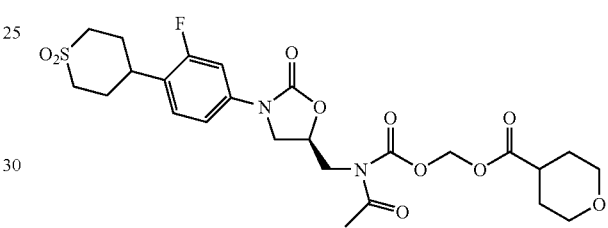

Following General Procedure D with (S)-tetrahydro-pyran-4-carboxylic acid 3-[4-(1,1-dioxo-hexahydro-1$\lambda^6$-thiopyran-4-yl)-3-fluoro-phenyl]-2-oxo-oxazolidin-5-ylmethylcarbamoyloxymethyl ester (81) (627.2 mg, 1.19 mmol) in dichloromethane (12 mL), the titled product is afforded in 90% yield (610.7 mg, 1.07 mmol). $^1$H NMR (400 MHz, CDCl$_3$): δ 7.48 (dd, 1H), 7.24 (t, 1H), 7.14 (dd, 1H), 5.89 (s, 2H), 4.78-4.86 (m, 1H), 4.18 (dd, 1H), 4.08 (t, 1H), 4.04 (dd, 1H), 3.92-4.00 (m, 2H), 3.68 (dd, 1H), 3.43 (t, 2H), 3.13-3.20 (m, 4H), 3.10 (dt, 1H), 2.69 (tt, 1H), 2.57 (s, 3H), 2.35-2.46 (m, 2H), 2.17-2.24 (m, 2H), 1.51-1.84 (m, 4H). MS-APCI (m/z+): 529 (M+H).

General Procedure 2

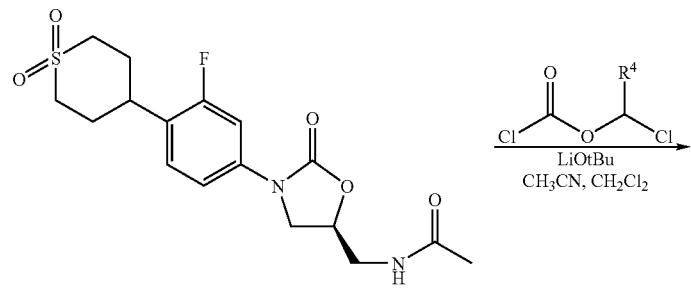

-continued

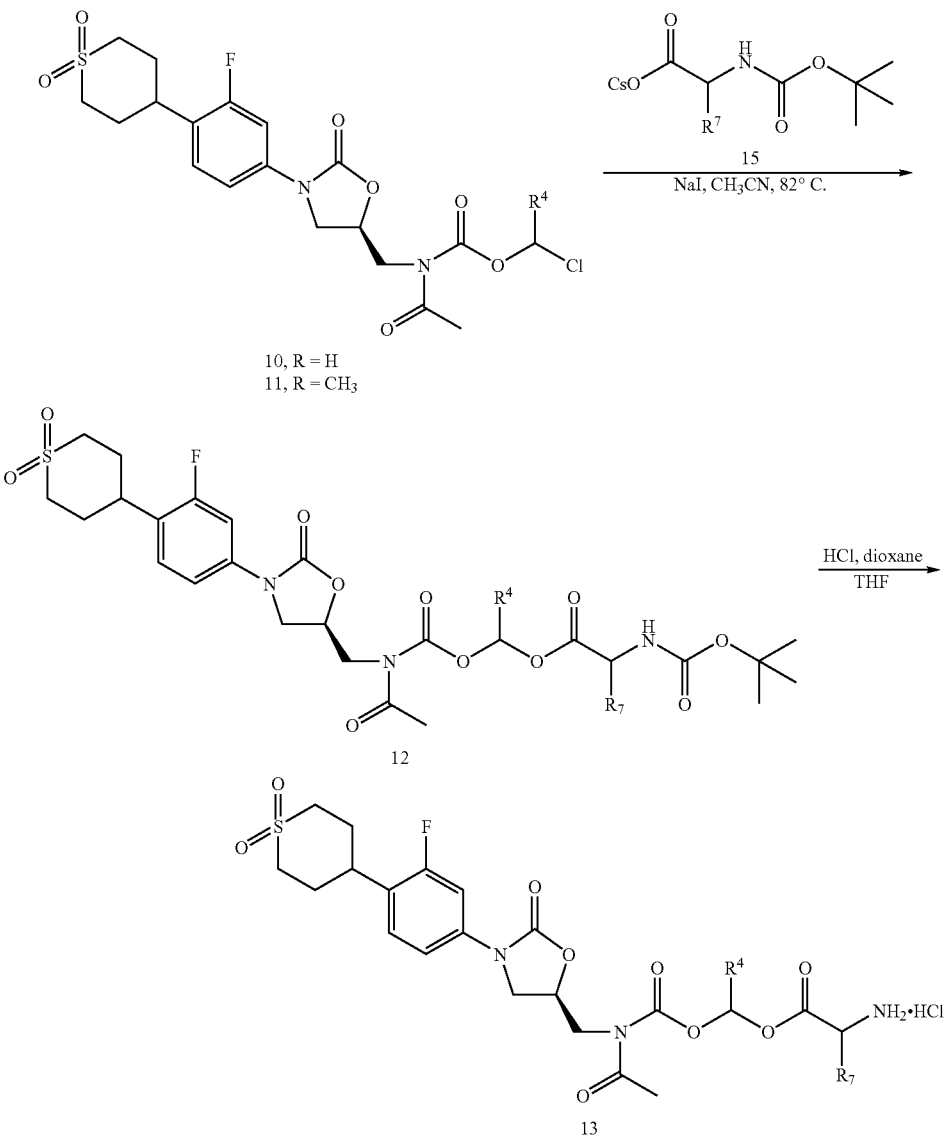

Preparation of (R)-acetyl-{3-[4-(1,1-dioxo-hexahydro-1λ⁶-thiopyran-4-yl)-3-fluoro-phenyl]-2-oxo-oxazolidin-5-ylmethyl}-carbamic acid chloromethyl ester (10)

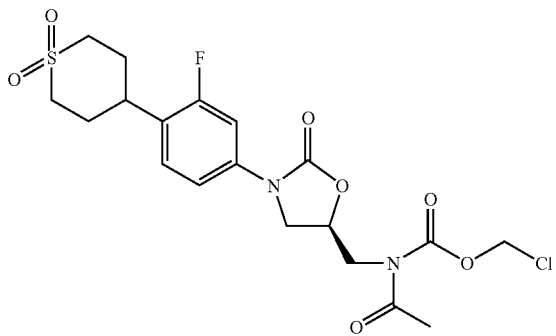

(S)-N-{3-[4-(1,1-Dioxo-hexahydro-1$\lambda^6$-thiopyran-4-yl)-3-fluoro-phenyl]-2-oxo-oxazolidin-5-ylmethyl}-acetamide (1) (2.0 g, 5.2 mmol) in 13 mL of $CH_2Cl_2$ and 13 mL of $CH_3CN$ is cooled to 0° C. Lithium t-butoxide (1.0 M in hexanes, 5.7 mL, 5.7 mmol) is added and the mixture is stirred at 0° C. for 25 min and then at RT for 10 min. The mixture is re-cooled to 0° C. and chloromethyl chloroformate (0.6 mL, 6.2 mmol) is added dropwise. The mixture is stirred for 10 min at 0° C. and then allowed to stir at RT overnight. The solution is diluted with $CH_2Cl_2$ and water and the layers are separated. The organic layer is washed with water, brine, dried over $Na_2SO_4$, and conc in vacuo. Purification by silica gel chromatography afforded the title compound in 74% yield (1.8 g). $^1$H NMR (400 MHz, $CDCl_3$): δ 7.47 (dd, 1H), 7.22 (t, 1H), 7.13 (dd, 1H), 5.91 (d, 1H), 5.76 (d, 1H), 4.82 (m, 1H), 4.16 (m, 1H), 4.07 (m, 2H), 3.69 (dd, 1H), 3.10 (m, 5H), 2.58 (s, 3H), 2.38 (m, 2H), 2.17 (m, 2H). MS-APCI (m/z+): 341, 385, 477.

Preparation of (R)-acetyl-{3-[4-(1,1-dioxo-hexahydro-1λ⁶-thiopyran-4-yl]-3-fluoro-phenyl]-2-oxo-oxazolidin-5(R)-ylmethyl}-carbamic acid 1(R,S)-chloro-ethyl ester (11)

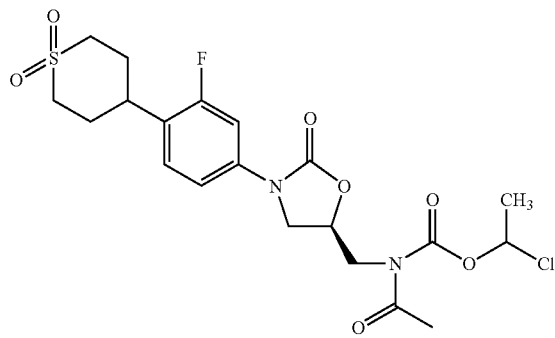

(S)-N-{3-[4-(1,1-Dioxo-hexahydro-1λ⁶-thiopyran-4-yl)-3-fluoro-phenyl]-2-oxo-oxazolidin-5-ylmethyl}-acetamide (1) (0.4 g, 1.0 mmol) in 2.5 mL of $CH_2Cl_2$ and 2.5 mL of $CH_3CN$ is cooled to 0° C. Lithium t-butoxide (1.0 M in hexanes, 1.1 mL, 1.1 mmol) is added and the mixture is stirred at 0° C. for 15 min and then at RT for 10 min. The mixture is re-cooled to 0° C. and 1-chloroethyl chloroformate (0.13 mL, 1.2 mmol) is added dropwise. The mixture is stirred for 10 min at 0° C. and then allowed to stir at RT overnight. The solution is diluted with $CH_2Cl_2$ and water and the layers are separated. The organic layer is washed with water, brine, dried over $Na_2SO_4$, and conc in vacuo. Purification by silica gel chromatography afforded the title compound in 64% yield (0.31 g) as a mixture of two diastereomers in a 1:1 ratio. ¹H NMR (400 MHz, $CDCl_3$): δ 7.46 (m, 1H), 7.22 (m, 1H), 7.13 (m, 1H), 6.57 (m, 1H), 4.82 (m, 1H), 4.22-4.02 (m, 3H), 3.73 (m, 0.5H), 3.68 (dd, 0.5H), 3.10 (m, 5H), 2.58 (s, 1.5H), 2.56 (s, 1.5H), 2.38 (m, 2H), 2.17 (m, 2H), 1.87 (app t, 3H). MS-APCI (m/z+): 341, 385, 491.

General Procedure E: Formation of Cesium Salts of N-BOC-Amino Acids (15)

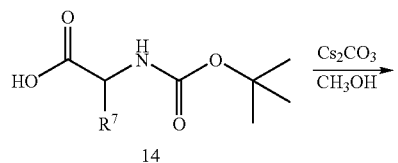

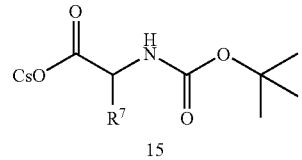

The procedure of Hegedus, L. S., *J. Org. Chem.* 1992, 57, 5453-5462 is used: The appropriate N-BOC-amino acid (14) (5.7 mmol) is dissolved in 24 mL of methanol and 2.4 mL of water. A 20% (w/w) aq solution of $Cs_2CO_3$ is added dropwise until the solution is titrated to pH 7 (as measured by pH paper). The solution is conc in vacuo and then re-evaporated twice from toluene. The resultant cesium salt is dried under full vacuum at 40° C. overnight and is used without further purification.

General Procedure F: Formation of N-BOC-Amino Acid Prodrugs (12)

(R)-Acetyl-{3-[4-(1,1-dioxo-hexahydro-1λ⁶-thiopyran-4-yl)-3-fluoro-phenyl]-2-oxo-oxazolidin-5-ylmethyl}-carbamic acid chloromethyl ester (10) (1 eq), the cesium salt of the appropriate N-BOC-amino acid (15) (1.55 eq), sodium iodide (1 eq), and acetonitrile are heated to reflux (82° C.) overnight. The mixture is then cooled to RT, filtered, and rinsed with $CH_2Cl_2$. The filtrate is diluted with $CH_2Cl_2$ and water and the layers are separated. The organic layer is washed with water, 10% $Na_2S_2O_3$, water, brine, dried over $Na_2SO_4$ and conc in vacuo. Purification is accomplished by silica gel chromatography.

General Procedure G: Formation of Amino Acid Prodrugs as HCl salt (13)

The appropriate N-BOC-amino acid prodrug (12) (1 eq), anisole and THF are cooled to 0° C. Hydrogen chloride (4 M in dioxane, 30 eq) is added dropwise. The mixture is then allowed to warm up to RT overnight. Ether is added dropwise to the mixture while stirring, resulting in the formation of a solid. The solid is collected via filtration, rinsed with ether, and dried under vacuum.

Example 13

Preparation of (R)-tert-butoxycarbonylamino-acetic acid (acetyl-{3-[4-(1,1-dioxo-hexahydro-1λ⁶-thiopyran-4-yl)-3-fluoro-phenyl]-2-oxo-oxazolidin-5-ylmethyl}-carbamoyloxy)-methyl ester (12a)

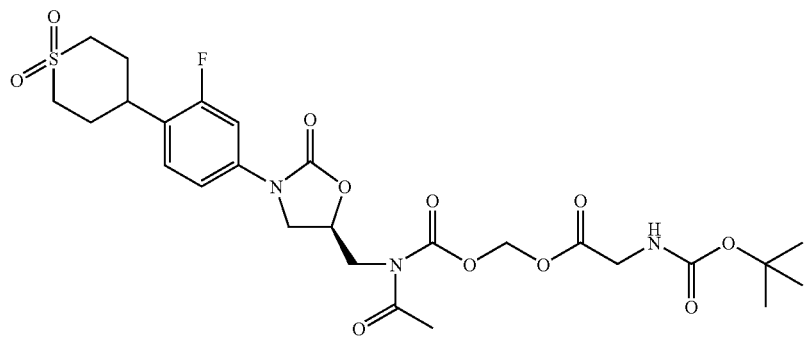

Following general procedure F, (R)-acetyl-{3-[4-(1,1-di-oxo-hexahydro-1λ⁶-thiopyran-4-yl)-3-fluoro-phenyl]-2-oxo-oxazolidin-5-ylmethyl}-carbamic acid chloromethyl ester (10) (0.4 g, 0.84 mmol), the cesium salt of N-BOC-glycine (15a) (0.4 g, 1.3 mmol), sodium iodide (0.13 g, 0.84 mmol), and 24 mL of acetonitrile gave the title compound in 74% yield (0.38 g). MS-APCI (m/z+): 516, 616.

Example 14

Preparation of 2(S)-tert-butoxycarbonylamino-propionic acid (acetyl-{3-[4-(1,1-dioxo-hexahydro-1λ⁶-thiopyran-4-yl)-3-fluoro-phenyl]-2-oxo-oxazolidin-5(R)-ylmethyl}-carbamoyloxy)-methyl ester (12b)

Example 15

Preparation of 2(S)-tert-butoxycarbonylamino-3-methyl-butyric acid (acetyl-{3-[4-(1,1-dioxo-hexahydro-1λ⁶-thiopyran-4-yl)-3-fluoro-phenyl]-2-oxo-oxazolidin-5(R)-ylmethyl}-carbamoyloxy)-methyl ester (12c)

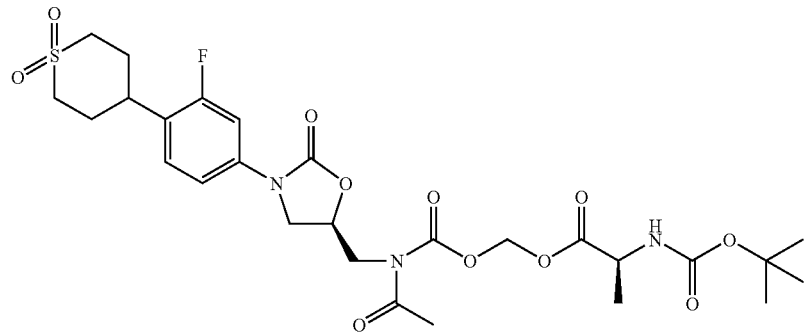

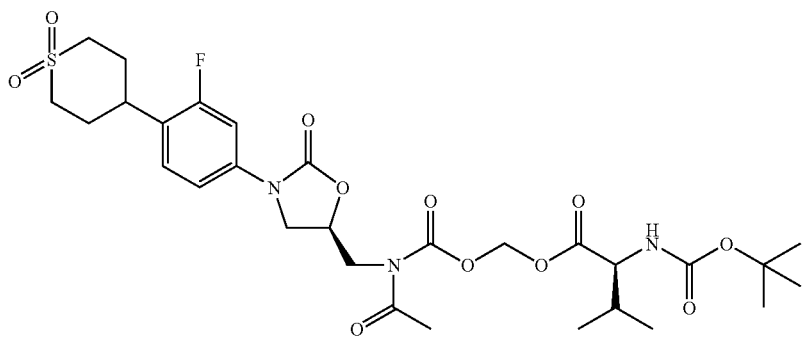

Following general procedure F, (R)-acetyl-{3-[4-(1,1-di-oxo-hexahydro-1λ⁶-thiopyran-4-yl)-3-fluoro-phenyl]-2-oxo-oxazolidin-5-ylmethyl}-carbamic acid chloromethyl ester (10) (0.92 g, 1.9 mmol), the cesium salt of N-BOC-L-alanine (15b) (0.96 g, 3.0 mmol), sodium iodide (0.29, 1.9 mmol), and 50 mL of acetonitrile gave the title compound in 85% yield (1.03 g). ¹H NMR (400 MHz, CDCl₃): δ7.46 (d, 1H), 7.21 (m, 1H), 7.13 (d, 1H), 5.89 (app s, 2H), 5.07 (br d, 1H), 4.81 (m, 1H), 4.31 (m, 1H), 4.17 (dd, 1H), 4.07 (app t, 1H), 4.02 (dd, 1H), 3.67 (dd, 1H), 3.14 (m, 4H), 3.09 (m, 1H), 2.55 (s, 3H), 2.38 (m, 2H), 2.17 (m, 2H), 1.39 (s, 12H). MS-APCI (m/z+): 530.

Following general procedure F, (R)-acetyl-{3-[4-(1,1-di-oxo-hexahydro-1λ⁶-thiopyran-4-yl)-3-fluoro-phenyl]-2-oxo-oxazolidin-5-ylmethyl}-carbamic acid chloromethyl ester (10) (0.41 g, 0.85 mmol), the cesium salt of N-BOC-L-valine (15c) (0.46 g, 1.3 mmol), sodium iodide (0.13 g, 0.85 mmol), and 24 mL of acetonitrile gave the title compound in 88% yield (0.49 g). ¹H NMR (400 MHz, CDCl₃): δ7.45 (dd, 1H), 7.20 (t, 1H), 7.13 (dd, 1H), 5.88 (ABq, 2H), 5.01 (br d, 1H), 4.79 (m, 1H), 4.17 (m, 2H), 4.06 (t, 1H), 3.99 (dd, 1H), 3.67 (dd, 1H), 3.11 (m, 5H), 2.53 (s,3H), 2.36 (m, 2H), 2.12 (m, 3H), 1.38 (s, 9H), 0.95 (d, 3H), 0.87 (d, 3H). MS-APCI (m/z+): 341, 385, 558, 658.

Example 16

Preparation of 2(R)-tert-butoxycarbonylamino-3-methyl-butyric acid (acetyl-{3-[4-(1,1-dioxo-hexahydro-1λ⁶-thiopyran-4-yl)-3-fluoro-phenyl]-2-oxo-oxazolidin-5(R)-ylmethyl}-carbamoyloxy)-methyl ester (12d)

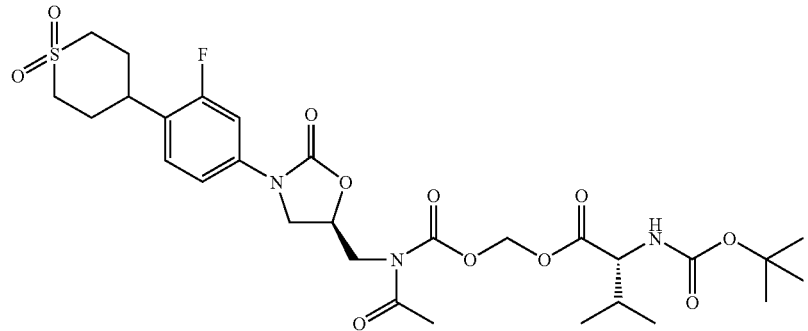

Following general procedure F, (R)-acetyl-{3-[4-(1,1-dioxo-hexahydro-1λ⁶-thiopyran-4-yl)-3-fluoro-phenyl]-2-oxo-oxazolidin-5-ylmethyl}-carbamic acid chloromethyl ester (10) (0.9 g, 1.89 mmol), the cesium salt of N-BOC-D-valine (15d) (1.02 g, 2.93 mmol), sodium iodide (0.28, 1.89 mmol), and 50 mL of acetonitrile gave the title compound in 81% yield (1.00 g). $^1$H NMR (400 MHz, CDCl$_3$): δ7.48 (dd, 1H), 7.21 (t, 1H), 7.13 (dd, 1H), 5.89 (ABq, 2H), 5.05 (br d, 1H), 4.81 (m, 1H), 4.19 (m, 2H), 4.07 (t, 1H), 4.00 (dd, 1H), 3.67 (dd, 1H), 3.14 (m, 4H), 3.09 (tt, 1H), 2.55 (s, 3H), 2.39 (m, 2H), 2.17 (m, 3H), 1.40 (s, 9H), 0.96 (d, 3H), 0.88 (d, 3H). MS-APCI (m/z+): 558, 602, 658.

Following general procedure F, (R)-acetyl-{3-[4-(1,1-dioxo-hexahydro-1λ⁶-thiopyran-4-yl)-3-fluoro-phenyl]-2-oxo-oxazolidin-5-ylmethyl}-carbamic acid chloromethyl ester (10) (0.4 g, 0.84 mmol), the cesium salt of N-BOC-L-leucine (15e) (0.47 g, 1.3 mmol), sodium iodide (0.13 g, 0.84 mmol), and 24 mL of acetonitrile gave the title compound in 79% yield (0.45 g). $^1$H NMR (400 MHz, CDCl$_3$): δ7.44 (dd, 1H), 7.18 (t, 1H), 7.12 (dd, 1H), 5.86 (ABq, 2H), 5.01 (br d, 1H), 4.78 (m, 1H), 4.24 (m, 1H), 4.15 (dd, 1H), 4.06 (t, 1H), 3.98 (dd, 1H), 3.66 (dd, 1H), 3.17-3.03 (m, 5H), 2.51 (s, 3H), 2.34 (m, 2H), 2.14 (m, 2H), 1.66 (m, 1H), 1.53 (m, 2H), 1.36 (s, 9H), 0.89 (d, 6H). MS-APCI (m/z+): 341, 385, 572, 672.

Example 17

Preparation of 2(S)-tert-butoxycarbonylamino-4-methyl-pentanoic acid (acetyl-{3-[4-(1,1-dioxo-hexahydro-1λ⁶-thiopyran-4-yl)-3-fluoro-phenyl]-2-oxo-oxazolidin-5(R)-ylmethyl}-carbamoyloxy)-methyl ester (12e)

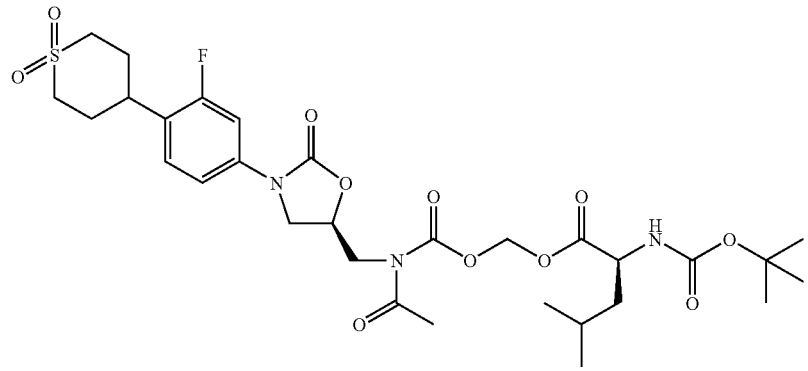

Example 18

Preparation of 2(S)-tert-butoxycarbonylamino-3(S)-methyl-pentanoic acid (acetyl-{3-[4-(1,1-dioxo-hexahydro-1λ⁶-thiopyran-4-yl)-3-fluoro-phenyl]-2-oxo-oxazolidin-5(R)-ylmethyl}-carbamoyloxy)-methyl ester (12f)

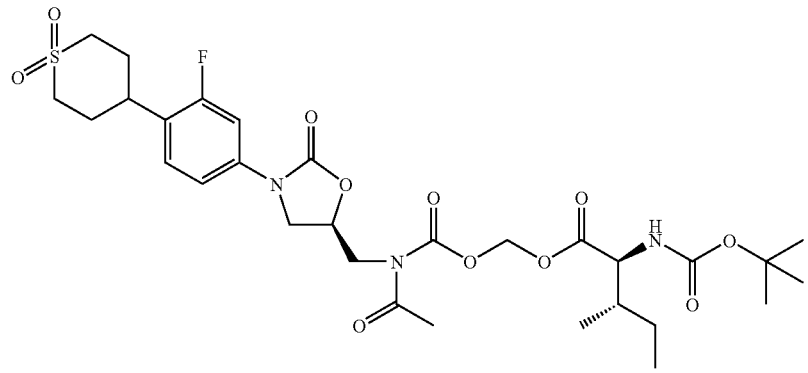

Following general procedure F, (R)-acetyl-{3-[4-(1,1-dioxo-hexahydro-1λ⁶-thiopyran-4-yl)-3-fluoro-phenyl]-2-oxo-oxazolidin-5-ylmethyl}-carbamic acid chloromethyl ester (10) (0.92 g, 1.9 mmol), the cesium salt of N-BOC-L-isoleucine (15f) (1.09 g, 3.0 mmol), sodium iodide (0.29, 1.9 mmol), and 50 mL of acetonitrile gave the title compound in 71% yield (0.93 g). $^1$H NMR (400 MHz, CDCl$_3$): δ7.46 (dd, 1H), 7.21 (t, 1H), 7.14 (dd, 1H), 5.89 (ABq, 2H), 5.00 (br d, 1H), 4.80 (m, 1H), 4.24 (dd, 1H), 4.17 (dd, 1H), 4.07 (app t, 1H), 4.00 (dd, 1H), 3.67 (dd, 1H), 3.13 (m, 4H), 3.09 (tt, 1H), 2.54 (s, 3H), 2.38 (m, 2H), 2.17 (m, 2H), 1.86 (m, 1H), 1.39 (s, 9H), 1.39 (m, 1H), 1.16 (m, 1H), 0.92 (d, 3H), 0.88 (t, 3H). MS-APCI (m/z+): 341, 385, 572.

Following general procedure F, (R)-acetyl-{3-[4-(1,1-dioxo-hexahydro-1λ⁶-thiopyran-4-yl)-3-fluoro-phenyl]-2-oxo-oxazolidin-5-ylmethyl}-carbamic acid chloromethyl ester (10) (0.75 g, 1.6 mmol), the cesium salt of N-BOC-L-phenylalanine (15 g) (0.96 g, 2.4 mmol), sodium iodide (0.23, 1.6 mmol), and 40 mL of acetonitrile gave the title compound in 76% yield (0.84 g). $^1$H NMR (400 MHz, CDCl$_3$): δ 7.46 (dd, 1H), 7.23 (m, 4H), 7.13 (m, 3H), 5.87 (ABq, 2H), 5.02 (br d, 1H), 4.79 (m, 1H), 4.56 (m, 1H), 4.14 (dd, 1H), 4.02 (m, 2H), 3.66 (dd, 1H), 3.17-3.00 m, 7H), 2.54 (s, 3H), 2.38 (m, 2H), 2.17 (m, 2H), 1.36 (s, 9H). MS-APCI (m/z+): 341, 385, 606.

Example 19

Preparation of 2(S)-tert-butoxycarbonylamino-3-phenyl-propionic acid (acetyl-{3-[4-(1,1-dioxo-hexahydro-1λ⁶-thiopyran-4-yl)-3-fluoro-phenyl]-2-oxo-oxazolidin-5(R)-ylmethyl}-carbamoyloxy)-methyl ester (12 g)

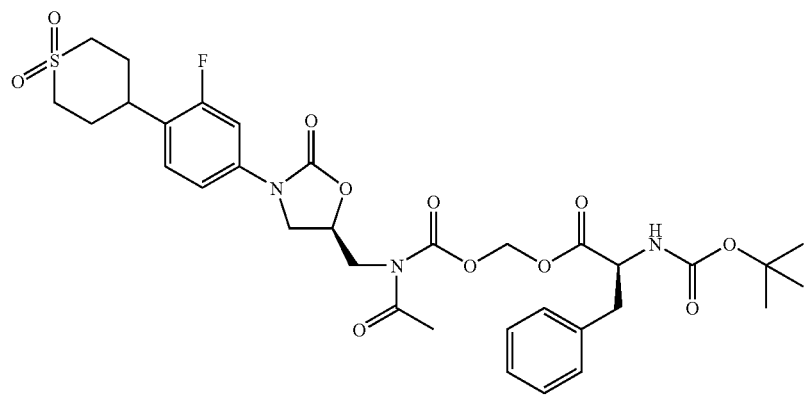

Example 20

Preparation of pyrrolidine-1,2-dicarboxylic acid 2(S)-[(acetyl-{3-[4-(1,1-dioxo-hexahydro-1λ⁶-thiopyran-4-yl)-3-fluoro-phenyl]-2-oxo-oxazolidin-5(R)-ylmethyl}-carbamoyloxy)-methyl] ester 1-tert-butyl ester (12 h)

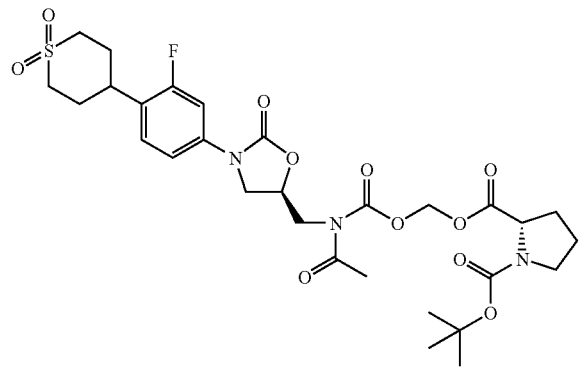

Following general procedure F, (R)-acetyl-{3-[4-(1,1-dioxo-hexahydro-1λ⁶-thiopyran-4-yl)-3-fluoro-phenyl]-2-oxo-oxazolidin-5-ylmethyl}-carbamic acid chloromethyl ester (10) (0.41 g, 0.85 mmol), the cesium salt of N-BOC-L-proline (15 h) (0.46 g, 1.3 mmol), sodium iodide (0.13 g, 0.85 mmol), and 24 mL of acetonitrile gave the title compound in 87% yield (0.48 g). $^1$H NMR (400 MHz, CDCl$_3$): δ7.46 (dd, 1H), 7.20 (t, 1H), 7.15 (dd, 1H), 5.88 (s, 2H), 4.83 (m, 1H), 4.30-4.14 (m, 2H), 4.11-3.97 (m, 2H), 3.68 (m, 1H), 3.45 (m, 2H), 3.10 (m, 5H), 2.54 (s, 3H), 2.39 (m, 2H), 2.17 (m, 2H), 1.93 (m, 4H), 1.38 (s, 9H). MS-APCI (m/z+): 556.

Example 21

Preparation of (R)-(2-tert-butoxycarbonylamino-acetylamino)-acetic acid (acetyl-{3-[4-(1,1-dioxo-hexahydro-1λ⁶-thiopyran-4-yl)-3-fluoro-phenyl]-2-oxo-oxazolidin-5-ylmethyl}-carbamoyloxy)-methyl ester (12i).

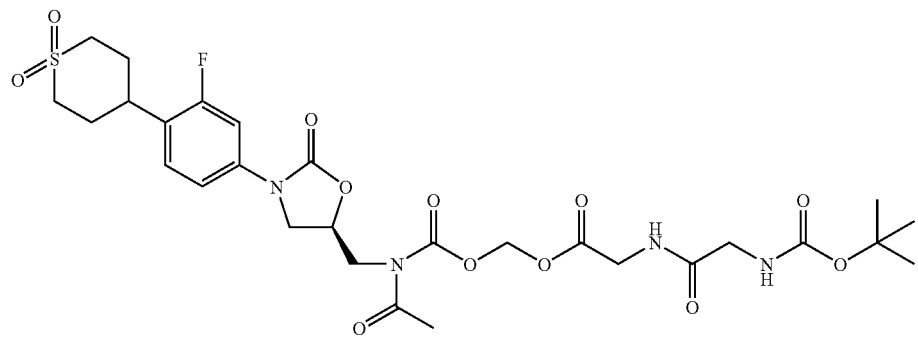

Following general procedure F, (R)-acetyl-{3-[4-(1,1-dioxo-hexahydro-1λ⁶-thiopyran-4-yl)-3-fluoro-phenyl]-2-oxo-oxazolidin-5-ylmethyl}-carbamic acid chloromethyl ester (10) (0.89 g, 1.87 mmol), the cesium salt of N-BOC-glycyl-glycine (15i) (1.06 g, 2.90 mmol), sodium iodide (0.28 g, 1.87 mmol), and 45 mL of acetonitrile gave the title compound in 82% yield (1.03 g). $^1$H NMR (400 MHz, CDCl$_3$): δ 7.41 (dd, 1H), 7.24 (m, 1H), 7.12 (dd, 1H), 7.00 (br s, 1H), 5.93 (d, 1H), 5.84 (d, 1H), 5.15 (br s, 1H), 4.81 (m, 1H), 4.28 (dd, 1H), 4.11 (m, 4H), 3.84 (app d, 2H), 3.65 (dd, 1H), 3.11 (m, 5H), 2.57 (s, 3H), 2.38 (m, 2H), 2.18 (m, 2H), 1.41 (s, 9H). MS-APCI (m/z+): 341, 385, 573.

Example 22

Preparation of (R)-amino-acetic acid (acetyl-{3-[4-(1,1-dioxo-hexahydro-1λ⁶-thiopyran-4-yl)-3-fluoro-phenyl]-2-oxo-oxazolidin-5-ylmethyl}-carbamoyloxy)-methyl ester hydrochloride (13a)

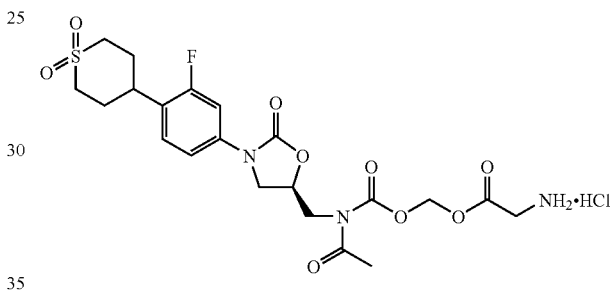

Following General procedure G, except that the entire reaction is performed at RT. (R)-Tert-butoxycarbonylamino-acetic acid (acetyl-{3-[4-(1,1-dioxo-hexahydro-1λ⁶-thiopyran-4-yl)-3-fluoro-phenyl]-2-oxo-oxazolidin-5-ylmethyl}-carbamoyloxy)-methyl ester (12a) (0.24 g, 0.39 mmol), anisole (0.5 mL), THF (7.3 mL), and 4 M HCl in dioxane (3 mL) gave the title compound in 72% yield (0.16 g). $^1$H NMR (400 MHz, DMSO): δ 8.39 (br d, 3H), 7.47 (dd, 1H), 7.39 (t, 1H), 7.28 (dd, 1H), 5.93 (m, 2H), 4.80 (m, 1H), 4.14 (m, 2H), 3.92 (m, 3H), 3.82 (m, 1H), 3.37 (m, 2H), 3.20 (m, 1H), 3.10 (m, 2H), 2.47 (s, 3H), 2.16 (m, 2H), 2.04 (m, 2H). MS-APCI (m/z+): 516, 616.

Example 23

Preparation of 2(S)-amino-propionic acid (acetyl-{3-[4-(1,1-dioxo-hexahydro-1λ⁶-thiopyran-4-yl)-3-fluoro-phenyl]-2-oxo-oxazolidin-5(R)-ylmethyl}-carbamoyloxy)-methyl ester hydrochloride (13b)

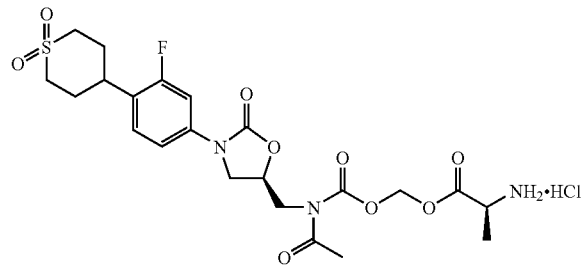

To a mixture of the 2(S)-tert-butoxycarbonylamino-propionic acid (acetyl-{3-[4-(1,1-dioxo-hexahydro-1λ⁶-thiopyran-4-yl)-3-fluoro-phenyl]-2-oxo-oxazolidin-5(R)-ylmethyl}-carbamoyloxy)-methyl ester (12b) (0.98 g, 1.56 mmol), anisole (1 mL) and THF (30 mL), is added hydrogen chloride (4 M in dioxane, 11 mL, 46.8 mmol) in a dropwise manner. The mixture is stirred at RT overnight. Under reduced pressure, the mixture is concentrated to one-half of its original volume. Ether is then added dropwise to the mixture while stirring, resulting in the formation of a solid. The solid is collected via filtration, rinsed with ether and ethyl acetate, and dried under vacuum to give the title compound in 38% yield (0.34 g). $^1$H NMR (400 MHz, CD$_3$OD): δ 7.51 (dd, 1H), 7.37 (t, 1H), 7.26 (dd, 1H), 6.02 (ABq, 2H), 4.87 (m, 1H), 4.29 (app q, 1H), 4.19 (m, 2H), 4.10 (dd, 1H), 3.83 (dd, 1H), 3.37 (m, 2H), 3.23 (tt, 1H), 3.12 (m, 2H), 2.54 (s, 3H), 2.35 (m, 2H), 2.18 (m, 2H), 1.59 (d, 3H). MS-APCI (m/z+): 530.

Example 24

Preparation of 2(S)-tert-butoxycarbonylamino-3-methyl-butyric acid (acetyl-{3-[4-(1,1-dioxo-hexahydro-1λ⁶-thiopyran-4-yl)-3-fluoro-phenyl]-2-oxo-oxazolidin-5(R)-ylmethyl}-carbamoyloxy)-methyl ester hydrochloride (13c)

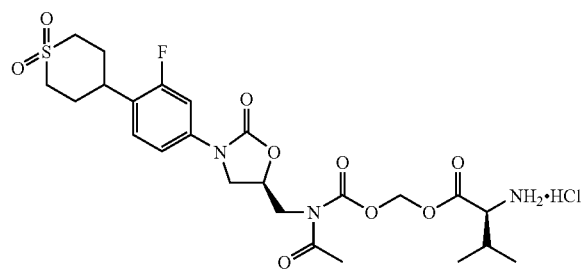

Following General procedure G, except that the entire reaction is performed at RT. 2(S)-tert-Butoxycarbonylamino-3-methyl-butyric acid (acetyl-{3-[4-(1,1-dioxo-hexahydro-1λ⁶-thiopyran-4-yl)-3-fluoro-phenyl]-2-oxo-oxazolidin-5(R)-ylmethyl}-carbamoyloxy)-methyl ester (12c) (0.40 g, 0.61 mmol), anisole (0.6 mL), THF (12 mL), and 4 M HCl in dioxane (4.6 mL) gave the title compound in 55% yield (0.20 g). $^1$H NMR (400 MHz, CD$_3$OD): δ 7.51 (dd, 1H), 7.37 (t, 1H), 7.26 (dd, 1H), 6.06 (d, 1H), 6.01 (d, 1H), 4.87 (m, 1H), 4.20 (m, 2H), 4.10 (m, 2H), 3.84 (dd, 1H), 3.37 (m, 2H), 3.24 (tt, 1H), 3.12 (m, 2H), 2.54 (s, 3H), 2.36 (m, 3H), 2.17 (m, 2H), 1.10 (d, 3H), 1.09 (d, 3H). MS-APCI (m/z+): 558.

Example 25

Preparation of 2(R)-amino-3-methyl-butyric acid (acetyl-{3-[4-(1,1-dioxo-hexahydro-1λ⁶-thiopyran-4-yl)-3-fluoro-phenyl]-2-oxo-oxazolidin-5(R)-ylmethyl}-carbamoyloxy)-methyl ester hydrochloride (13d)

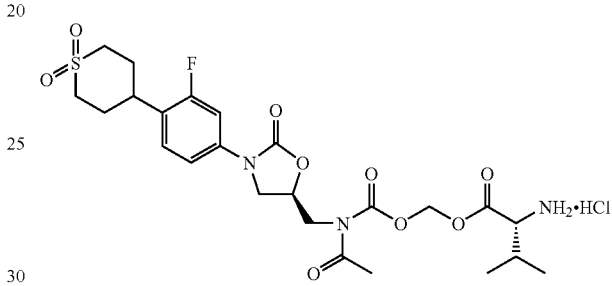

Following general procedure G, 2(R)-tert-Butoxycarbonylamino-3-methyl-butyric acid (acetyl-{3-[4-(1,1-dioxo-hexahydro-1λ⁶-thiopyran-4-yl)-3-fluoro-phenyl]-2-oxo-oxazolidin-5(R)-ylmethyl}-carbamoyloxy)-methyl ester (12d) (0.89 g, 1.35 mmol), anisole (0.12 mL), THF (25 mL), and 4 M HCl in dioxane (10 mL) gave the title compound in 51% yield (0.41 g). $^1$H NMR (400 MHz, DMSO): δ 8.52 (br s, 3H), 7.47 (dd, 1H), 7.39 (t, 1H), 7.28 (dd, 1H), 5.98 (d, 1H), 5.93 (d, 1H), 4.80 (m, 1H), 4.14 (m, 2H), 4.03 (d, 1H), 3.90 (dd, 1H), 3.82 (dd, 1H), 3.39 (m, 2H), 3.20 (tt, 1H), 3.10 (m, 2H), 2.47 (s, 3H), 2.17 (m, 3H), 2.04 (m, 2H), 0.98 (d, 3H), 0.96 (d, 3H), MS-APCI (m/z+): 558.

Example 26

Preparation of 2(S)-amino-4-methyl-pentanoic acid (acetyl-{3-[4-(1,1-dioxo-hexahydro-1λ⁶-thiopyran-4-yl)-3-fluoro-phenyl]-2-oxo-oxazolidin-5 (R)-ylmethyl}-carbamoyloxy)-methyl ester hydrochloride (13e)

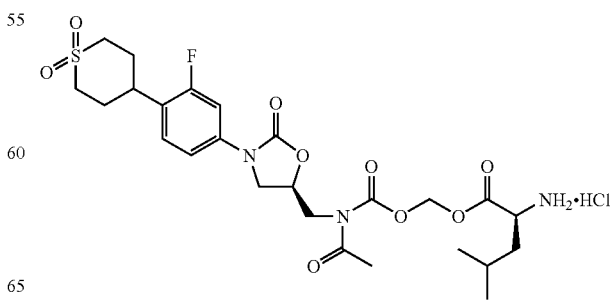

To a mixture of 2(S)-tert-Butoxycarbonylamino-4-methyl-pentanoic acid (acetyl-{3-[4-(1,1-dioxo-hexahydro-1λ⁶-thiopyran-4-yl)-3-fluoro-phenyl]-2-oxo-oxazolidin-5(R)-ylmethyl}-carbamoyloxy)-methyl ester (12e) (0.35 g, 0.52 mmol), anisole (0.5 mL) and THF (10 mL), is added hydrogen chloride (4 M in dioxane, 4 mL, 15.7 mmol) in a dropwise manner. The mixture is stirred at RT overnight. Ether is then added dropwise to the mixture while stirring. Under reduced pressure, the mixture is concentrated to one-third of its original volume. Ether is again added, resulting in the formation of a solid. The solid is collected via filtration, rinsed with ether and ethyl acetate, and dried under vacuum to give the title compound in 39% yield (0.12 g). ¹H NMR (400 MHz, CD₃OD): δ 7.52 (dd, 1H), 7.37 (t, 1H), 7.26 (dd, 1H), 6.02 (ABq, 2H), 4.88 (m, 1H), 4.20 (m, 3H), 4.10 (dd, 1H), 3.83 (m, 1H), 3.35 (m, 2H), 3.23 (tt, 1H), 3.12 (m, 2H), 2.54 (s, 3H), 2.35 (m, 2H), 2.17 (m, 2H), 1.85 (m, 2H), 1.72 (m, 1H), 1.02 (d, 3H), 1.01 (d, 3H). MS-APCI (m/z+): 341, 385, 572.

Example 27

Preparation of 2(S)-amino-3(S)-methyl-pentanoic acid (acetyl-{3-[4-(1,1-dioxo-hexahydro-1λ⁶-thiopyran-4-yl)-3-fluoro-phenyl]-2-oxo-oxazolidin-5(R)-ylmethyl}-carbamoyloxy)-methyl ester hydrochloride (13f)

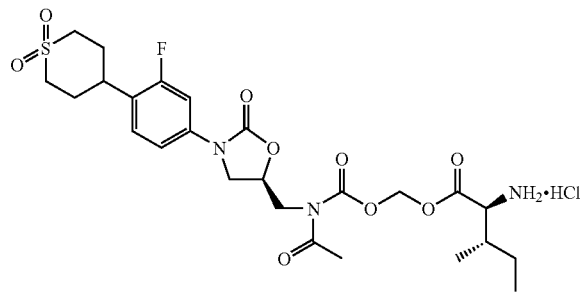

2(S)-tert-Butoxycarbonylamino-3(S)-methyl-pentanoic acid (acetyl-{3-[4-(1,1-dioxo-hexahydro-1λ⁶-thiopyran-4-yl)-3-fluoro-phenyl]-2-oxo-oxazolidin-5(R)-ylmethyl}-carbamoyloxy)-methyl ester (12f) (0.82 g, 1.23 mmol), anisole (0.2 mL) and THF (25 mL) are cooled to 0° C. Hydrogen chloride (4 M in dioxane, 9 mL, 36.8 mmol) is added in a dropwise manner. After complete addition, the ice-bath is removed and the mixture is stirred at RT overnight. Under reduced pressure, the mixture is concentrated to one-third of its original volume. Ether is then added dropwise to the mixture while stirring, resulting in the formation of a solid. The solid is collected via filtration, rinsed with ether, and dried under vacuum to give the title compound in 52% yield (0.39 g). ¹H NMR (400 MHz, CD₃OD): δ 7.51 (d, 1H), 7.36 (t, 1H), 7.26 (d, 1H), 6.05 (d, 1H), 6.00 (d, 1H), 4.87 (m, 1H), 4.20 (m, 3H), 4.09 (dd, 1H), 3.84 (dd, 1H), 3.37 (m, 2H), 3.23 (tt, 1H), 3.11 (m, 2H), 2.54 (s, 3H), 2.34 (m, 2H), 2.17 (m, 2H), 2.06 (m, 1H), 1.56 (m, 1H), 1.39 (m, 1H), 1.06 (d, 3H), 1.00 (t, 3H). MS-APCI (m/z+): 341, 385, 572.

Example 28

Preparation of 2(S)-amino-3-phenyl-propionic acid (acetyl-{3-[4-(1,1-dioxo-hexahydro-1λ⁶-thiopyran-4-yl)-3-fluoro-phenyl]-2-oxo-oxazolidin-5(R)-ylmethyl}-carbamoyloxy)-methyl ester hydrochloride (13g)

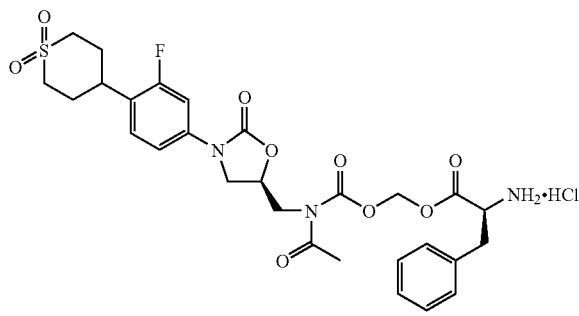

2(S)-tert-Butoxycarbonylamino-3-phenyl-propionic acid (acetyl-{3-[4-(1,1-dioxo-hexahydro-1λ⁶-thiopyran-4-yl)-3-fluoro-phenyl]-2-oxo-oxazolidin-5(R)-ylmethyl}-carbamoyloxy)-methyl ester (12 g) (0.78 g, 1.1 mmol), anisole (0.5 mL) and THF (20 mL) are cooled to 0° C. Hydrogen chloride (4 M in dioxane, 8 mL, 33.1 mmol) is added in a dropwise manner. After complete addition, the ice-bath is removed and the mixture is stirred at RT overnight. Under reduced pressure, the mixture is concentrated to one-half of its original volume. Ether is then added dropwise to the mixture while stirring, resulting in the formation of a solid. The solid is collected via filtration, rinsed with ether and ethyl acetate, and dried under vacuum to give the title compound in 63% yield (0.45 g). ¹H NMR (400 MHz, CD₃OD): δ 7.50 (dd, 1H), 7.39-7.24 (m, 7H), 6.02 (d, 1H), 5.97 (d, 1H), 4.86 (m, 1H), 4.50 (dd, 1H), 4.18 (m, 2H), 4.09 (dd, 1H), 3.83 (dd, 1H), 3.35 (m, 3H), 3.21 (m, 2H), 3.11 (m, 2H), 2.53 (s, 3H), 2.34 (m, 2H), 2.16 (m, 2H). MS-APCI (m/z+): 341, 385, 606.

Example 29

Preparation of pyrrolidine-2(S)-carboxylic acid (acetyl-{3-[4-(1,1-dioxo-hexahydro-1λ⁶-thiopyran-4-yl)-3-fluoro-phenyl]-2-oxo-oxazolidin-5(R)-ylmethyl}-carbamoyloxy)-methyl ester hydrochloride (13 h)

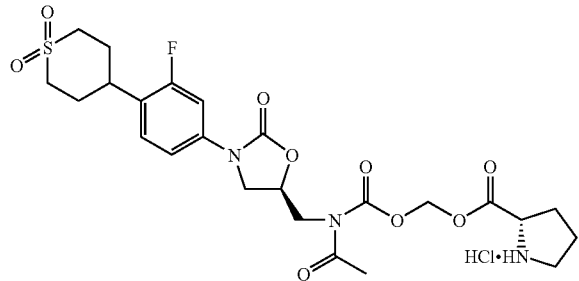

To a mixture of pyrrolidine-1,2-dicarboxylic acid 2(S)-[(acetyl-{3-[4-(1,1-dioxo-hexahydro-1λ⁶-thiopyran-4-yl)-3-fluoro-phenyl]-2-oxo-oxazolidin-5(R)-ylmethyl}-carbamoyloxy)-methyl] ester 1-tert-butyl ester (12 h) (0.43 g, 0.66 mmol), anisole (0.6 mL) and THF (14 mL), is added hydrogen chloride (4 M in dioxane, 5 mL, 19.9 mmol) in a dropwise manner. The mixture is stirred at RT overnight. Under reduced pressure, the mixture is concentrated to one-third of its original volume. Ether is added dropwise while stirring, resulting in the formation of a solid. The solid is collected via filtration, rinsed with ether and ethyl acetate, and dried under vacuum to give the title compound in 94% yield (0.37 g). MS-APCI (m/z+): 341, 385.

Example 30

Preparation of (R)-(2-amino-acetylamino)-acetic acid (acetyl-{3-[4-(1,1-dioxo-hexahydro-1λ$^6$-thiopyran-4-yl)-3-fluoro-phenyl]-2-oxo-oxazolidin-5-ylmethyl}-carbamoyloxy)-methyl ester hydrochloride (13i)

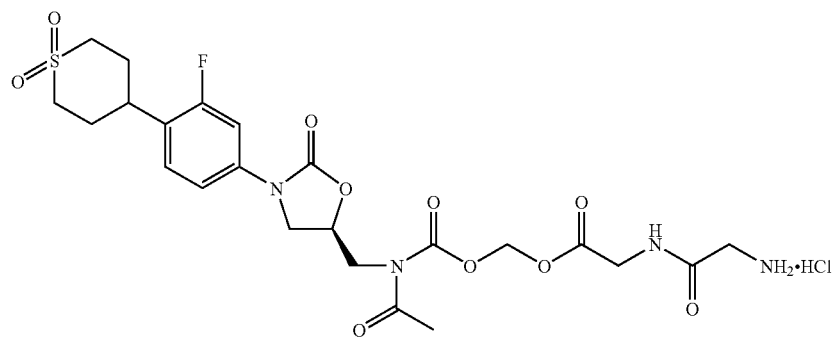

Following general procedure G, (R)-(2-tert-Butoxycarbonylamino-acetylamino)-acetic acid (acetyl-{3-[4-(1,1-dioxo-hexahydro-1λ$^6$-thiopyran-4-yl)-3-fluoro-phenyl]-2-oxo-oxazolidin-5-ylmethyl}-carbamoyloxy)-methyl ester (12i) (0.48 g, 0.71 mmol), anisole (0.1 mL), THF (14 mL), and 4 M HCl in dioxane (5 mL) gave the title compound in 66% yield (0.29 g). $^1$H NMR (400 MHz, CD$_3$OD): δ 7.51 (dd, 1H), 7.36 (t, 1H), 7.26 (dd, 1H), 5.95 (d, 1H), 5.91 (d, 1H), 4.87 (m, 1H), 4.20 (m, 4H), 4.05 (m, 1H), 3.82 (dd, 1H), 3.77 (m, 2H), 3.37 (m, 2H), 3.23 (tt, 1H), 3.12 (m, 2H), 2.53 (s, 3H), 2.35 (m, 2H), 2.18 (m, 2H). MS-APCI (m/z+): 341, 385, 573.

Example 31

Preparation of acetic acid 1-(acetyl-{3-[4-(1,1-dioxo-hexahydro-1λ$^6$-thiopyran-4-yl)-3-fluoro-phenyl]-2-oxo-oxazolidin-5(R)-ylmethyl}-carbamoyloxy)-ethyl ester (16)

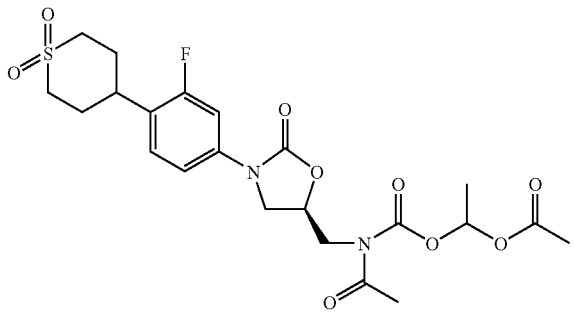

Acetyl-{3-[4-(1,1-dioxo-hexahydro-1λ$^6$-thiopyran-4-yl)-3-fluoro-phenyl]-2-oxo-oxazolidin 5(R)-ylmethyl}-carbamic acid 1(R,S)-chloro-ethyl ester (11) (0.49 g, 1 mmol), mercury(II) acetate (0.37 g, 1.175 mmol), and acetic acid (6.3 mL, 109 mmol) are stirred at RT overnight. Ether and water are added and the layers are separated. The organic layer is washed several times with water, brine, dried over Na$_2$SO$_4$ and conc in vacuo. After purification by silica gel chromatography, the product is re-dissolved in CH$_2$Cl$_2$ and washed with several portions of sat NaHCO$_3$, water, dried over Na$_2$SO$_4$ and conc in vacuo to give the title compound in 43% yield (0.51 g) as a mixture of two diastereomers in a 1:1 ratio. $^1$H NMR (400 MHz, CDCl$_3$): δ 7.46 (dt, 1H), 7.21 (m, 1H), 7.13 (m, 1H), 6.88 (q, 1H), 4.82 (m, 0.5H), 4.75 (m, 0.5H), 4.13 (m, 1H), 4.04 (m, 2H), 3.73 (dd, 0.5H), 3.67 (dd, 0.5H), 3.12 (m, 5H), 2.55 (s, 1.5H), 2.53 (s, 1.5H), 2.38 (m, 2H), 2.17 (m, 2H), 2.13 (s, 1.5H), 2.06 (s, 1.5H), 1.57 (d, 1.5H), 1.54 (d, 1.5H). MS-APCI (m/z+): 341, 385, 427, 515.

Example 32

Preparation of (R)-piperidine-1,4-dicarboxylic acid 4-[(acetyl-{3-[4-(1,1-dioxo-hexahydro-1λ⁶-thiopyran-4-yl)-3-fluoro-phenyl]-2-oxo-oxazolidin-5-ylmethyl}-carbamoyloxy)-methyl] ester 1-tert-butyl ester (17)

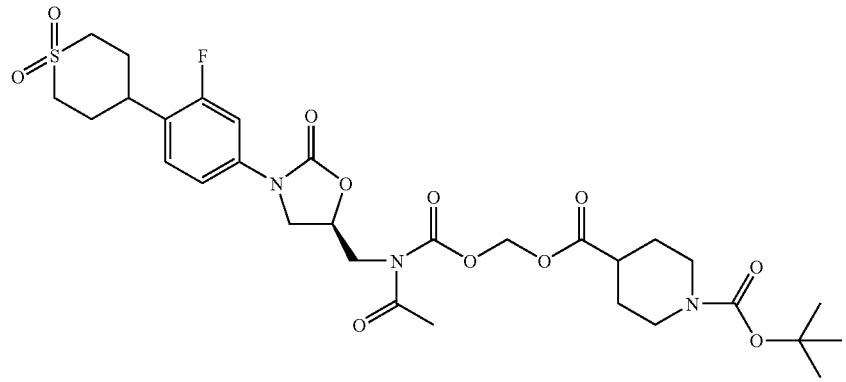

To (R)-acetyl-{3-[4-(1,1-dioxo-hexahydro-1λ⁶-thiopyran-4-yl)-3-fluoro-phenyl]-2-oxo-oxazolidin-5-ylmethyl}-carbamic acid chloromethyl ester (10) (751.8 mg, 1.58 mmol) and sodium iodide (236.0 mg, 1.58 mmol) in acetonitrile (30 mL), is added the cesium salt of N-BOC-isonipecotic acid (884.2 mg, 2.45 mmol). The mixture is heated to reflux overnight. After cooling to RT, the mixture is filtered and washed with dichloromethane. The filtrate is diluted with CH$_2$Cl$_2$ and water and the layers are separated. The aq layer is extracted with dichloromethane twice and the combined organic layers are washed with water, brine, dried over sodium sulfate and conc in vacuo. Purification by silica gel chromatography gave the title compound in 72% yield (757.3 mg, 1.13 mmol). $^1$H NMR (400 MHz, CDCl$_3$): δ 7.47 (dd, 1H), 7.24 (t, 1H), 7.14 (dd, 1H), 5.88 (s, 2H), 4.78-4.85 (m, 1H), 4.18 (dd, 1H), 4.08 (t, 2H), 4.03 (dd, 2H), 3.67 (dd, 1H), 3.13-3.20 (m, 4H), 3.10 (dt, 1H), 2.83 (t, 2H), 2.60 (tt, 1H), 2.59 (s, 3H), 2.35-2.46 (m, 2H), 2.17-2.23 (m, 2H), 1.90-1.96 (m, 2H), 1.57-1.686 (m, 2H) 1.45 (s, 9H). MS-APCI (m/z+): 570.

Example 33

Preparation of (R)-piperidine-4-carboxylic acid (acetyl-{3-[4-(1,1-dioxo-hexahydro-1λ⁶-thiopyran-4-yl)-3-fluoro-phenyl]-2-oxo-oxazolidin-5-ylmethyl}-carbamoyloxy)-methyl ester hydrochloride (18)

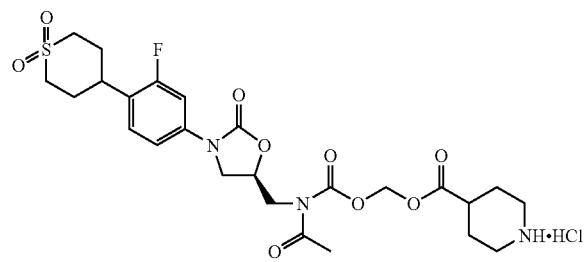

(R)-Piperidine-1,4-dicarboxylic acid 4-[(acetyl-{3-[4-(1,1-dioxo-hexahydro-1λ⁶-thiopyran-4-yl)-3-fluoro-phenyl]-2-oxo-oxazolidin-5-ylmethyl}-carbamoyloxy)-methyl] ester 1-tert-butyl ester (17) (588.5 mg, 0.88 mmol) and anisole (0.9 mL) are diluted with tetrahydrofuran (17 mL). Hydrochloric acid in dioxane (4 M, 6.6 mL) is added dropwise and the resultant mixture is stirred at RT overnight. Ether is added dropwise to the mixture while stirring, resulting in the formation of a solid. The solid is collected via filtration, rinsed with ether, and dried under vacuum to give the title compound in quantitative yield (530.8 mg, 0.88 mmol) $^1$H NMR (400 MHz, CD$_3$OD): δ 7.51 (dd, 1H), 7.36 (t, 1H), 7.26 (dd, 1H), 5.92 (s, 2H), 4.15-422 (m, 2H), 4.05 (dd, 1H), 3.81 (dd, 1H), 3.36-3.43 (m, 4H), 3.23 (tt, 1H), 3.05-3.14 (m, 5H), 2.90 (tt, 1H), 2.52 (s, 3H), 2.35 (q, 2H), 2.13-2.26 (m, 4H), 1.92-2.00 (m, 2H). MS-APCI (m/z+): 570.

Example 34

Preparation of 2(R)-phenyl-propionic acid (acetyl-{3-[4-(1,1-dioxo-hexahydro-1λ⁶-thiopyran-4-yl)-3-fluoro-phenyl]-2-oxo-oxazolidin-5(R)-ylmethyl}-carbamoyloxy)-methyl ester (19)

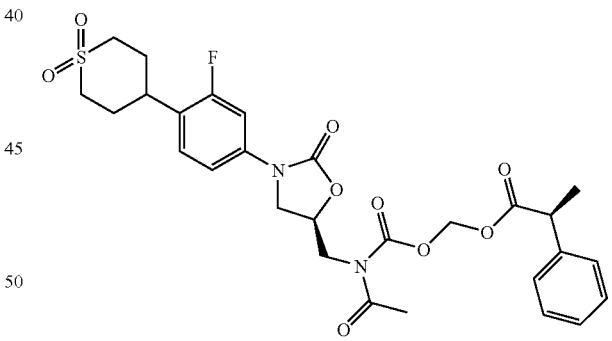

(R)-acetyl-{3-[4-(1,1-dioxo-hexahydro-1λ⁶-thiopyran-4-yl)-3-fluoro-phenyl]-2-oxo-oxazolidin-5-ylmethyl}-carbamic acid chloromethyl ester (10) (0.40 g, 0.84 mmol), cesium 2(R)-phenyl-propionate (0.37 g, 1.31 mmol) and sodium iodide (0.13 g, 0.86 mmol) in acetonitrile (25 mL) are heated to reflux overnight. After cooling to RT, water is added and the reaction mixture is extracted with EtOAc and then with dichloromethane. The organic phases are washed separately with brine and then the organic layers are combined, dried over MgSO$_4$, filtered, and conc in vacuo. The isolated residue is subjected to silica gel flash chromatography, eluting with MeOH/CH$_2$Cl$_2$ gradient (0-5% MeOH over 1 hour and 20 minutes) to afford the title compound. Isolated yield: 81%. $^1$H NMR (400 MHz, DMSO-d$_6$): δ 7.43-7.38 (m, 1H), 7.33 (t, 1H), 7.27-7.15 (m, 6H), 5.78-

5.72 (m, 2H), 4.63-4.57 (m, 1H), 4.04-3.95 (m, 2H), 3.84 (q, 1H), 3.76-3.69 (m, 2H), 3.36-3.26 (m, partially obscured by water, 2H), 3.17-3.12 (m, 1H), 3.07-3.04 (m, 2H), 2.31 (d, 3H), 2.11 (q, 2H), 2.01-1.97 (m, 2H), 1.35 (d, 3H); MS-APCI (m/z+): 341, 385, 517, 591.

Example 35

Preparation of 2(S)-phenyl-propionic acid (acetyl-{3-[4-(1,1-dioxo-hexahydro-1$\lambda^6$-thiopyran-4-yl)-3-fluoro-phenyl]-2-oxo-oxazolidin-5(R)-ylmethyl}-carbamoyloxy)-methyl ester (20)

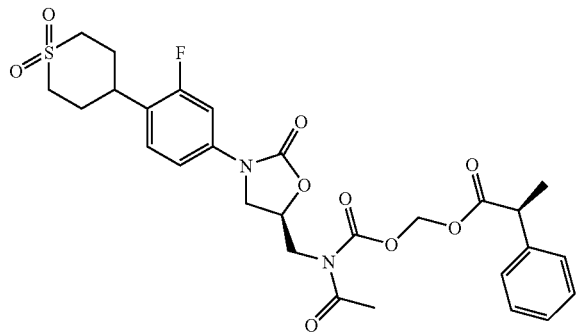

(R)-acetyl-{3-[4-(1,1-dioxo-hexahydro-1$\lambda^6$-thiopyran-4-yl)-3-fluoro-phenyl]-2-oxo-oxazolidin-5-ylmethyl}-carbamic acid chloromethyl ester (10) (0.40 g, 0.84 mmol), cesium 2(S)-phenyl-propionate (0.37 g, 1.31 mmol) and sodium iodide (0.13 g, 0.86 mmol) in acetonitrile (25 mL) are heated to reflux overnight. After cooling to RT, water is added and the reaction mixture is extracted with EtOAc and then with dichloromethane. The organic phases are washed separately with brine and then the organic layers are combined, dried over MgSO$_4$, filtered, and conc in vacuo. The isolated residue is subjected to silica gel flash chromatography, eluting with MeOH/CH$_2$Cl$_2$ gradient (0-5% MeOH over 1 hour and 20 minutes) to afford the title compound. Isolated yield: 75%. $^1$H NMR (400 MHz, DMSO-d$_6$): δ 7.43-7.39 (m, 1H), 7.33 (t, 1H), 7.27-7.15 (m, 6H), 5.78-5.72 (m, 2H), 4.63-4.57 (m, 1H0, 4.02-3.95 (m, 2H), 3.84 (q, 1H), 3.76-3.69 (m, 2H), 3.36-3.26 (m, partially obscured by water, 2H), 3.18-3.12 (m, 1H), 3.07-3.04 (m, 2H), 2.30 (d, 3H), 2.11 (q, 2H), 2.01-1.97 (m, 2H), 1.35 (d, 3H); MS-APCI (m/z+): 341, 385, 517, 591.

Example 36

Preparation of isonicotinic acid (acetyl-{3-[4-(1,1-dioxo-hexahydro-1$\lambda^6$-thiopyran-4-yl)-3-fluoro-phenyl]-2-oxo-oxazolidin-5(R)-ylmethyl}-carbamoyloxy)-methyl ester (21)

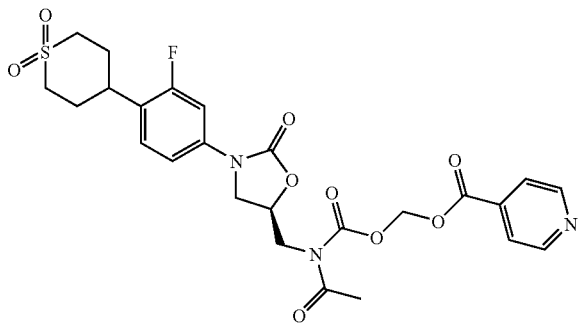

(R)-acetyl-{3-[4-(1,1-dioxo-hexahydro-1$\lambda^6$-thiopyran-4-yl)-3-fluoro-phenyl]-2-oxo-oxazolidin-5-ylmethyl}-carbamic acid chloromethyl ester (10) (0.40 g, 0.84 mmol), cesium isonicotinate (0.33 g, 1.301 mmol) and sodium iodide (0.13 g, 0.86 mmol) in acetonitrile (25 mL) are heated to reflux overnight. After cooling to RT, water is added and the reaction mixture is extracted with EtOAc and then with dichloromethane. The organic phases are washed separately with brine and then the organic layers are combined, dried over MgSO$_4$, filtered, and conc in vacuo. The isolated residue is subjected to silica gel flash chromatography, eluting with MeOH/CH$_2$Cl$_2$ gradient (0-5% MeOH over 1 hour and 20 minutes) to afford the title compound. Isolated yield: 80%. $^1$H NMR (400 MHz, DMSO-d$_6$): δ 8.78 (d, 2H), 7.82 (d, 2H), 7.36 (d, 1H), 7.30 (t, 1H), 7.18 (d, 1H), 6.02 (dd, 2H), 4.76-4.70 (m, 1H), 4.10-4.05 (m, 2H), 3.89-3.85 (m, 1H), 3.77-3.74 (m, 1H), 3.35-3.26 (m, partially obscured by water, 2H), 3.19-3.11 (m, 1H), 3.07-3.04 (m, 2H), 2.43 (d, partially obscured by DMSO, 3H), 2.11 (q, 2H), 2.01-1.97 (m, 2H); MS-APCI (m/z+): 341, 564.

Example 37

Preparation of propionic acid 1-(acetyl-{3-[4-(1,1-dioxo-hexahydro-1$\lambda^6$-thiopyran-4-yl)-3-fluoro-phenyl]-2-oxo-oxazolidin-5(R)-ylmethyl}-carbamoyloxy)-ethyl ester (22)

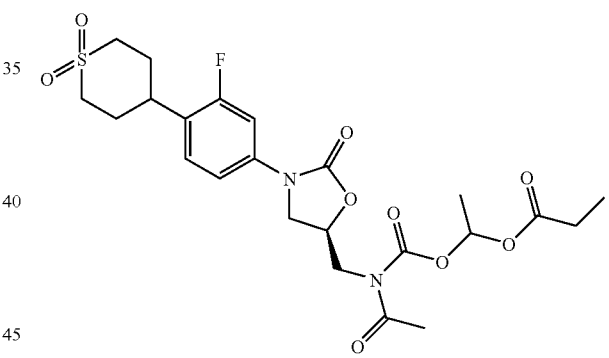

Acetyl-{3-[4-(1,1-dioxo-hexahydro-1$\lambda^6$-thiopyran-4-yl)-3-fluoro-phenyl]-2-oxo-oxazolidin-5(R)-ylmethyl}-carbamic acid 1-chloro-ethyl ester (11) (0.20 g, 0.41 mmol) and sodium iodide (0.061 g, 0.41 mmol) are placed in acetonitrile (25 mL) and stirred at RT overnight. Cesium propionate (0.17 g, 0.82 mmol) is then added and the reaction is heated at reflux overnight. After cooling to RT, water is added and the reaction mixture is extracted with EtOAc and then with dichloromethane. The organic phases are washed separately with brine and then the organic layers are combined, dried over MgSO$_4$, filtered, and conc in vacuo. The isolated residue is subjected to silica gel flash chromatography, eluting with MeOH/CH$_2$Cl$_2$ gradient (0-5% MeOH over 1 hour and 20 minutes) to afford the title compound. Isolated yield: 67%. $^1$H NMR (400 MHz, CDCl$_3$): δ 7.48-7.42 (m, 1H), 7.21-7.17 (m, 1H), 7.13-7.10 (m, 1H), 6.90-6.85 (m, 1H), 4.83-4.69 (m, 1H), 4.14-3.98 (m, 3H), 3.73-3.64 (m, 1H), 3.13-3.04 (m, 5H), 2.52 (d, 3H), 2.48-2.31 (m, 3H), 2.29-2.13 (m, 2H), 1.56-1.51 (m, 4H), 1.15-1.07 (m, 3H).

Example 38

Preparation of isonicotinic acid 1-(acetyl-{3-[4-(1,1-dioxo-hexahydro-1λ⁶-thiopyran-4-yl)-3-fluoro-phenyl]-2-oxo-oxazolidin-5(R)-ylmethyl}-carbamoyloxy)-ethyl ester (23)

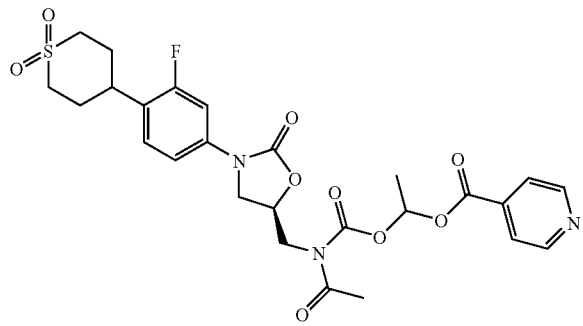

Acetyl-{3-[4-(1,1-dioxo-hexahydro-1λ⁶-thiopyran-4-yl)-3-fluoro-phenyl]-2-oxo-oxazolidin-5(R)-ylmethyl}-carbamic acid 1-chloro-ethyl ester (11) (0.40 g, 0.81 mmol) and cesium isonicotinate (0.42 g, 1.64 mmol) in acetonitrile (20 mL) are heated to reflux overnight. After cooling to RT, water is added and the reaction mixture is extracted with EtOAc and then with dichloromethane. The organic phases are washed separately with brine and then the organic layers are combined, dried over MgSO$_4$, filtered, and conc in vacuo. The isolated residue is subjected to silica gel flash chromatography, eluting with MeOH/CH$_2$Cl$_2$ gradient (0-5% MeOH over 1 hour and 20 minutes) to afford the title compound. Isolated yield: 83%. $^1$H NMR (400 MHz, DMSO-d$_6$): δ 8.78-8.74 (m, 2H), 7.85 (dd, 1H), 7.79 (dd, 1H), 7.40-7.35 (m, 1H), 7.31 (t, 1H), 7.21-7.17 (m, 1H), 7.01-6.94 (m, 1H), 4.79-4.72 (m, 1H), 4.12-4.00 (m, 2H), 3.91-3.84 (m, 1H), 3.78-3.73 (m, 1H), 3.36-3.26 (m, partially obscured by water, 2H), 3.17-3.11 (m, 1H), 3.07-3.03 (m, 2H), 2.40 (d, 3H), 2.15-2.04 (m, 2H), 2.00-1.97 (m, 2H) 1.59 (dd, 3H).

Example 39

Preparation of 2(S)-tert-butoxycarbonylamino-3(S)-methyl-pentanoic acid 1-(acetyl-{3-[4-(1,1-dioxo-hexahydro-1λ⁶-thiopyran-4-yl)-3-fluoro-phenyl]-2-oxo-oxazolidin-5(R)-ylmethyl}-carbamoyloxy)-ethyl ester (12j)

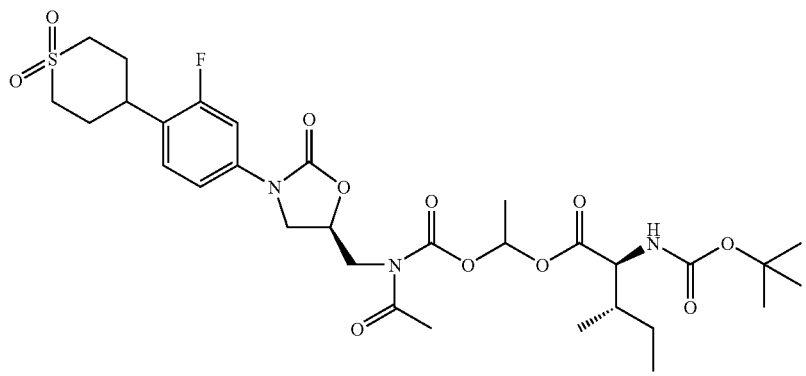

Acetyl-{3-[4-(1,1-dioxo-hexahydro-1λ⁶-thiopyran-4-yl)-3-fluoro-phenyl]-2-oxo-oxazolidin-5(R)-ylmethyl}-carbamic acid 1-chloro-ethyl ester (11) (1.00 g, 2.04 mmol), the cesium salt of N-BOC-L-isoleucine (15f) (1.48 g, 4.07 mmol), sodium iodide (0.31 g, 2.07 mmol) and acetonitrile (50 mL) are heated to reflux overnight. After cooling to RT, water is added and the reaction mixture is extracted with EtOAc and then with dichloromethane. The organic phases are washed separately with brine and then the organic layers are combined, dried over MgSO$_4$, filtered, and conc in vacuo. The isolated residue is subjected to silica gel flash chromatography, eluting with MeOH/CH$_2$Cl$_2$ gradient (0-4% MeOH over 1 hour and 30 minutes) to afford the title compound. Isolated yield: 79%. $^1$H NMR (400 MHz, CDCl$_3$): δ 7.48-7.42 (m, 1H), 7.22-7.17 (m, 1H), 7.14-7.10 (m, 1H), 6.91-6.85 (m, 1H), 5.08 (d, 0.5H), 4.94 (d, 0.5H), 4.81-4.74 (m, 1H), 4.24-3.98 (m, 4H), 3.71-3.64 (m, 1H), 3.13-3.04 (m, 5H), 2.51 (d, 3H), 2.42-2.31 (m, 2H), 2.17-2.13 (m, 2H), 1.84-1.81 (br m, 1H), 1.57 (dd, 3H), 1.52 (s, 1H), 1.38 (d, 9H), 1.21-1.09 (m, 1H), 0.93-0.85 (m, 6H); MS-APCI (m/z+): 341, 385, 586, 686.

Example 40

Preparation of 2,2-dimethyl-propionic acid 1-(acetyl-{3-[4-(1,1-dioxo-hexahydro-1λ⁶-thiopyran-4-yl)-3-fluoro-phenyl]-2-oxo-oxazolidin-5(R)-ylmethyl}-carbamoyloxy)-ethyl ester (24)

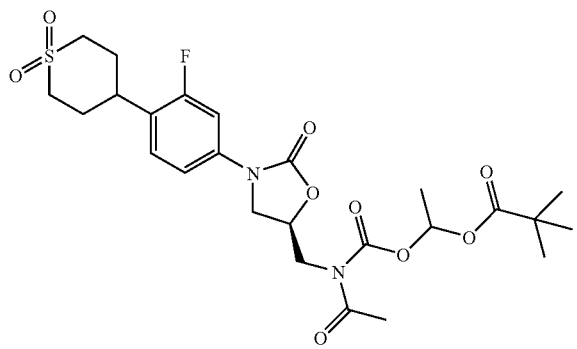

Acetyl-{3-[4-(1,1-dioxo-hexahydro-1λ⁶-thiopyran-4-yl)-3-fluoro-phenyl]-2-oxo-oxazolidin-5(R)-ylmethyl}-carbamic acid 1-chloro-ethyl ester (11) (0.40 g, 0.81 mmol), cesium 2,2-dimethyl-propionate (0.38 g, 1.63 mmol), sodium iodide (0.121 g, 0.81 mmol) and acetonitrile (25 mL) are heated to reflux overnight. After cooling to RT, water is added and the reaction mixture is extracted with EtOAc and then with dichloromethane. The organic phases are washed separately with brine and then the organic layers are combined, dried over MgSO$_4$, filtered, and conc in vacuo. The isolated residue is subjected to silica gel flash chromatography, eluting with MeOH/CH$_2$Cl$_2$ gradient (0-4% MeOH over 1 hour and 30 minutes) to afford the title compound. Isolated yield: 30%. $^1$H NMR (400 MHz, DMSO-d$_6$): δ 7.41-7.38 (m, 1H), 7.33 (t, 1H), 7.22 (dd, 1H), 6.71-6.65 (m, 1H), 4.77-4.68 (m, 1H), 4.12-3.94 (m, 2H), 3.88-3.74 (m, 2H), 3.36-3.28 (m, 2H), 3.18-3.12 (m, 1H), 3.07-3.03 (m, 2H), 2.37 (d, 3H), 2.15-2.06 (m, 2H), 2.00-1.97 (m, 2H) 1.44 (dd, 3H); 1.08 (d, 9H).

Example 41

Preparation of 2(S)-Amino-3(S)-methyl-pentanoic acid 1-(acetyl-{3-[4-(1,1-dioxo-hexahydro-1λ$^6$-thiopyran-4-yl)-3-fluoro-phenyl]-2-oxo-oxazolidin-5(R)-ylmethyl}-carbamoyloxy)-ethyl ester hydrochloride (13j)

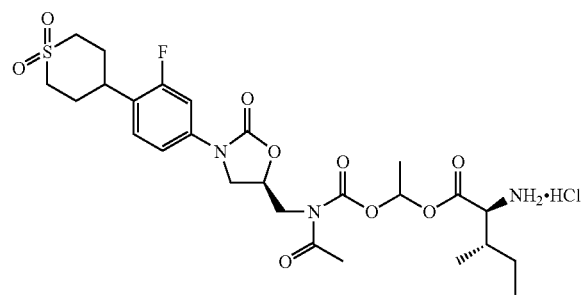

2(S)-tert-butoxycarbonylamino-3(S)-methyl-pentanoic acid 1-(acetyl-{3-[4-(1,1-dioxo-hexahydro-1λ$^6$-thiopyran-4-yl)-3-fluoro-phenyl]-2-oxo-oxazolidin-5(R)-ylmethyl}-carbamoyloxy)-ethyl ester (12j) (1.00 g, 1.46 mmol), anisole (0.24 g, 2.188 mmol) and THF (30 mL) are cooled in an ice bath. Hydrochloric acid (4 N in dioxane, 10.94 mL) is added dropwise. The solution is stirred in an ice bath for 30 min and then at RT for 4 h. The reaction mixture is re-cooled to 0° C. and ethyl ether is added. The resulting solids are collected by filtration and washed with a cold ethyl ether/ethyl acetate mixture to afford the title compound. Isolated yield: 64%. $^1$H NMR (400 MHz, DMSO-d$_6$): δ 8.46 (br s, 3H), 7.43-7.39 (m, 1H), 7.36 (t, 1H), 7.22 (d, 1H), 6.85-6.79 (m, 1H), 4.77-4.71 (m, 1H), 4.13-4.00 (m, 2H), 3.96 (dd, 1H),3.88-3.84 (m, 1H), 3.80-3.74 (m, 1H), 3.51-3.28 (m, partially obscured by water, 2H), 3.18-3.12 (m, 1H), 3.04 (d, 2H), 2.40 (d, 3H), 2.08 (q, 2H), 1.97-1.93 (m, 2H), 1.90-1.84 (br m, 1H), 1.50 (dd, 3H), 1.44-1.36 (m, 1H), 1.26-1.14 (m, 1H), 0.88 (dd, 3H), 0.84-0.79 (m, 3H).

Example 42

Preparation of Cyclopentanecarboxylic acid 1-(acetyl-{3-[4-(1,1-dioxo-hexahydro-1λ$^6$-thiopyran-4-yl)-3-fluoro-phenyl]-2-oxo-oxazolidin-5(R)-ylmethyl}-carbamoyloxy)-ethyl ester (25)

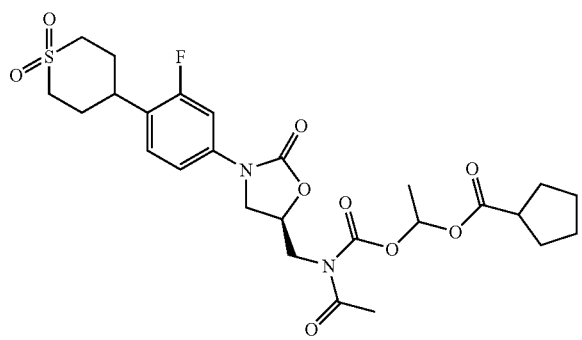

Acetyl-{3-[4-(1,1-dioxo-hexahydro-1λ$^6$-thiopyran-4-yl)-3-fluoro-phenyl]-2-oxo-oxazolidin-5(R)-ylmethyl}-carbamic acid 1-chloro-ethyl ester (11) (0.20 g, 0.41 mmol), cesium cyclopentanecarboxylate (0.20 g, 0.81 mmol) and sodium iodide (0.061 g, 0.41 mmol) in acetonitrile (15 mL) were heated to reflux overnight. Upon cooling to RT, water was added and the reaction mixture was extracted with ethyl acetate and then with dichloromethane. The organic phases were washed with brine, combined, dried over magnesium sulfate, filtered, and conc in vacuo. The isolated residue was subjected to silica gel flash chromatography, eluting with MeOH/CH$_2$Cl$_2$ gradient (0-4% MeOH over 1 hour and 20 minutes) to afford the title compound. Isolated yield: 63%. $^1$H NMR (400 MHz, DMSO-d$_6$): δ 7.39 (dd, 1H), 7.35-7.31 (m, 1H), 7.24-7.20 (m, 1H), 6.73-6.69 (m, 1H), 4.74-4.70 (m, 1H), 4.12-3.93 (m, 2H), 3.88-3.73 (m, 2H), 3.39-3.28 (m, 2H), 3.26 (s, 3H), 3.18-3.11 (m, 1H), 3.06-3.03 (m, 2H), 2.76-2.68 (m, 1H), 2.37 (d, 3H), 2.15-2.06 (m, 2H), 2.00-1.97-(m, 2H), 1.80-1.70 (m, 2H), 1.68-1.56 (m, 2H), 1.54-1.43 (m+dd, 4H).

We claim:
1. A compound of formula I

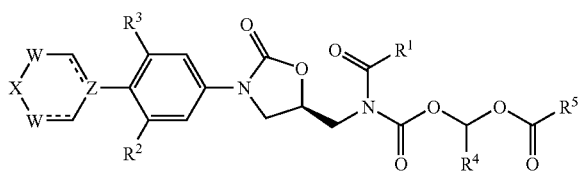

or a pharmaceutically acceptable salt thereof wherein:
X is —SO—, —SO$_2$—, or —SONR$^6$—;
Z is —C—, —CH—, or —N—;
each " . . . " is independently absent, or a bond;
each W is independently —CHR$^6$—, —CHR$^6$CH$_2$—, or absent;
R$^1$ is
  (a) —NH$_2$,
  (b) —NHC$_{1-4}$alkyl,
  (c) —C$_{1-6}$alkyl, optionally substituted with 1-3 halo, (d) —C$_{2-6}$alkenyl,
(e) —(CH$_2$)$_n$C(=O)C$_{1-4}$alkyl,
(f) —OC$_{1-4}$alkyl,
(g) —SC$_{1-4}$alkyl, or
(h) —(CH$_2$)$_n$C$_{3-7}$cycloalkyl;
R$^2$ and R$^3$ are independently —H, or —F;
R$^4$ is —H, —C$_{1-4}$alkyl, or —CO$_2$R$^6$;
R$^5$ is
(a) —C$_{1-10}$alkyl,
(b) —C$_{3-7}$cycloalkyl,
(c) -aryl,
(d) -het,
(e) —OC$_{1-10}$alkyl,
(f) —O—C$_{3-7}$cycloalkyl,
(g) —O-aryl,
(h) —O-het,
(i) —C(R$^6$)(R$^7$)NH$_2$,
(j) —C(R$^6$)(R$^7$)NHCO$_2$C$_{1-4}$alkyl,
(k) —C(R$^6$)(R$^7$)NHCOC(R$^6$)(R$^7$)NH$_2$, or
(l) —C(R$^6$)(R$^7$)NHCOC(R$^6$)(R$^7$)NHCO$_2$C$_{1-4}$alkyl;
each R$^6$ is independently —H, or —C$_{1-4}$alkyl;
each R$^7$ is independently —H, —C$_{1-4}$alkyl wherein —C$_{1-4}$ alkyl is optionally substituted with OR$^6$, SR$^6{}_3$, CO$_2$R$^6$, CONH$_2$, NH$_2$, NHC(=NH)NH$_2$, phenyl, het, or R$^6$ and R$^7$ taken together form het;
aryl is phenyl, biphenyl, or naphthyl;
het is an aromatic ring, or a saturated or unsaturated ring that is not aromatic, of 3 to 10 carbon atoms and 1 to 4 heteroatoms selected from the group consisting of O, NQ, and S within the ring, wherein Q is absent, H, C$_{1-4}$ alkyl or —CO$_2$C$_{1-4}$alkyl;
at each occurrence, C$_{1-10}$alkyl is optionally substituted with 1-3 halo, OH, CN, NO$_2$, OC$_{1-4}$ alkyl, NR$^6$R$^6$, C(=O)C$_{1-4}$alkyl, OC(=O)C$_{1-4}$alkyl, C(=O)OC$_{1-4}$ alkyl, phenyl or S(O)$_n$C$_{1-4}$alkyl;
at each occurrence, C$_{3-7}$cycloalkyl is optionally substituted with 1-3 halo, OH, CN, NO$_2$, C$_{1-4}$ alkyl, OC$_{1-4}$ alkyl, NR$^6$R$^6$, C(=O)C$_{1-4}$alkyl, OC(=O)C$_{1-4}$alkyl, C(=O)OC$_{1-4}$alkyl, or S(O)$_n$C$_{1-4}$alkyl;
at each occurrence, aryl is optionally substituted with 1-3 halo, OH, CN, NO$_2$, C$_{1-4}$alkyl, OC$_{1-4}$ alkyl, NR$^6$R$^6$, C(=O)C$_{1-4}$alkyl, OC(=O)C$_{1-4}$alkyl, C(=O)OC$_{1-4}$ alkyl, or S(O)$_n$C$_{1-4}$alkyl;
at each occurrence het is optionally substituted with 1-3 halo, OH, CN, NO$_2$, C$_{1-4}$alkyl, OC$_{1-4}$ alkyl, NR$^6$R$^6$, C(=O)C$_{1-4}$alkyl, OC(=O)C$_{1-4}$alkyl, C(=O)OC$_{1-4}$ alkyl, S(O)$_n$C$_{1-4}$alkyl, or oxo;
and each n is independently 0-4.

2. A compound of claim 1 wherein each W is independently —CH$_2$—.
3. A compound of claim 1 wherein X is —SO$_2$—.
4. A compound of claim 1 wherein Z is —CH—.
5. A compound of claim 1 wherein Z is —N—.
6. A compound of claim 1 wherein R$^2$ is H and R$^3$ is F.
7. A compound of claim 1 wherein R$^1$ is C$_{1-4}$alkyl, optionally substituted with one, two, or three halo.
8. A compound of claim 1 wherein R$^1$ is —CH$_3$.
9. A compound of claim 1 wherein R$^1$ is —CH$_2$CH$_3$, —CHF$_2$, —CF$_3$, or —CHCl$_2$.
10. A compound of claim 1 wherein R$^4$ is —H, or —CH$_3$.
11. A compound of claim 1 wherein R$^5$ is —C$_{1-5}$alkyl, optonally substituted with phenyl.
12. A compound of claim 1 wherein R$^5$ is cyclopropane, cyclopentane, or cyclohexane.
13. A compound of claim 1 wherein R$^5$ is phenyl.
14. A compound of claim 1 wherein R$^5$ is an unsaturated het of 3 to 4 carbon atoms and 1 to 2 heteroatoms selected from the group consisting of O, NQ, and S within the ring, wherein Q is absent, H, C$_{1-4}$ alkyl or —CO$_2$C$_{1-4}$alkyl.
15. A compound of claim 14 wherein R$^5$ is tetrahydropyran, piperidine, or pyrrolidine.
16. A compound of claim 1 wherein R$^5$ is C(R$^6$)(R$^7$)NH$_2$ wherein R$^6$ is H or methyl; and R$^7$ is H, Me, Et, iso-propyl, sec-butyl, CH(Me)Et, benzyl, CH$_2$OH, CH$_2$COOH, CH$_2$CH$_2$COOH, CONH$_2$, or CH$_2$CONH$_2$.
17. A compound of claim 1 wherein R$^5$ is C(R$^6$)(R$^7$)NH$_2$ wherein R$^6$ is H; and R$^7$ is C$_{1-5}$alkyl optionally substituted with phenyl.
18. A compound of claim 1 wherein R$^5$ is C(R$^6$)(R$^7$)NH$_2$ wherein R$^6$ is H; and R$^7$ is C$_{1-4}$alkyl.
19. A compound of claim 1 wherein R$^5$ is C(R$_6$)(R$^7$)NHCOC(R$^6$)(R$^7$)NH$_2$ wherein R$^6$ is H or methyl; and R$^7$ is H, Me, Et, iso-propyl, sec-butyl, CH(Me)Et, benzyl, CH$_2$OH, CH$_2$COOH, CH$_2$CH$_2$COOH, CONH$_2$, or CH$_2$CONH$_2$.
20. A compound of claim 1 which is a compound of formula Ia

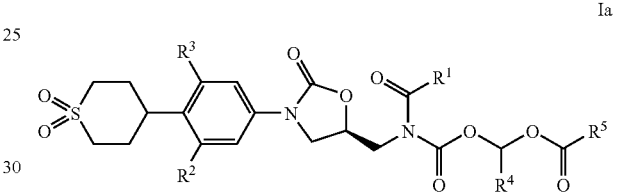

Ia or a pharmaceutically acceptable salt thereof wherein:
R$^1$ is —C$_{1-6}$alkyl, optionally substituted with 1-3 halo,
R$^2$ and R$^3$ are independently —H, or —F;
R$^4$ is —H, or —C$_{1-4}$alkyl;
R$^5$ is
(a) —C$_{1-10}$alkyl,
(b) —C$_{3-7}$cycloalkyl,
(c) -phenyl,
(d) -het,
(e) —C(R$^6$)(R$^7$)NH$_2$,
(f) —C(R$^6$)(R$^7$)NHCO$_2$C$_{1-4}$alkyl,
(g) —C(R$^6$)(R$^7$)NHCOC(R$^6$)(R$^7$)NH$_2$, or
(h) —C(R$^6$)(R$^7$)NHCOC(R$^6$)(R$^7$)NHCO$_2$C$_{1-4}$alkyl;
each R$^6$ is independently —H, or —C$_{1-4}$alkyl; and
each R$^7$ is independently —H, —C$_{1-4}$alkyl wherein —C$_{1-4}$ alkyl is optionally substituted with OR$^6$, SR$^6{}_3$, CO$_2$R$^6$, CONH$_2$, NH$_2$, NHC(=NH)NH$_2$, phenyl, het, or R$^6$ and R$^7$ taken together form het.

21. A compound of claim 1 which is a compound of formula Ib

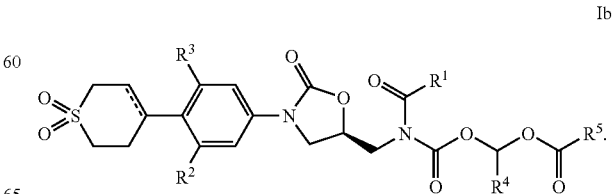

Ib

22. A compound of claim 1 which is a compound of formula Ic

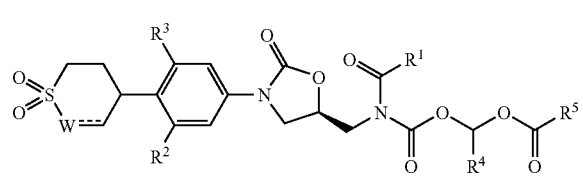

wherein W is —CH₂—, or —CH₂CH₂—.

23. A compound of claim 1 wherein pharmaceutically acceptable salt is hydrogen chloride.

24. A compound of claim 1 which is (1) ({[acetyl({(5R)-3-[4-(1,1-dioxidotetrahydro-2H-thiopyran4-yl)-3-fluorophenyl]-2-oxo-1,3oxazolidin-5-yl}-methyl)amino] carbonyl}oxy)methylacetate, (2) (R)-propionic acid (acetyl-{3-[4-(1,1-dioxo-hexahydro-1λ⁶-thiopyran-4-yl)-3-fluoro-phenyl]-2-oxo-oxazolidin-5-ylmethyl}-carbamoyloxy)-methyl ester, (3) (R)-isobutyric acid (acetyl-{3-[4-(1,1-dioxo-hexahydro-1λ⁶-thiopyran-4-yl)-3-fluoro-phenyl]-2-oxo-oxazolidin-5-ylmethyl}-carbamoyloxy)-methyl ester, (4) (R)-3-methyl-butyric acid (acetyl-{3-[4-(1,1-dioxo-hexahydro-1λ⁶-thiopyran-4-yl)-3-fluoro-phenyl]-2-oxo-oxazolidin-5-ylmethyl}-carbamoyloxy)-methyl ester, (5) (R)-butyric acid (acetyl-{3-[4-(1,1-dioxo-hexahydro-1λ⁶-thiopyran-4-yl)-3-fluoro-phenyl]-2-oxo-oxazolidin-5-ylmethyl}-carbamoyloxy)-methyl ester, (6) (R)-2.2-dimethy-propionic acid (acetyl-{3-[4-(1,1-dioxo-hexahydro-1λ⁶-thiopyran-4-yl)-3-fluoro-phenyl]-2-oxo-oxazolidin-5-ylmethyl}-carbamoyloxy)-methyl ester, (7) (R)-3.3-dimethy-butyric acid (acetyl-{3-[4-(1,1-dioxo-hexahydro-1λ⁶-thiopyran-4-yl)-3-fluoro-phenyl]-2-oxo-oxazolidin-5-ylmethyl}-carbamoyloxy)-methyl ester, (8) (R)-cyclopropanecarboxylic acid (acetyl-{3-[4-(1,1-dioxo-hexahydro-1λ⁶-thiopyran-4-yl)-3-fluoro-phenyl]-oxazolidin-5-ylmethyl}-carbamoyloxy)-methyl ester, (9) (R)-cyclopentanecarboxylic acid (acetyl-{3-[4-(1,1-dioxo-hexahydro-1λ⁶-thiopyran-4-yl)-3-fluoro-phenyl]-2-oxo-oxazolidin-5-ylmethyl}-carbamoyloxy)-methyl ester,

(10) (R)-cyclohexanecarboxylic acid (acetyl-{3-[4-(1,1-dioxo-hexahydro-1λ⁶-thiopyran-4-yl)-3-fluoro-phenyl]-2-oxo-oxazolidin-5-ylmethyl}-carbamoyloxy)-methyl ester,

(11) (R)-benzoic acid (acetyl-{3-[4-(1,1-dioxo-hexahydro-1λ⁶-thiopyran-4-yl)-3-fluoro-phenyl]-2-oxo-oxazolidin-5-ylmethyl}-carbamoyloxy)-methyl ester,

(12) (R)-tetrahydro-pyran-4-carboxylic acid (acetyl-{3-[4-(1,1-dioxo-hexahydro-1λ⁶-thiopyran-4-yl)-3-fluoro-phenyl]-2-oxo-oxazolidin-5-ylmethyl}-carbamoyloxy)-methyl ester,

(13) (R)-tert-butoxycarbonylamino-acetic acid (acetyl-{3-[4-(1,1-dioxo-hexahydro-1λ⁶-thiopyran-4-yl)-3-fluoro-phenyl]-2-oxo-oxazolidin-5-ylmethyl}-carbamoyloxy)-methyl ester,

(14) 2(S)-tert-butoxycarbonylamino-propionic acid (acetyl-{3-[4-(1,1-dioxo-hexahydro-1λ⁶-thiopyran-4-yl)-3-fluoro-phenyl]-2-oxo-oxazolidin-5(R)-ylmethyl}-carbamoyloxy)-methyl ester,

(15) 2(S)-tert-butoxycarbonylamino-3-methyl-butyric acid (acetyl-{3-[4-(1,1-dioxo-hexahydro-1λ⁶-thiopyran-4-yl)-3-fluoro-phenyl]-2-oxo-oxazolidin-5(R)-ylmethyl}-carbamoyloxy)-methyl ester,

(16) 2(R)-tert-butoxycarbonylamino-3-methyl-butyric acid (acetyl-{3-[4-(1,1-dioxo-hexahydro-1λ⁶-thiopyran-4-yl)-3-fluoro-phenyl]-2-oxo-oxazolidin-5(R)-ylmethyl}-carbamoyloxy)-methyl ester,

(17) 2(S)-tert-butoxycarbonylamino-4-methyl-pentanoic acid (acetyl-{3-[4-(1,1-dioxo-hexahydro-1λ⁶-thiopyran-4-yl)-3-fluoro-phenyl]-2-oxo-oxazolidin-5(R)-ylmethyl}-carbamoyloxy)-methyl ester,

(18) 2(S)-tert-butoxycarbonylamino-3(S)-methyl-pentanoic acid (acetyl-{3-[4-(1,1-dioxo-hexahydro-1λ⁶-thiopyran-4-yl)-3-fluoro-phenyl]-2-oxo-oxazolidin-5(R)-ylmethyl}-carbamoyloxy)-methyl ester,

(19) 2(S)-tert-butoxycarbonylamino-3-phenyl-propionic acid (acetyl-{3-[4-(1,1-dioxo-hexahydro-1λ⁶-thiopyran-4-yl)-3-fluoro-phenyl]-2-oxo-oxazolidin-5(R)-ylmethyl}-carbamoyloxy)-methyl ester,

(21) Pyrrolidine-1,2-dicarboxylic acid 2(S)-[(acetyl-{3-[4-(1,1-dioxo-hexahydro-1λ⁶-thiopyran-4-yl)-3-fluoro-phenyl]-2-oxo-oxazolidin-5(R)-ylmethyl}-carbamoyloxy)-methyl] ester 1-tert-butyl ester,

(21) (R)-(2-tert-butoxycarbonylamino-acetylamino)-acetic acid (acetyl-{3-[4-(1,1-dioxo-hexahydro-1λ⁶-thiopyran-4-yl)-3-fluoro-phenyl]-2-oxo-oxazolidin-5-ylmethyl}-carbamoyloxy)-methyl ester,

(22) (R)-amino-acetic acid (acetyl-{3-[4-(1,1-dioxo-hexahydro-1λ⁶-thiopyran-4-yl)-3-fluoro-phenyl]-2-oxo-oxazolidin-5-ylmethyl}-carbamoyloxy)-methyl ester hydrochloride,

(23) 2(S)-amino-propionic acid (acetyl-{3-[4-(1,1-dioxo-hexahydro-1λ⁶-thiopyran-4-yl)-3-fluoro-phenyl]-2-oxo-oxazolidin-5(R)-ylmethyl}-carbamoyloxy)-methyl ester hydrochloride,

(24) 2(S)-tert-butoxycarbonylamino-3-methyl-butyric acid (acetyl-{3-[4-(1,1-dioxo-hexahydro-1λ⁶-thiopyran-4-yl)-3-fluoro-phenyl]-2-oxo-oxazolidin-5(R)-ylmethyl}-carbamoyloxy)-methyl ester hydrochloride,

(25) 2(R)-amino-3-methyl-butyric acid (acetyl-{3-[4-(1,1-dioxo-hexahydro-1λ⁶-thiopyran-4-yl)-3-fluoro-phenyl]-2-oxo-oxazolidin-5(R)-ylmethyl}-carbamoyloxy)-methyl ester hydrochloride,

(26) 2(S)-amino-4-methyl-pentanoic acid (acetyl-{3-[4-(1,1-dioxo-hexahydro-1λ⁶-thiopyran-4-yl)-3-fluoro-phenyl]-2-oxo-oxazolidin-5(R)-ylmethyl}-carbamoyloxy)-methyl ester hydrochloride,

(27) 2(S)-amino-3(S)-methyl-pentanoic acid (acetyl-{3-[4-(1,1-dioxo-hexahydro-1λ⁶-thiopyran-4-yl)-3-fluoro-phenyl]-2-oxo-oxazolidin-5(R)-ylmethyl}-carbamoyloxy)-methyl ester hydrochloride,

(28) 2(S)-amino-3-phenyl-propionic acid (acetyl-{3-[4-(1,1-dioxo-hexahydro-1λ⁶-thiopypyran-4-yl)-3-fluoro-phenyl]-2-oxo-oxazolidin-5(R)-ylmethyl}-carbamoyloxy)-methyl ester hydrochloride,

(29) Pyrrolidine-2(S)-carboxylic acid (acetyl-{3-[4-(1,1-dioxo-hexahydro-1λ⁶-thiopyran-4-yl)-3-fluoro-phenyl]-2-oxo-oxazolidin-5(R)-ylmethyl}-carbamoyloxy)-methyl ester hydrochloride,

(30) (R)-(2-amino-acetylamino)-acetic acid (acetyl-{3-[4-(1,1-dioxo-hexahydro-1λ⁶-thiopyran-4-yl)-3-fluoro-phenyl]-2-oxo-oxazolidin-5-ylmethyl}-carbamoyloxy)-methyl ester hydrochloride,

(31) Acetic acid 1-(acetyl-{3-[4-(1,1-dioxo-hexahydro-1λ⁶-thiopyran-4-yl)-3-fluoro-phenyl]-2-oxo-oxazolidin-5(R)-ylmethyl}-carbamoyloxy)-ethyl ester,

(32) (R)-piperidine-1,4-dicarboxylic acid 4-[(acetyl-{3-[4-(1,1-dioxo-hexahydro-1λ⁶-thiopyran-4-yl)-3-fluoro-phenyl]-2-oxo-oxazolidin-5-ylmethyl}-carbamoyloxy)-methyl] ester 1-tert-butyl ester,

(33) (R)-piperidine-4-carboxylic acid (acetyl-{3-[4-(1,1-dioxo-hexahydro-1$\lambda^6$-thiopyran-4-yl)-3-fluoro-phenyl]-2-oxo-oxazolidin-5-ylmethyl}-carbamoyloxy)-methyl ester hydrochloride,

(34) 2(R)-phenyl-propionic acid (acetyl-{3-[4-(1,1-dioxo-hexahydro-1$\lambda^6$-thiopyran-4-yl)-3-fluoro-phenyl]-2-oxo-oxazolidin-5(R)-ylmethyl}-carbamoyloxy)-methyl ester,

(35) 2(S)-phenyl-propionic acid (acetyl-{3-[4-(1,1-dioxo-hexahydro-1$\lambda^6$-thiopyran-4-yl)-3-fluoro-phenyl]-2-oxo-oxazolidin-5(R)-ylmethyl}-carbamoyloxy)-methyl ester,

(36) Isonicotinic acid (acetyl-{3-[4-(1,1-dioxo-hexahydro-1$\lambda^6$-thiopyran-4-yl)-3-fluoro-phenyl]-2-oxo-oxazolidin-5(R)-ylmethyl}-carbamoyloxy)-methyl ester,

(37) Propionic acid 1-(acetyl-{3-[4-(1,1-dioxo-hexahydro-1$\lambda^6$-thiopyran-4-yl)-3-fluoro-phenyl]-2-oxo-oxazolidin-5(R)-ylmethyl}-carbamoyloxy)-ethyl ester,

(38) Isonicotinic acid 1-(acetyl-{3-[4-(1,1-dioxo-hexahydro-1$\lambda^6$-thiopyran-4-yl)-3-fluoro-phenyl]-2-oxo-oxazolidin-5(R)-ylmethyl}-carbamoyloxy)-ethyl ester,

(39) 2(S)-tert-butoxycarbonylamino-3(S)-methyl-pentanoic acid 1-(acetyl-{3-[4-(1,1-dioxo-hexahydro-1$\lambda^6$-thiopyran-4-yl)-3-fluoro-phenyl]-2-oxo-oxazolidin-5(R)-ylmethyl}-carbamoyloxy)-ethyl ester,

(40) 2,2-dimethyl-propionic acid 1-(acetyl-{3-[4-(1,1-dioxo-hexahydro-1$\lambda^6$-thiopyran-4-yl)-3-fluoro-phenyl]-2-oxo-oxazolidin-5(R)-ylmethyl}-carbamoyloxy)-ethyl ester,

(41) Preparation of 2(S)-Amino-3(S)-methyl-pentanoic acid 1-(acetyl-{3-[4-(1,1-dioxo-hexahydro-1$\lambda^6$-thiopyran-4-yl)-3-fluoro-phenyl]-2-oxo-oxazolidin-5(R)-ylmethyl}-carbamoyloxy)-ethyl ester hydrochloride, or

(42) Cyclopentanecarboxylic acid 1-(acetyl-{3-[4-(1,1-dioxo-hexahydro-1$\lambda^6$-thiopyran-4-yl)-3-fluoro-phenyl]-2-oxo-oxazolidin-5(R)-ylmethyl}-carbamoyloxy)-ethyl ester.

25. A compound of claim 1 which is (1) 2(S)-amino-3(S)-methyl-pentanoic acid (acetyl-{3-[4-(1,1-dioxo-hexahydro-1$\lambda^6$-thiopyran-4-yl)-3-fluoro-phenyl]-2-oxo-oxazolidin-5(R)-ylmethyl}-carbamoyloxy)-methyl ester hydrochloride, (2) 2(R)-amino-3-methyl-butyric acid (acetyl-{3-[4-(1,1-dioxo-hexahydro-1$\lambda^6$-thiopyran-4-yl)-3-fluoro-phenyl]-2-oxo-oxazolidin-5(R)-ylmethyl}-carbamoyloxy)-methyl ester hydrochloride, or (3) 2(S)-Amino-3(S)-methyl-pentanoic acid 1-(acetyl-{3-[4-(1,1-dioxo-hexahydro-1$\lambda^6$-thiopyran-4-yl)-3-fluoro-phenyl]-2-oxo-oxazolidin-5(R)-ylmethyl}-carbamoyloxy)-ethyl ester hydrochloride.

26. A pharmaceutical composition comprising a compound of formula I or a pharmaceutically acceptable salt thereof, and a pharmaceutically acceptable carrier.

27. A method for treating bacteria infections comprising administering to a mammal being treated a pharmaceutically effective amount of the compound of claim 1.

28. The method of claim 27 wherein said compound is administered parenterally, topically, rectally, or intranasally.

29. The method of claim 27 wherein said compound is administered orally.

30. The method of claim 28 wherein parenteral administration is subcutaneous, intravenous, intramuscular, intradermal, intrathecal, intraocular, intravetricular injection.

31. The method of claim 27 wherein said compound is administered in an amount of from about 0.1 to about 100 mg/kg of body weight/day.

32. The method of claim 27 wherein said compound is administered in an amount of from about 1 to about 50 mg/kg of body weight/day.

33. The method of claim 27 wherein said mammal is human.

34. The method of claim 27 wherein said mammal is an animal.

\* \* \* \* \*